(12) United States Patent
Gentinetta et al.

(10) Patent No.: US 12,396,943 B2
(45) Date of Patent: Aug. 26, 2025

(54) HEMOPEXIN FORMULATIONS

(71) Applicant: CSL Behring AG, Bern (CH)

(72) Inventors: Thomas Gentinetta, Bern (CH);
Nathan Brinkman, Herscher, IL (US);
David Boerema, Bourbonnais, IL (US);
Bo An, Bourbonnais, IL (US); Kyle Miner, Bourbonnais, IL (US)

(73) Assignee: CSL Behring AG, Bern (CH)

( * ) Notice: Subject to any disclaimer, the term of this patent is extended or adjusted under 35 U.S.C. 154(b) by 224 days.

(21) Appl. No.: 16/636,063

(22) PCT Filed: Aug. 8, 2018

(86) PCT No.: PCT/EP2018/071465
§ 371 (c)(1),
(2) Date: Feb. 3, 2020

(87) PCT Pub. No.: WO2019/030262
PCT Pub. Date: Feb. 14, 2019

(65) Prior Publication Data
US 2020/0237652 A1 Jul. 30, 2020

Related U.S. Application Data

(60) Provisional application No. 62/542,662, filed on Aug. 8, 2017, provisional application No. 62/663,686, filed on Apr. 27, 2018.

(51) Int. Cl.
*A61K 9/00* (2006.01)
*A61K 38/17* (2006.01)
*A61K 47/26* (2006.01)

(52) U.S. Cl.
CPC ........ *A61K 9/0019* (2013.01); *A61K 38/1709* (2013.01); *A61K 47/26* (2013.01)

(58) Field of Classification Search
CPC ...... A61K 38/17; A61K 9/0019; A61K 47/26; A61K 38/16; A61K 38/1709; A61P 7/04; Y02A 50/30
See application file for complete search history.

(56) References Cited

U.S. PATENT DOCUMENTS

| | | | |
|---|---|---|---|
| 4,540,573 | A | 9/1985 | Neurath et al. |
| 4,764,369 | A | 8/1988 | Neurath et al. |
| 7,045,601 | B2 | 5/2006 | Metzner et al. |
| 2006/0193850 | A1* | 8/2006 | Warne ........... A61K 31/4172 424/133.1 |
| 2009/0269843 | A1 | 10/2009 | Blume et al. |
| 2014/0094411 | A1 | 4/2014 | Brinkman |
| 2014/0199303 | A1* | 7/2014 | Choi ............ A61P 19/02 424/134.1 |
| 2015/0290325 | A1* | 10/2015 | Kashi ........... A61K 9/0019 424/134.1 |

FOREIGN PATENT DOCUMENTS

| | | | |
|---|---|---|---|
| CN | 102239414 A | 11/2011 | |
| CN | 103945862 A | 7/2014 | |
| CN | 104968676 A | 10/2015 | |
| JP | 2003-510368 A | 3/2003 | |
| JP | 2007-532515 A | 11/2007 | |
| JP | 2015-509526 A | 3/2015 | |
| JP | 2015-535237 A | 12/2015 | |
| WO | WO 01/24814 A1 | 4/2001 | |
| WO | WO 2005/105148 A2 | 11/2005 | |
| WO | WO 2006/018428 A2 | 2/2006 | |
| WO | WO 2010/063652 A1 | 6/2010 | |
| WO | WO 2012/050874 A2 | 4/2012 | |
| WO | WO 2013/006766 A2 | 1/2013 | |
| WO | WO 2013/164837 A1 | 11/2013 | |
| WO | WO-2014055552 A1 * | 4/2014 | ............. A61P 17/02 |
| WO | WO 2014/064637 A1 | 5/2014 | |
| WO | WO-2015017348 A2 * | 2/2015 | ............. G02B 15/14 |
| WO | WO 2016/054072 A1 | 4/2016 | |
| WO | WO 2016/201424 A1 | 12/2016 | |
| WO | WO-2017117202 A1 * | 7/2017 | ............. C07K 16/30 |

OTHER PUBLICATIONS

Altschul, Stephen F. et al., "Gapped Blast and PSI-Blast: a new generation of protein database search programs," Nucleic Acids Research, vol. 25, No. 17, pp. 3389-3402 (1997).
Ascenzi, Paolo et al., "Critical Review, Serum Heme-Albumin: An Allosteric Protein," IUBMB Life, vol. 61, No. 12, pp. 1118-1122 (2009).
Ausubel, Frederick M. et al, "Current Protocols in Molecular Biology," (2003).
Du, Wei et al., "Hydrophobic Salts Markedly Diminish Viscosity of Concentrated Protein Solutions," Biotechnology and Bioengineering, vol. 108, No. 3, pp. 632-636 (2011).
Kirschner-Zilber, Ilana et al., "The Interaction of Hemin and Biblirubin with the Human Red Cell Membrane," Biochimica et Biophysica Acta, vol. 690, pp. 20-30 (1982).
Lin, Tian et al., "Purified and Recombinant Hemopexin: Protease Activity and Effect on Neutrophil Chemotaxis," Molecular Medicine, vol. 22, pp. 22-31 (2016).
Lipiski, Miriam et al., "Human Hp1-1 and Hp2-2 Phenotype-Specific Haptoglobin Therapeutics are Both Effective In Vitro and in Guinea Pigs to Attenuate Hemoglobin Toxicity," Antioxidants & Redox Signaling, vol. 19, No. 14, pp. 1619-1633 (2013).
Mauk, Marcia R. et al., "Metal Ions and Electrolytes Regulate the Dissociation of Heme from Human Hemopexin at Physiological pH," Journal of Biological Chemistry, vol. 285, No. 27, pp. 20499-20506 (2010).
Mauk, Marcia R. et al., "An Alternative View of the Proposed Alternative Activities of Hemopexin," Protein Science, vol. 20, pp. 791-805 (2011).
Miller, Yury I. et al., "Role of Hemopexin in Protection of Low-Density Lipoprotein Against Hemoglobin-Induced Oxidation," Biochemistry, vol. 35, pp. 13112-13117 (1996).

(Continued)

*Primary Examiner* — Doan T Phan
(74) *Attorney, Agent, or Firm* — Finnegan, Henderson, Farabow, Garrett & Dunner, LLP

(57) ABSTRACT

The present invention relates generally to a stable liquid formulation of purified hemopexin comprising: (a) a hemopexin content of at least 50 mg/mL; (b) at least 15 mM phosphate buffer; (c) a pH from 5.8 to 8; and (d) at least 50 mM sodium chloride; and uses thereof.

34 Claims, 48 Drawing Sheets
Specification includes a Sequence Listing.

(56) References Cited

OTHER PUBLICATIONS

Morgan, William T. et al., "Transfer of Heme from Heme-Albumin to Hemopexin," Biochimica et Biophysica Acta., vol. 444, pp. 435-445 (1976).
Niesen, Frank H. et al., "The Use of Differential Scanning Fluorimetry to Detect Ligand Interactions that Promote Protein Stability," Nature Protocols, vol. 2, No. 9, pp. 2212-2221 (2007).
Rosell, Federico I et al., "pH- and Metal Ion-Linked Stability of the Hemopexin-Heme Complex," Biochemistry, vol. 44, pp. 1872-1879 (2005).
Tortorici, Michael A. et al., "Direct Enhancement of Cholesterol Efflux in AMI Patients: A PKPD Substudy of Aegis-I," Aegis-I Poster (2017).
International Search Report for International Application No. PCT/EP2018/071465, dated Nov. 2, 2018.
Written Opinion of the International Searching Authority for PCT/EP2018/071465.
Muller-Eberhard et al., Chapter 2: "Hemopexin, The Heme-Binding Serum β-Glycoprotein," Structure and Function of Plasma Proteins, Springer, (1974).
Phosphate-buffered saline (PBS), Cold Spring Harbor Protocols (2006).
Davies et al. "Antibody-Antigen Complexes," Annu. Rev. Biochem. 59:439-473 (1990).
Drake et al., "Characterizing high-affinity antigen-antibody complexes by kinetic- and equilibrium-based methods," Analytical Biochemistry, 328:35-43 (2004).
Hanes et al., "Picomolar affinity antibodies from a fully synthetic naïve library selected and evolved by ribosome display," Nature Biotechnology, 18 (2000).
MacCallum et al., "Antibody-antigen Interactions: Contact Analysis and Binding Site Topography," J. Mol. Biol. 262:732-745 (1996).
Paoli et al., "Crystal structure of hemopexin reveals a novel high-affinity heme site formed between two β-propellor domains," Nature Structure Biology, 6(10) (1999).
Van den Beucken et al., "Affinity maturation of Fab antibody fragments by fluorescent-activated cell sorting of yeast-displayed libraries," FEBS Letters, 546:288-294 (2003).
Ghasemisarabbadieh et al., "The effect of trehalose, antioxidants, and acetate buffer concentration on oxytocin stability," J. Pep. Sci., 27:e3324, pp. 1-6 (2021).
Wang, "Instability, stabilization, and formulation of liquid protein pharmaceuticals," International Journal of Pharmaceutics, 185:129-188 (1999).
Wang et al., "Antibody Structure, Instability, and Formulation," Journal of Pharmaceutical Sciences, 96(1):1-26 (2007).

\* cited by examiner

REDUCING

Buffer screening I
Without NaCl

With 150 mM NaCl

Buffer screening II
With 150 MM Nacl**

Buffer screening III – sugars
With 150 mM NaCl

Buffer screening IV – NaCl concentration[1]

[1] Buffer concentration was kept constant: 200 mM citrate phosphate; 100 sodium phosphate; 100 mM Tris; 100 mM Glycine

Buffer screening V – ionic strength

Buffer screening VI – ionic strength II

Buffer screening VII – amino acids

FIGURE 33A
Thermal Denaturation Data ($T_m/T_{agg}$)

| Well | mg/mL | Formulation | Tm1 | STD | % RSD | Tm2 | STD | % RSD | Tagg | STD | % RSD |
|---|---|---|---|---|---|---|---|---|---|---|---|
| A1 | 300 | Form 1-1 | | | | | | | | | |
| B1 | 300 | Form 1-1 | 50 | 1.3 | 2.5 | 62 | 1.9 | 3.1 | 44 | 2.0 | 4.5 |
| C1 | 300 | Form 1-1 | | | | | | | | | |
| D1 | 250 | Form 1-2 | | | | | | | | | |
| E1 | 250 | Form 1-2 | 50 | 1.2 | 2.4 | 65 | 1.6 | 2.5 | 41 | 0.5 | 1.2 |
| F1 | 250 | Form 1-2 | | | | | | | | | |
| G1 | 200 | Form 1-3 | | | | | | | | | |
| H1 | 200 | Form 1-3 | 53 | 2.1 | 4.0 | 66 | 2.3 | 3.4 | 46 | 1.1 | 2.3 |
| I1 | 200 | Form 1-3 | | | | | | | | | |
| J1 | 100 | Form 1-4 | | | | | | | | | |
| K1 | 100 | Form 1-4 | 49 | 0.4 | 0.7 | 64 | 0.6 | 0.9 | 49 | 1.1 | 2.2 |
| L1 | 100 | Form 1-4 | | | | | | | | | |
| | | | | | | | | | | | |
| M1 | 300 | Form 2-1 | | | | | | | | | |
| N1 | 300 | Form 2-1 | 55 | 0.8 | 1.4 | 64 | 0.5 | 0.7 | 52 | 0.4 | 0.8 |
| O1 | 300 | Form 2-1 | | | | | | | | | |
| P1 | 250 | Form 2-2 | | | | | | | | | |
| A2 | 250 | Form 2-2 | 55 | 1.0 | 1.7 | 64 | 0.8 | 1.2 | 49 | 1.5 | 3.1 |
| B2 | 250 | Form 2-2 | | | | | | | | | |
| C2 | 200 | Form 2-3 | | | | | | | | | |
| D2 | 200 | Form 2-3 | 54 | 1.2 | 2.2 | 65 | 1.4 | 2.2 | 56 | 2.8 | 4.9 |
| E2 | 200 | Form 2-3 | | | | | | | | | |
| F2 | 100 | Form 2-4 | | | | | | | | | |
| G2 | 100 | Form 2-4 | 54 | 1.4 | 2.7 | 67 | 0.3 | 0.4 | 58 | 1.8 | 3.1 |
| H2 | 100 | Form 2-4 | | | | | | | | | |
| | | | | | | | | | | | |
| I2 | 300 | Form 3-1 | | | | | | | | | |
| J2 | 300 | Form 3-1 | 61 | 2.3 | 3.8 | 69 | 2.5 | 3.6 | 51 | 1.4 | 2.8 |
| K2 | 300 | Form 3-1 | | | | | | | | | |
| L2 | 250 | Form 3-2 | | | | | | | | | |
| M2 | 250 | Form 3-2 | 56 | 0.7 | 1.3 | 70 | 1.8 | 2.6 | 52 | 1.7 | 3.2 |
| N2 | 250 | Form 3-2 | | | | | | | | | |
| O2 | 200 | Form 3-3 | | | | | | | | | |
| P2 | 200 | Form 3-3 | 56 | 1.6 | 2.8 | 67 | 0.4 | 0.6 | 52 | 6.1 | 11.8 |
| A3 | 200 | Form 3-3 | | | | | | | | | |
| B3 | 100 | Form 3-4 | | | | | | | | | |
| C3 | 100 | Form 3-4 | 55 | 0.7 | 1.2 | 70 | 0.3 | 0.4 | 57 | 0.7 | 1.3 |
| D3 | 100 | Form 3-4 | | | | | | | | | |

Figure 33B

| Well | mg/mL | Formulation | Tm1 | STD | % RSD | Tm2 | STD | % RSD | Tagg | STD | % RSD |
|---|---|---|---|---|---|---|---|---|---|---|---|
| E3 | 300 | Form 4-1 | | | | | | | | | |
| F3 | 300 | Form 4-1 | 57 | 2.3 | 4.1 | 65 | 2.5 | 3.8 | 45 | 1.5 | 3.4 |
| G3 | 300 | Form 4-1 | | | | | | | | | |
| H3 | 250 | Form 4-2 | | | | | | | | | |
| I3 | 250 | Form 4-2 | 52 | 1.2 | 2.4 | 63 | 2.1 | 3.3 | 42 | 1.7 | 3.9 |
| J3 | 250 | Form 4-2 | | | | | | | | | |
| K3 | 200 | Form 4-3 | | | | | | | | | |
| L3 | 200 | Form 4-3 | | | | 61 | 1.9 | 3.1 | 45 | 0.5 | 1.0 |
| M3 | 200 | Form 4-3 | | | | | | | | | |
| N3 | 100 | Form 4-4 | | | | | | | | | |
| O3 | 100 | Form 4-4 | 49 | 1.4 | 2.9 | 66 | 1.8 | 2.7 | 51 | 0.3 | 0.6 |
| P3 | 100 | Form 4-4 | | | | | | | | | |

FIGURE 34
Chemical Denaturation Data (ΔG in kCal/mol)

| Abbr. | HPX Patent Formulations Formulation | ΔG Trend (mg/mL) | | | | | | | | | |
|---|---|---|---|---|---|---|---|---|---|---|---|
| | | 0.25 | 1 | 5 | 10 | 25 | 50 | 100 | 200 | 250 | 300 |
| Form. 1 | 200 mM phosphate-citrate, 150 mM NaCl, 0.01% PS80 pH 7.2 | 6.3 | 6.3 | 6.3 | 6.3 | 6.3 | 6.3 | 6.3 | 6.3 | 6.3 | 6.3 |
| Form. 2 | 50 mM phosphate-citrate, 400 mM NaCl, 0.01% PS80 pH 7.2 | 6.0 | 6.1 | 6.2 | 6.2 | 6.3 | 6.3 | 6.3 | 6.4 | 6.4 | 6.4 |
| Form. 3 | 15 mM phosphate-citrate, 150 mM NaCl, 0.01% PS80 pH 7.2 | 4.0 | 4.0 | 4.0 | 4.0 | 4.0 | 4.0 | 4.0 | 4.0 | 4.0 | 4.0 |
| Form. 4 | Phosphate Buffered Saline, 0.01% PS80 pH 7.4 | 3.6 | 3.6 | 3.5 | 3.5 | 3.4 | 3.4 | 3.4 | 3.3 | 3.3 | 3.3 |

HEMOPEXIN FORMULATIONS

This application is a national stage filing under 35 U.S.C. § 371 of International Application No. PCT/EP2018/071465, filed on Aug. 8, 2018, which claims the benefit of the filing dates of U.S. Provisional Application No. 62/542,662, filed on Aug. 8, 2017, and of U.S. Provisional Application No. 62/663,686, filed on Apr. 27, 2018, each of which is incorporated herein by reference.

TECHNICAL FIELD

The present invention relates generally to a stable liquid formulation of hemopexin and uses thereof.

BACKGROUND

Haemolysis is characterized by the destruction of red blood cells and is a hall-mark of anaemic disorders associated with red blood cell abnormalities, such as enzyme defects, haemoglobinopathies, hereditary spherocytosis, paroxysmal nocturnal haemoglobinuria and spur cell anaemia, as well as extrinsic factors such as splenomegaly, autoimmune disorders (e.g., Haemolytic disease of the newborn), genetic disorders (e.g., Sickle-cell disease or G6PD deficiency), microangiopathic haemolysis, Gram-positive bacterial infection (e.g., *Streptococcus, Enterococcus* and *Staphylococcus*), parasite infection (e.g., *Plasmodium*), toxins and trauma (e.g., burns). Haemolysis is also a common disorder of blood transfusions, particularly massive blood transfusions and in patients using an extracorporeal cardiopulmonary support.

The adverse effects seen in patients with conditions associated with haemolysis are largely attributed to the release of iron and iron-containing compounds, such as haemoglobin (Hb) and heme, from red blood cells. Under physiological conditions, released haemoglobin is bound by soluble proteins such as haptoglobin and transported to macrophages and hepatocytes. However, where the incidence of haemolysis is accelerated and becomes pathological in nature, the buffering capacity of haptoglobin is overwhelmed. As a result, haemoglobin is quickly oxidised to ferri-haemoglobin, which in turn releases free heme (comprising protoporphyrin IX and iron). Whilst heme plays a critical role in several biological processes (e.g., as part of essential proteins such as haemoglobin and myoglobin), free heme is highly toxic. Free heme is a source of redox-active iron, which produces highly toxic reactive oxygen species (ROS) that damages lipid membranes, proteins and nucleic acids. Heme toxicity is further exacerbated by its ability to intercalate into lipid membranes, where it causes oxidation of membrane components and promotes cell lysis and death.

The evolutionary pressure of continuous low-level extracellular Hb/heme exposure has led to compensatory mechanisms that control the adverse effects of free Hb/heme under physiological steady-state conditions and during mild haemolysis. These systems include the release of a group of plasma proteins that bind Hb or heme, including the Hb scavenger haptoglobin (Hp) and the heme scavenger proteins hemopexin (Hpx) and α1-microglobulin.

Hemopexin is a 61-kDa plasma β-1B-glycoprotein composed of a single 439 amino acids long peptide chain, which is formed by two four-bladed β-propeller domains, resembling two thick disks that lock together at a 90° angle and are joined by an interdomain linker peptide as shown in FIG. 1 (Mauk, 2011; *Protein Science*, Volume 20, pp. 791-805). The heme, which is released into the blood as the result of intra- and extra-vascular haemolysis, is bound between the two four-bladed β-propeller domains in a pocket formed by the interdomain linker peptide. Residues His213 and His266 coordinate the heme iron atom giving a stable bis-histidyl complex, similar to haemoglobin.

Hemopexin contains about 20% carbohydrates, including sialic acid, mannose, galactose, and glucosamine. Twelve cysteine residues were found in the protein sequence, probably accounting for six disulphide bridges. Hemopexin represents the primary line of defense against heme toxicity thanks to its ability to bind heme with high affinity ($K_d$<1 pM) and to function as a heme specific carrier from the bloodstream to the liver. It binds heme in an equimolar ratio, but there is no evidence that heme is covalently bound to the protein.

In addition to heme binding, hemopexin preparations have also been reported to possess serine protease activity (Lin et. al., 2016; Molecular Medicine 22:22-31, 2016) and several other functions, such as exhibition of anti- and pro-inflammatory activities, inhibition of cellular adhesion and binding of certain divalent metal ions.

Whilst endogenous hemopexin can control the adverse effects of free heme under physiological steady-state conditions, it has little effect in maintaining steady-state heme levels under pathophysiogical conditions, such as those associated with haemolysis, where a high level of heme leads to the depletion of endogenous hemopexin, causing heme-mediated oxidative tissue damage. Studies have shown that hemopexin infusion alleviates heme-induced endothelial activation, inflammation, and oxidative injury in experimental mouse models of haemolytic disorders, such as sickle-cell disease (SCD) and β-thalassemia. Hemopexin administration has also been shown to significantly reduce the level of proinflammatory cytokines and counteract heme-induced vasoconstriction in haemolytic animals. However, whilst purified hemopexin shows important therapeutic potential, it suffers from poor stability as a liquid preparation.

The present disclosure solves, or at least partly alleviates, this problem by providing a stable liquid formulation of hemopexin that is suitable for therapeutic use.

SUMMARY OF THE INVENTION

In an aspect of the present invention, there is provided a stable liquid formulation of purified hemopexin comprising:
(a) a hemopexin content of at least 50 mg/mL;
(b) at least 15 mM phosphate buffer;
(c) a pH from 5.8 to 8; and
(d) at least 50 mM sodium chloride.

In another aspect of the present invention, there is provided a method of treating a condition associated with haemolysis, the method comprising administering to a subject in need thereof the liquid formulation of purified hemopexin as disclosed herein.

Figure 27:
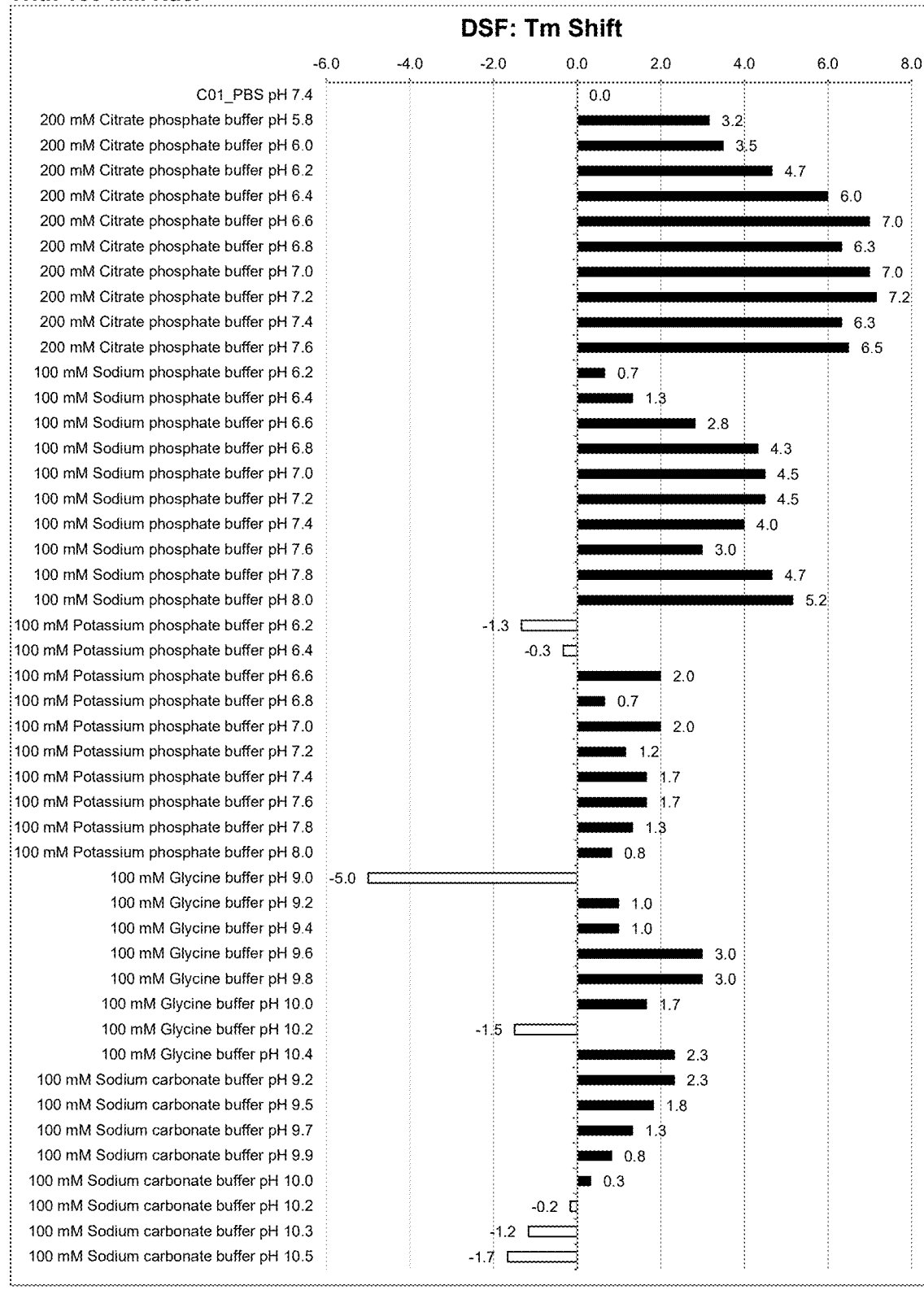

FIG. 27 shows a horizontal bar graph depicting shift in $T_m$ (as measured by DSF) in various buffers of varying pH (200 mM citrate phosphate buffer, 100 mM sodium phosphate buffer, 100 mM potassium phosphate buffer, 100 mM glycine buffer, and 100 mM sodium carbonate buffer), each of which comprises 150 mM NaCl.

Figure 28:
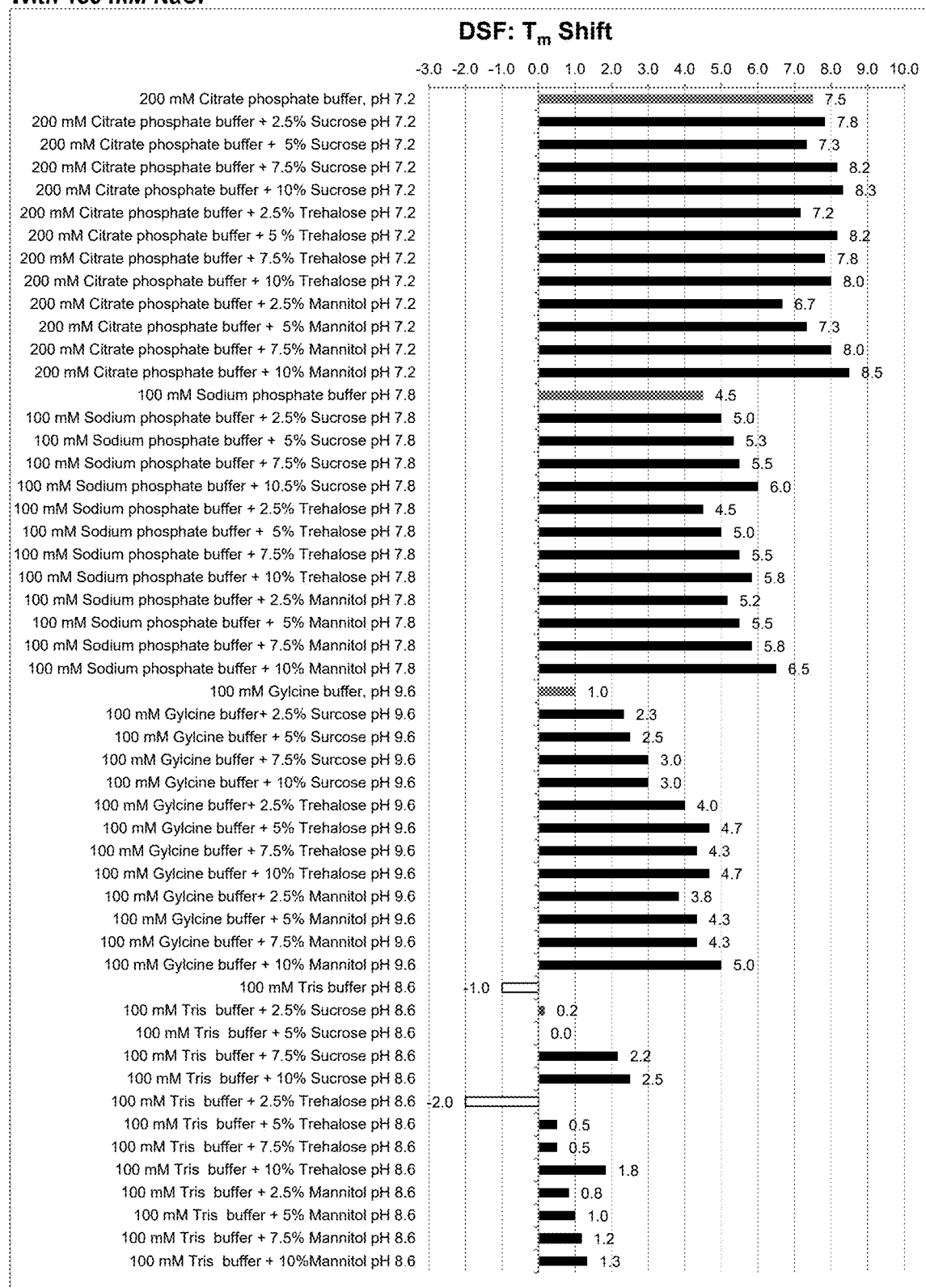

FIG. 28 shows a horizontal bar graph depicting shift in $T_m$ (as measured by DSF) in various buffers of varying pH (200 mM citrate phosphate buffer, 100 mM sodium phosphate buffer, 100 mM glycine buffer, and 100 mM Tris buffer), each of which comprises 150 mM NaCL and various concentrations of the sugars sucrose, trehalose or mannitol.

Figure 29:
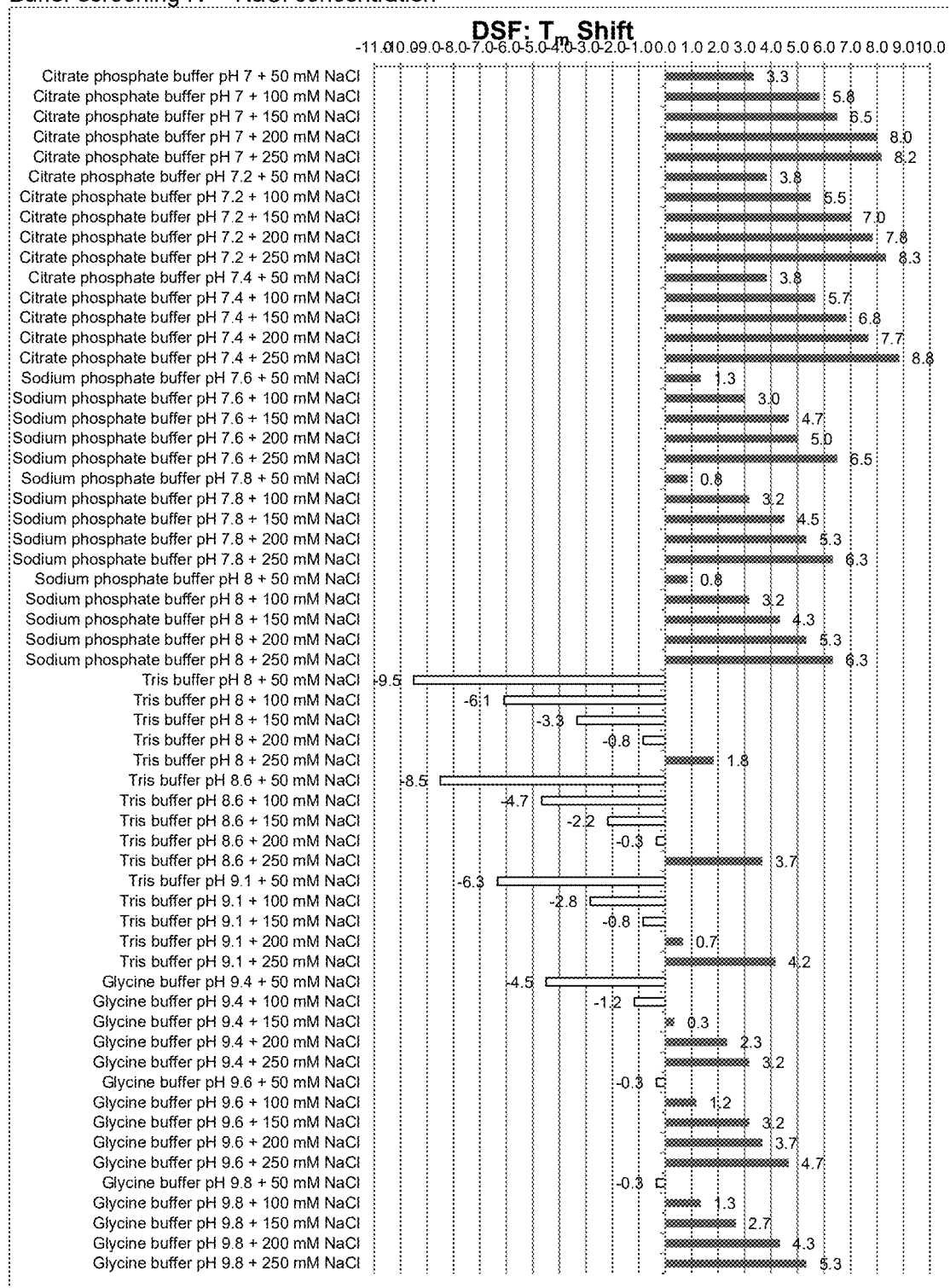

FIG. 29 shows a horizontal bar graph depicting shift in $T_m$ (as measured by DSF) in various buffers of varying pH (200 mM citrate phosphate buffer, 100 mM sodium phosphate buffer, 100 mM Tris buffer, and 100 mM glycine buffer), each of which comprises 50 mM, 100 mM, 150 mM, 200 mM, or 250 mM NaCl.

Figure 30:
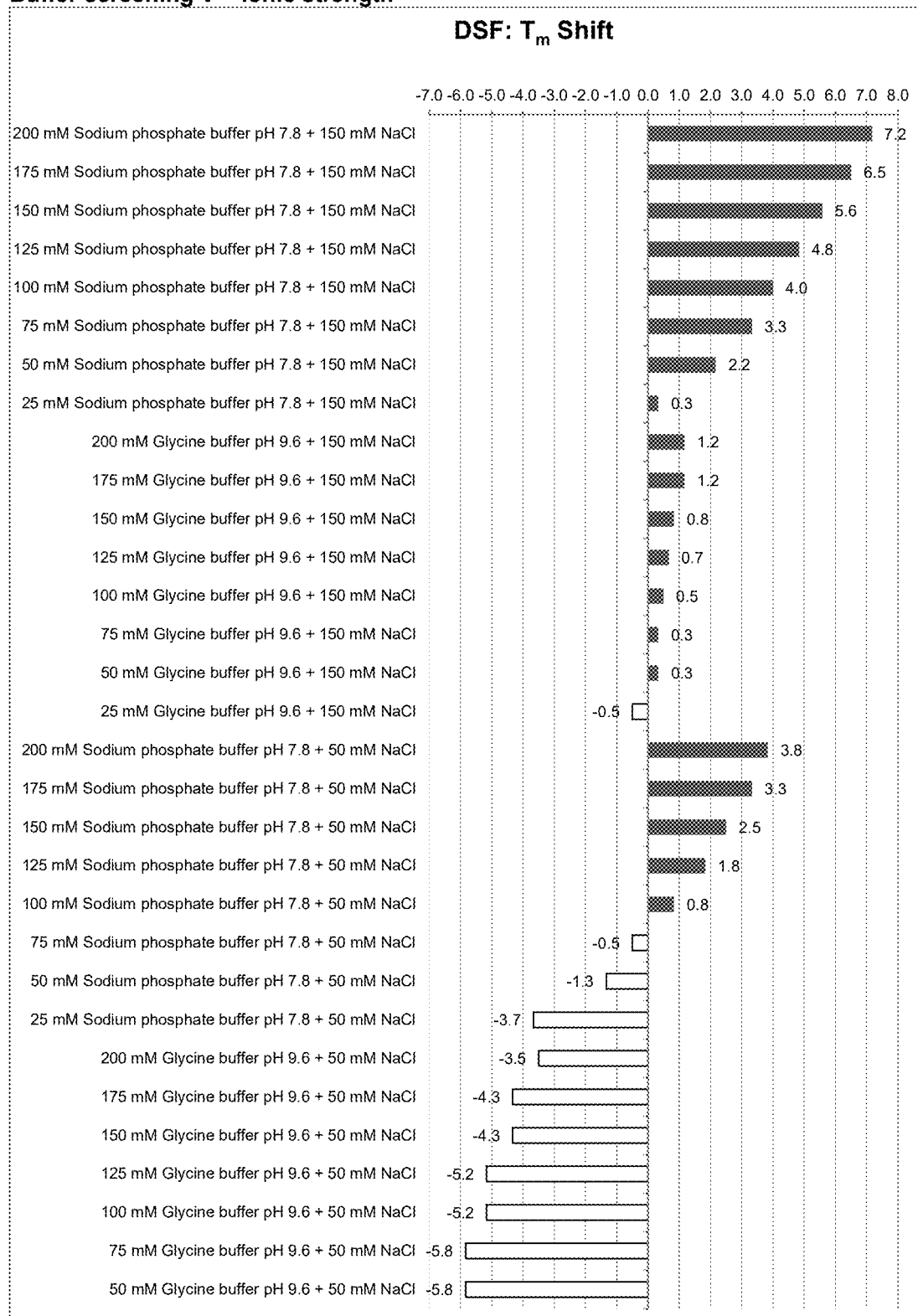

FIG. 30 shows a horizontal bar graph depicting shift in $T_m$ (as measured by DSF) in various buffers of varying ionic strength (sodium phosphate buffer at pH 7.8, glycine buffer at pH 9.6, sodium phosphate buffer at pH 7.8, and glycine buffer at pH 9.6), each of which comprises 50 mM or 150 mM NaCl.

Figure 31A:
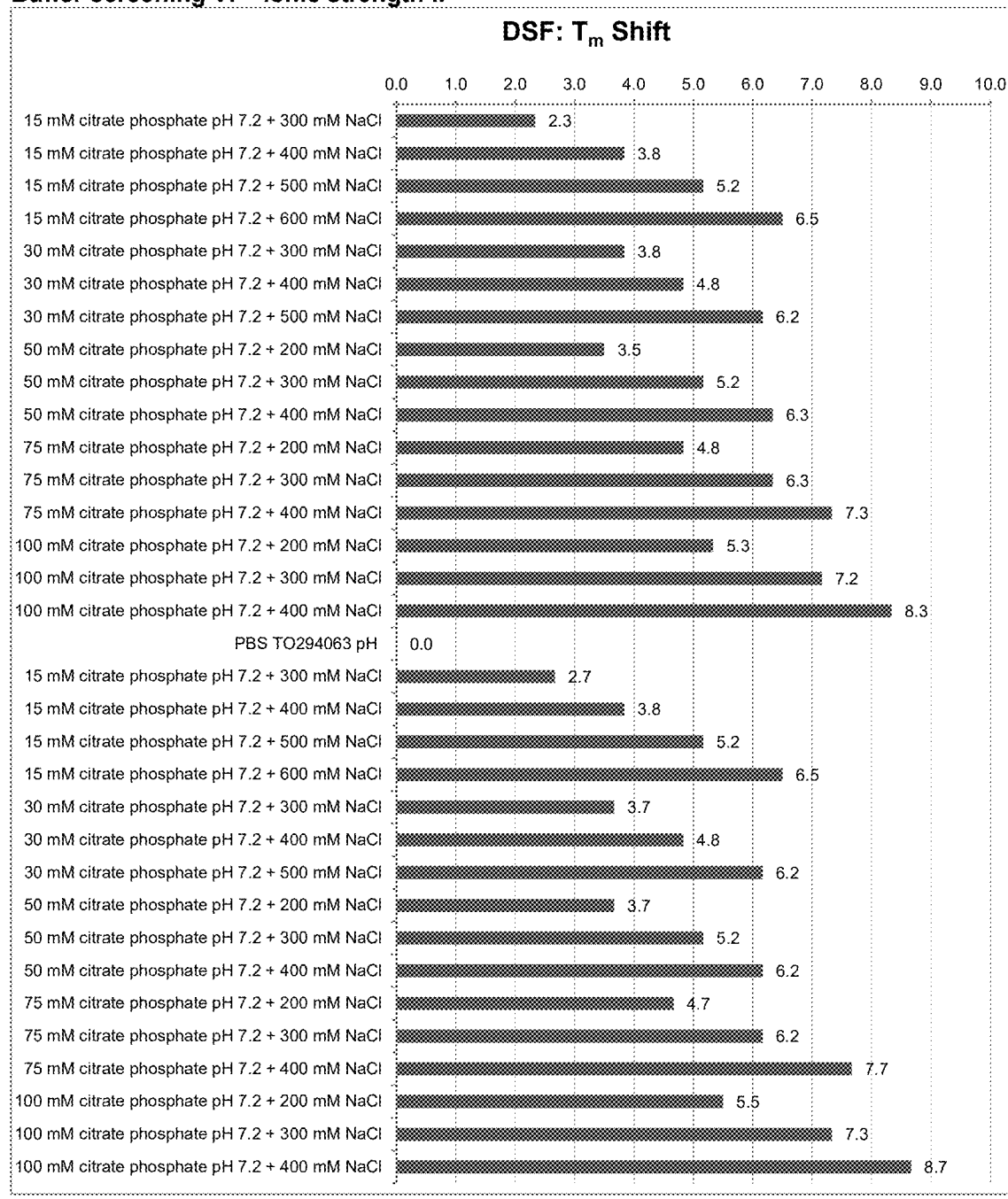
Figure 31B:
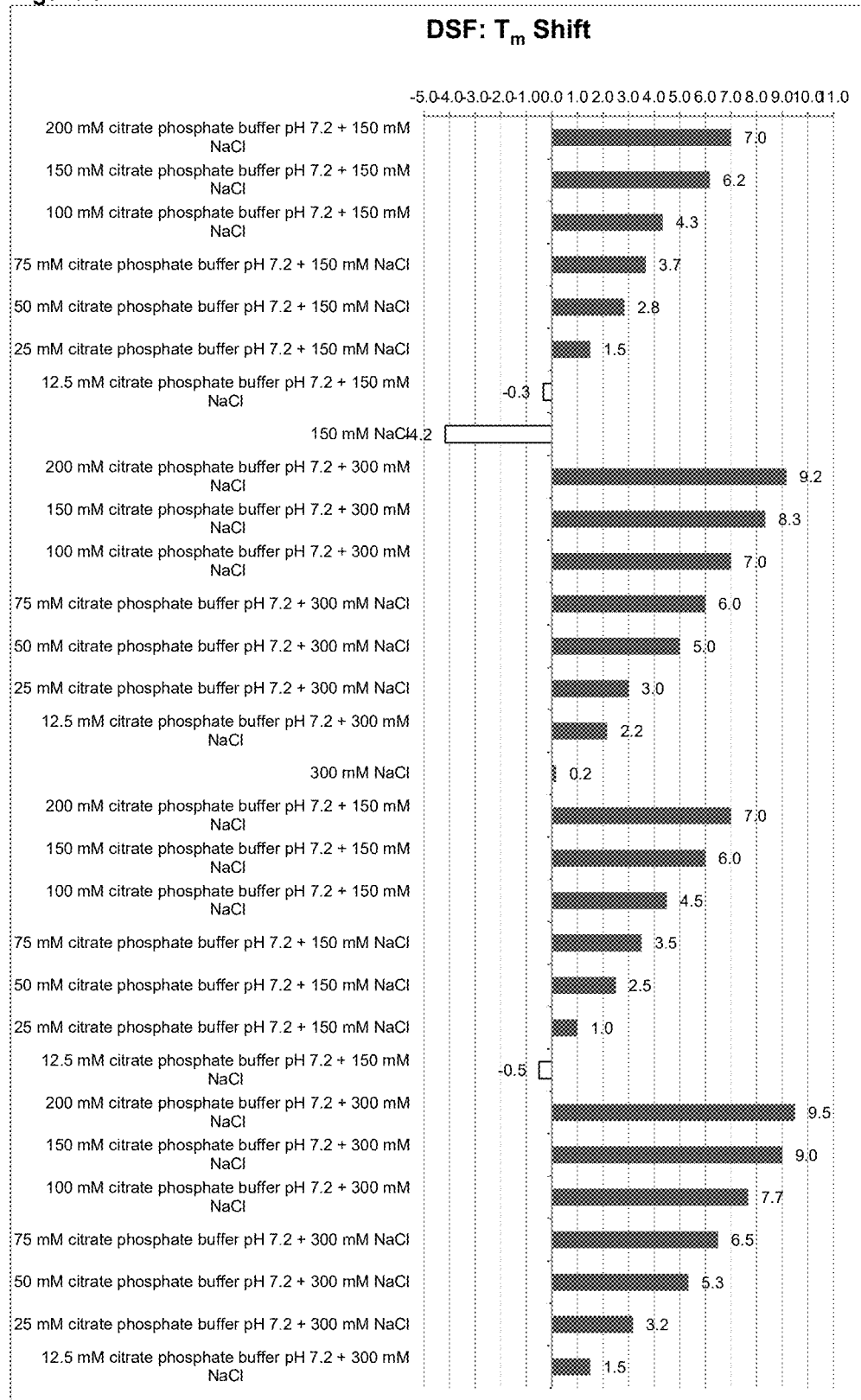

FIG. 31A-B show a horizontal bar graph depicting shift in $T_m$ (as measured by DSF) in citrate phosphate buffer at pH 7.2 of varying ionic strength and comprising 150 mM, 200 mM, 300 mM, 400 mM, 500 mM, or 600 mM NaCl.

Figure 32:
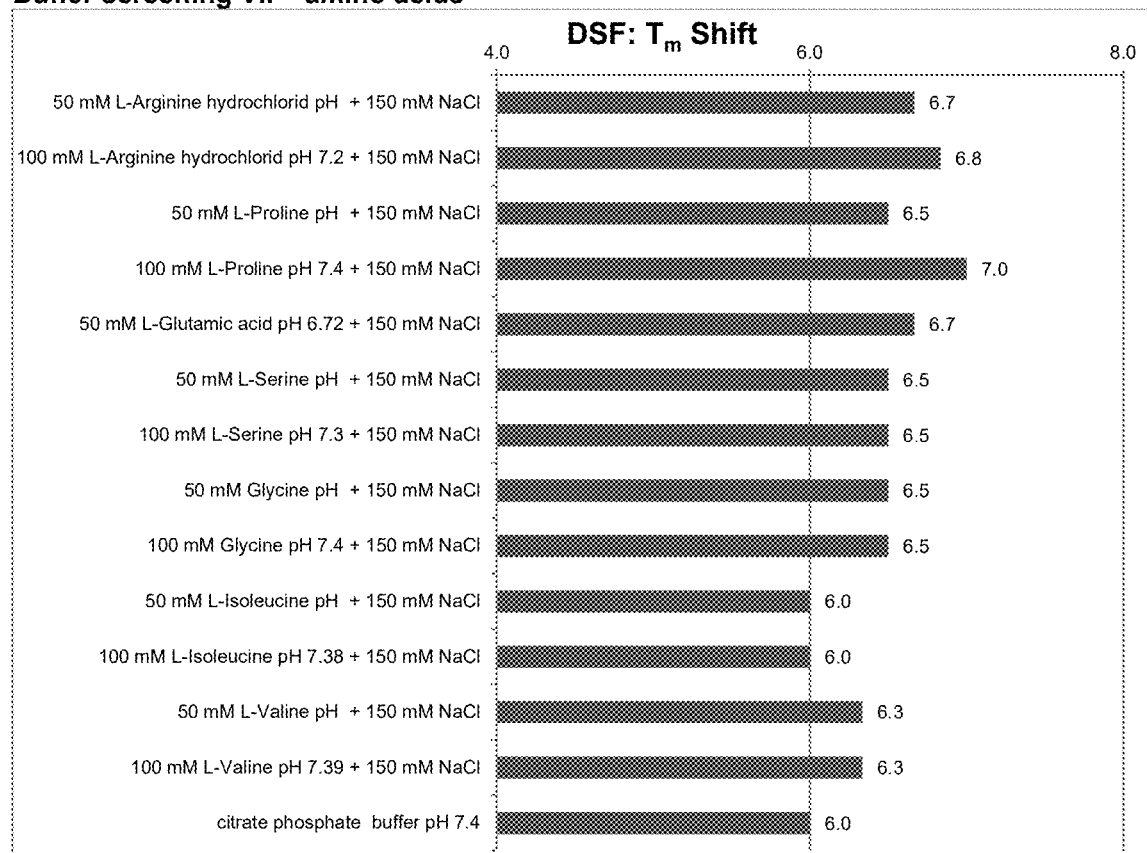

FIG. 32 shows a horizontal bar graph depicting shift in $T_m$ (as measured by DSF) in various amino acid buffers of varying ionic strength and pH and comprising 150 mM NaCl.

FIG. 33A-B show a table depicting thermal denaturation data (as measured by $T_m/T_{agg}$) for various formulations.

FIG. 34 shows a table depicting chemical denaturation data (as measured by $\Delta G$ in kCal/mol) for various formulations.

DETAILED DESCRIPTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It must be noted that, as used in the subject specification, the singular forms "a", "an" and "the" include plural aspects unless the context clearly dictates otherwise. Thus, for example, reference to "a condition associated with haemolysis" includes a single condition, as well as two or more conditions; reference to "an agent" includes a single agent, as well as two or more agents; and so forth.

In the absence of any indication to the contrary, reference made to a "%" content throughout this specification is to be taken as meaning % w/v (weight/volume). For example, a liquid formulation comprising a hemopexin content of at least 10% is taken to mean a liquid formulation comprising a hemopexin content of at least 10% w/v (i.e., of at least 100 mg/mL).

The present invention is predicated, at least in part, on the inventors' surprising finding that certain conditions can be modified to enhance the stability of hemopexin in a liquid formulation thereof.

Thus, in an aspect of the present invention, there is provided a stable liquid formulation of purified hemopexin comprising:
(a) a hemopexin content of at least 50 mg/mL;
(b) at least 15 mM phosphate buffer;
(c) a pH from 5.8 to 8; and
(d) at least 50 mM sodium chloride.

Hemopexin

Hemopexin represents the primary line of defence against heme toxicity, attributed at least in part to its ability to bind heme with high affinity ($K_d$<1 pM) and to function as a heme specific carrier from the bloodstream to the liver. Hemopexin has also been reported to possess serine protease activity and several other functions, such as anti- and pro-inflammatory activities, the ability to inhibit cellular adhesion and binding of certain divalent metal ions. Some of the characteristics of hemopexin are summarized in Table 1, below:

TABLE 1

| | |
|---|---|
| size [kDa]: | ~61 ± 2 |
| length: | 439 amino acids, single polypeptide chain |
| disulphide bridges: | 6 |
| carbohydrate content [%]: | 20-22 |
| Structure: | four-bladed β-propeller fold and 2 domains |
| Heme binding pocket: | between the two domains, highly hydrophobic |
| Heme affinity, $K_d$: | <1 pM |
| UV Extinction coefficient at 280 nm [mL/(mg × cm)]: | 1.97 |
| Theoretical pI: | 6.55 |
| Average of hydrophobicity: | −0.43 (no high scoring hydrophobic segments) |

The hemopexin content of the liquid formulation may depend on the intended use. For instance, where the liquid formulation is to be administered to a subject in need thereof as a neat composition (i.e., without further dilution), the hemopexin content will typically be suitable for direct administration, having regard, for example, to factors such as the dosage required and the volume to be administered. As an example, the hemopexin content may be optimised such that it is high enough so to minimize the volume of the liquid formulation to be administered to the subject, having regard to the desired therapeutic dose, and low enough so as to minimize the viscosity of the liquid formulation to allow for administration without further dilution. Thus, in an embodiment disclosed herein, the hemopexin content is optimised so as to minimize the viscosity of the liquid formulation such that it is suitable for administration without further dilution. Suitable viscosities will be familiar to persons skilled in the art and is likely to depend on factors such as the route and/or volume of administration. It is noted in W. Du & A. Klibanov, "Hydrophobic Salts Markedly Diminish Viscosity of Concentrated Protein Solutions", Biotechnology and Bioengineering, pp. 632-636, 2011 that the threshold for subcutaneous injections of protein containing formulations can be as high as 50 mPa*s. In particular embodiment disclosed herein, the liquid formulation comprises a viscosity of less than or equal to 50 mPa*s at 25° C. In a preferred embodiment disclosed herein, the liquid formulation comprises a viscosity of less than or equal to 20 mPa*s at 25° C.

Where the liquid formulation is to be administered to a subject in need thereof as a neat composition (i.e., without further dilution), suitable dosages of purified hemopexin will be familiar to persons skilled in the art and are likely to depend on factors such as the nature and severity of the haemolytic condition to be treated (e.g., level of endogenous free heme), the age, weight and gender of the subject to be treated, the presence of any other underlying conditions and combinations of the foregoing.

Reference to "at least 50 mg/mL" includes 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 105 mg/mL, 110 mg/mL, 115 mg/mL, 120 mg/mL, 125 mg/mL, 130 mg/mL, 135 mg/mL, 140 mg/mL, 145 mg/mL, 150 mg/mL, 155 mg/mL, 160 mg/mL, 165 mg/mL, 170 mg/mL, 175 mg/mL, 180 mg/mL, 185 mg/mL, 190 mg/mL, 195 mg/mL, 200 mg/mL, 205 mg/mL, 210 mg/mL, 215 mg/mL, 220 mg/mL, 225 mg/mL, 230 mg/mL, 235 mg/mL, 240 mg/mL, 245 mg/mL, 250 mg/mL, 255 mg/mL, 260 mg/mL, 265 mg/mL, 270 mg/mL, 275 mg/mL, 280 mg/mL, 285 mg/mL, 290 mg/mL, 295 mg/mL, 300 mg/mL, 305 mg/mL, 310 mg/mL, 315 mg/mL, 320 mg/mL, 325 mg/mL, 330 mg/mL, 335 mg/mL, 340 mg/mL, 345 mg/mL, 350 mg/mL, 355 mg/mL, 360 mg/mL, 365 mg/mL, 370 mg/mL, 375 mg/mL, 380 mg/mL, 385 mg/mL, 390 mg/mL, 400 mg/mL, 405 mg/mL and so on. Thus, in preferred forms of the present invention, the liquid formulation comprises a hemopexin content of at least 50 mg/mL, preferably at least 55 mg/mL, preferably at least 60 mg/mL, preferably at least 65 mg/mL, preferably at least 70 mg/mL, preferably at least 75 mg/mL, preferably at least 80 mg/mL, preferably at least 85 mg/mL, preferably at least 90 mg/mL, preferably at least 95 mg/mL, preferably at least 100 mg/mL, preferably at least 105 mg/mL, preferably at least 110 mg/mL, preferably at least 115 mg/mL, preferably at least 120 mg/mL, preferably at least 125 mg/mL, preferably at least 130 mg/mL, preferably at least 135 mg/mL, preferably at least 140 mg/mL, preferably at least 145 mg/mL, preferably at least 150 mg/mL, preferably at least 155 mg/mL, preferably at least 160 mg/mL, preferably at least 165 mg/mL, preferably at least 170 mg/mL, preferably at least 175 mg/mL, preferably at least 180 mg/mL, preferably at least 185 mg/mL, preferably at least 190 mg/mL, preferably at least 195 mg/mL, preferably at least 200 mg/mL, preferably at least 205 mg/mL, preferably at least 210 mg/mL, preferably at least 215 mg/mL, preferably at least 220 mg/mL, preferably at least 225 mg/mL, preferably at least 230 mg/mL, preferably at least 235 mg/mL, preferably at least 240 mg/mL, preferably at least 245 mg/mL, preferably at least 250 mg/mL, preferably at least 255 mg/mL, preferably at least 260 mg/mL, preferably at least 265 mg/mL, preferably at least 270 mg/mL, preferably at least 275 mg/mL, preferably at least 280 mg/mL, preferably at least 285 mg/mL, preferably at least 290 mg/mL, preferably at least 295 mg/mL, preferably at least 300 mg/mL, preferably at least 305 mg/mL, preferably at least 310 mg/mL, preferably at least 315 mg/mL, preferably at least 320 mg/mL, preferably at least 325 mg/mL, preferably at least 330 mg/mL, preferably at least 335 mg/mL, preferably at least 340 mg/mL, preferably at least 345 mg/mL, preferably at least 350 mg/mL, preferably at least 355 mg/mL, preferably at least 360 mg/mL, preferably at least 365 mg/mL, preferably at least 370 mg/mL, preferably at least 375 mg/mL, preferably at least 380 mg/mL, preferably at least 385 mg/mL, preferably at least 390 mg/mL, preferably at least 400 mg/mL, preferably at least 405 mg/mL, and so on.

In an embodiment disclosed herein, the liquid formulation comprises from 75 mg/mL to 300 mg/mL hemopexin. In an embodiment disclosed herein, the liquid formulation comprises from 75 mg/mL to 250 mg/mL hemopexin. In an embodiment disclosed herein, the liquid formulation comprises from 75 mg/mL to 200 mg/mL hemopexin. In an embodiment disclosed herein, the liquid formulation comprises from 75 mg/mL to 150 mg/mL hemopexin. In an embodiment disclosed herein, the liquid formulation comprises from 100 mg/mL to 300 mg/mL hemopexin. In an embodiment disclosed herein, the liquid formulation comprises from 150 mg/mL to 300 mg/mL hemopexin. In an embodiment disclosed herein, the liquid formulation comprises from 200 mg/mL to 300 mg/mL hemopexin. In an embodiment disclosed herein, the liquid formulation comprises from 250 mg/mL to 300 mg/mL hemopexin. In an embodiment disclosed herein, the liquid formulation comprises from 100 mg/mL to 200 mg/mL hemopexin. In another embodiment disclosed herein, the liquid formulation comprises 300 mg/mL hemopexin. In another embodiment disclosed herein, the liquid formulation comprises 250 mg/mL hemopexin. In another embodiment disclosed herein, the liquid formulation comprises 200 mg/mL hemopexin. In another embodiment disclosed herein, the liquid formulation comprises from 100 mg/mL to 200 mg/mL hemopexin. In yet another embodiment disclosed herein, the liquid formulation comprises about 100 mg/mL hemopexin. In another embodiment disclosed herein, the liquid formulation comprises 100 mg/mL hemopexin.

In an embodiment disclosed herein, the liquid formulation of the present invention has a volume of at least 5 mL and comprises at least 75 mg/mL hemopexin. In another embodiment, the liquid formulation has a volume of at least 5 mL and comprises at least 100 mg/mL or at least 200 mg/mL hemopexin. In particular embodiments, the liquid formulation has a volume of at least 5 mL and comprises hemopexin at a concentration of about 100 mg/mL, about 125 mg/mL, about 150 mg/mL, about 175 mg/mL, about 200 mg/mL, about 225 mg/mL, about 250 mg/mL, about 275 mg/mL, about 300 mg/mL, about 325 mg/mL, about 350 mg/mL, about 375 mg/mL or about 400 mg/mL. In another aspect, there is provided a vessel containing at least 5 mL of a stable liquid formulation of purified hemopexin, wherein the concentration of hemopexin is at least 100 mg/mL or at least 200 mg/mL or at least 250 mg/mL or at least 300 mg/mL. In another aspect, there is provided a vessel containing at least 5 mL of a stable liquid formulation of purified hemopexin, wherein the concentration of hemopexin is 100 mg/mL or 200 mg/mL or 250 mg/mL or 300 mg/mL.

In other embodiments, the liquid formulation can be prepared as a hemopexin concentrate, wherein the concentrate is to be diluted for administration. One of the advantages of preparing the liquid formulation as a hemopexin concentrate is that it minimizes the volume for storage. The concentrate can be diluted prior to or during administration to the subject, as desired. Suitable concentrations of purified hemopexin that can be prepared as a concentrate will be familiar to persons skilled in the art. In an embodiment disclosed herein, the liquid formulation comprises a hemopexin content of at least 250 mg/mL.

Reference to "at least 250 mg/mL" includes 250 mg/mL, 260 mg/mL, 270 mg/mL, 280 mg/mL, 290 mg/mL, 300 mg/mL, 305 mg/mL, 310 mg/mL, 315 mg/mL, 320 mg/mL, 325 mg/mL, 330 mg/mL, 335 mg/mL, 340 mg/mL, 345 mg/mL, 350 mg/mL, 355 mg/mL, 360 mg/mL, 365 mg/mL, 370 mg/mL, 375 mg/mL, 380 mg/mL, 385 mg/mL, 390 mg/mL, 400 mg/mL, 405 mg/mL and so on. Thus, in preferred forms of the present invention, the liquid formulation comprises a hemopexin content of at least 300 mg/mL, preferably at least 305 mg/mL, preferably at least 310 mg/mL, preferably at least 315 mg/mL, preferably at least 320 mg/mL, preferably at least 325 mg/mL, preferably at least 330 mg/mL, preferably at least 335 mg/mL, preferably at least 340 mg/mL, preferably at least 345 mg/mL, preferably at least 350 mg/mL, preferably at least 355 mg/mL, preferably at least 360 mg/mL, preferably at least 365 mg/mL, preferably at least 370 mg/mL, preferably at least 375 mg/mL, preferably at least 380 mg/mL, preferably at least 385 mg/mL, preferably at least 390 mg/mL, preferably at least 400 mg/mL, preferably at least 405 mg/mL, and so on. In an embodiment disclosed herein, the liquid formulation comprises a hemopexin content of at least 300 mg/mL.

In an embodiment, the hemopexin content is measured by UV absorbance spectroscopy. In an alternate embodiment the hemopexin is measured by immunonephelometry. Illustrative examples of UV absorbance spectroscopy and immunonephelometry are described elsewhere herein.

As used herein, the term "hemopexin" is intended to mean a hemopexin protein that has been isolated or otherwise at least partially purified from a natural source (e.g., plasma), or a recombinantly produced hemopexin protein, that comprises, consists of, or consists essentially of amino acid residues 24-462 of SEQ ID NO:1, or an amino acid sequence having at least 60% sequence identity thereto. The hemopexin may include human and non-human variants. Where the liquid formulation is intended for administration to a human subject, it is generally preferable that the hemopexin is a human hemopexin. However, it is to be understood that a non-human isoform of hemopexin may be used where the intended subject is a human, as long as the non-human isoform of hemopexin retains the ability to bind to human heme.

Conversely, where the liquid formulation is intended for administration to a non-human subject, it is generally preferable that the hemopexin is derived from the species to which it is to be administered, although it is also to be understood that a human isoform of hemopexin may be used where the intended subject is a non-human subject, as long as the human isoform of hemopexin retains the ability to bind to heme of or in the intended non-human subject. As used herein, the term "derived from" is intended to include hemopexin that is isolated or otherwise at least partially purified from its natural source, as well as recombinantly produced hemopexin that comprises an amino acid sequence that is identical or substantially identical to the amino acid sequence of hemopexin derived from that species. Illustrative examples of non-human isoforms of hemopexin will be familiar to persons skilled in the art, illustrative examples of which include hemopexin derived from bovine, equine or porcine.

In an embodiment disclosed herein, the hemopexin is a human hemopexin. This may include an at least partially purified hemopexin recovered from human plasma or recombinantly produced hemopexin. Suitable methods of purifying hemopexin from plasma will be familiar to persons skilled in the art, an illustrative example of which is described in WO2014/055552, the entire content of which is incorporated herein by reference. In particular embodiments, the liquid formulation of purified hemopexin of the present invention is manufactured at commercial scale from a plasma fraction or a recombinant feedstock. As an illustrative example, when using plasma fractions as a starting material, commercial scale manufacture involves the use of a plasma fraction derived from at least about 500 kg of plasma. Preferably, the starting plasma fraction is derived from at least about 2,000 kg, 3,000 kg, 4,000 kg, 5,000 kg, 7,500 kg, 10,000 kg and/or 15,000 kg of plasma per batch.

Where the liquid formulation comprises hemopexin that has been purified from feedstock such as blood plasma and is to be used for clinical or veterinary applications (e.g., for administration to a subject with a condition associated with haemolysis), persons skilled in the art will understand that it may be desirable to reduce the level of active virus content (virus titre) and other potential infectious agents (for example, prions) in the solution. This may be particularly desirable where the feedstock comprising hemopexin (i.e., the starting material) is derived from blood plasma. Methods of reducing the virus titre in a solution will be known to persons skilled in the art. Examples include pasteurization (for example, incubating the solution at 60° C. for 10 hours in the presence of high concentrations of stabilisers such as glycine (e.g. 2.75 M) and sucrose (e.g. 50%) and/or other selected excipients or salts), dry heat treatment, virus filtration (passing the solution through a nano-filter; e.g., 20 nm cutoff) and/or subjecting the solution to treatment with a suitable organic solvent and detergent for a period of time and under conditions to inactivate virus in the solution. Solvent detergent has been used for over 20 years to inactivate enveloped viruses particularly in plasma-derived products. Thus it may be carried out using various reagents and methods known in the art (see, for example, U.S. Pat. Nos. 4,540,573 and 4,764,369 which are hereby incorporated by reference in their entirety). Suitable solvents include tri-n-butyl phosphate (TnBP) and ether. In some embodiments, the solvent is about 0.3%, and, preferably TnBP. Suitable detergents include non-ionic detergents such as polysorbate (Tween) 80, polysorbate (Tween) 20, Triton X-100, Octyl glucoside (OPG) (typically at about 1%). The selection of treatment conditions including solvent and detergent concentrations depend in part on the characteristics of the feedstock with less pure feedstocks generally requiring higher concentrations of reagents and more extreme reaction conditions. A preferred detergent is polysorbate 80 and a particularly preferred combination is polysorbate 80 and TnBP. A preferred detergent is polysorbate 20 and a particularly preferred combination is polysorbate 20 and TnBP. A preferred detergent is OPG and a particularly preferred combination is OPG and TnBP. The feedstock may be stirred with solvent and detergent reagents at a temperature and for a time sufficient to inactivate any enveloped viruses that may be present. For example, the solvent detergent treatment may be carried out for about 4 hours at 25° C. The solvent detergent chemicals are subsequently removed by for example adsorption on chromatographic media such as C-18 hydrophobic resins or eluting them in the drop-through fraction of ion exchange resins under conditions which adsorb the protein of interest.

The virus inactivation step can be performed at any suitable stage of the purification process. In an embodiment disclosed herein, the viral inactivation step comprises pasteurisation or treatment with an organic solvent and detergent. In another embodiment disclosed herein, the virus inactivation step comprises virus filtration. Where virus filtration is used, the addition of a free amino acid (e.g., arginine) prior to the filtration step can significantly improve the flux rate and recovery of hemopexin through the filter. In an embodiment disclosed herein, the feedstock or solution comprising hemopexin is subject to a viral inactivation step prior to purification of hemopexin. An advantage of employing a virus inactivation step such as solvent detergent treatment prior to purification is that it allows for the removal of the organic solvent and detergent from the treated solution by utilizing conditions that promote binding of the hemopexin to a resin and removal of the organic solvent and detergent with the flow-through (drop-through) fraction.

In some embodiments, the liquid formulations of purified hemopexin, as disclosed herein, are substantially free of other components with which they are normally associated (e.g., other plasma-derived proteins). Thus, in an embodiment, the liquid formulation will comprise less than 20% of total protein, preferably less than 10% of total protein, and more preferably less than 5% of total protein of other components with which they are normally associated (i.e., impurities). The skilled person will understand that the level of impurities present in the liquid formulation of the present invention may depend on the intended use of the compositions. For example, where the compositions are to be administered to a human subject in need thereof (i.e., for clinical use), it would be desirable that the composition comprises less than 5% impurities (of total protein). Conversely, where the proteins are to be used in vitro, it may be acceptable if the composition comprises more than 5% of impurities (of total protein). In an embodiment, the liquid formulation will comprise a hemopexin content of at least 90%, preferably at least 95%, preferably at least 97%, preferably or at least 98%, preferably at least 99% or more preferably at least 99.5% by weight of total protein. In particular embodiments, the level of purity of hemopexin in the liquid formulation is determined using immunonephelometry. Suitable methods of performing immunonephelometry will be familiar to persons skilled in the art. The level of purity of hemopexin in the liquid formulation can be determined by measuring the hemopexin content by immunonephelometry on a BNII instrument (Siemens Healthcare, Malvern, PA, USA) or similar. The total protein content of the liquid formulation can be determined by the Bradford method or UV spectrometry at 280 nm. Then the percentage purity of hemopexin can be calculated by dividing the hemopexin content by the total protein content and multiplying by 100. The percentage purity of other trace proteins contained in the stable liquid formulations of purified hemopexin can be determined in an analogous manner. Where the hemopexin has been purified from human plasma, illustrative examples of trace proteins that may be present in the liquid formulation include albumin, alpha-1-acid glycoprotein, alpha-1-antitrypsin, alpha-2-macroglobulin, apolipoprotein A-I, antithrombin-II, ceruloplasmin, haptoglobin, immunoglobulin A (IgA), immunoglobulin G (IgG) and transferrin.

A recombinant hemopexin may be prepared by recombinant methodologies known to persons skilled in the art. For example, a nucleic acid molecule comprising a nucleic acid sequence encoding the hemopexin protein (or a precursor thereof) can be transfected into a suitable host cell capable of expressing said nucleic acid sequence, incubating said host cell under conditions suitable for the expression of said nucleic acid sequence, and recovering said protein. Suitable methods for preparing a nucleic acid molecule encoding the recombinant hemopexin will also be known to persons skilled in the art, based on knowledge of the genetic code, possibly including optimizing codons based on the nature of the host cell (e.g. microorganism) to be used for expressing and/or secreting the recombinant hemopexin protein. Suitable host cells will also be known to persons skilled in the art, illustrative examples of which include prokaryotic cells (e.g., *E. coli*) and eukaryotic cells (e.g., *P. pastoris*, Chinese hamster ovary (CHO) cell lines CHO-K1 and CHO-S, as described in WO2016/054072; NS0 hybridoma cells and HEK293 cells, as described in WO2012/050874). Reference is made to "Short Protocols in Molecular Biology, 5th Edition, 2 Volume Set: A Compendium of Methods from Current Protocols in Molecular Biology" (by Frederick M. Ausubel (author, editor), Roger Brent (editor), Robert E. Kingston (editor), David D. Moore (editor), J. G. Seidman (editor), John A. Smith (editor), Kevin Struhl (editor), J Wiley & Sons, London). An illustrative example of recombinant hemopexin is described in WO2016/054072, the content of which is incorporated herein by reference.

In an embodiment disclosed herein, the hemopexin comprises, consists, or consists essentially of amino acid residues 24-462 of NCBI Reference Sequence NP_000604.1 (SEQ ID NO:1, below), or an amino acid sequence having at least 60%, 65%, 70%, 75%, 80%, 85%, 90%, 93%, 95%, 96%, 97%, 98% or 99% sequence identity thereto. It is to be noted that amino acid residues 1-23 of SEQ ID NO:1 (underlined text below) encode a signal sequence:

```
Human hemopexin precursor
                                             (SEQ ID NO: 1)
MARVLGAPVA LGLWSLCWSL AIATPLPPTS AHGNVAEGET

KPDPDVTERC SDGWSFDATT LDDNGTMLFF KGEFVWKSHK

WDRELISERW KNFPSPVDAA FRQGHNSVFL IKGDKVWVYP

PEKKEKGYPK LLQDEFPGIP SPLDAAVECH RGECQAEGVL

FFQGDREWFW DLATGTMKER SWPAVGNCSS ALRWLGRYYC

FQGNQFLRFD PVRGEVPPRY PRDVRDYFMP CPGRGHGHRN

GTGHGNSTHH GPEYMRCSPH LVLSALTSDN HGATYAFSGT

HYWRLDTSRD GWHSWPIAHQ WPQGPSAVDA AFSWEEKLYL

VQGTQVYVFL TKGGYTLVSG YPKRLEKEVG TPHGIILDSV

DAAFICPGSS RLHIMAGRRL WWLDLKSGAQ ATWTELPWPH

EKVDGALCME KSLGPNSCSA NGPGLYLIHG PNLYCYSDVE

KLNAAKALPQ PQNVTSLLGC TH
```

In another embodiment, the hemopexin is a human hemopexin comprising, consisting of, or consisting essentially of amino acid residues 24-462 of SEQ ID NO:1, or an amino acid sequence having at least 60%, 65%, 70%, 75%, 80%, 85%, 90%, 93%, 95%, 96%, 97%, 98% or 99% sequence identity thereto.

Reference to "at least 60%" includes 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity, for example, after optimal alignment or best fit analysis. Thus, in an embodiment disclosed herein, the hemopexin comprises, consists, or consists essentially of an amino acid sequence having at least 60%, preferably at least 65%, preferably at least 70%, preferably at least 75%, preferably at least 80%, preferably at least 85%, preferably at least 90%, preferably at least 93%, preferably at least 95%, preferably at least 96%, preferably at least 97%, preferably at least 98% or preferably at least 99% sequence identity to amino acid residues 24-462 of SEQ ID NO:1.

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e. resulting in the highest percentage homology over the comparison window) generated by any of the various methods selected. Reference also may be made to the BLAST family of programs as for example disclosed by Altschul et al. (1997) *Nucl. Acids. Res.* 25:3389. A detailed discussion of sequence analysis can be found in Unit 19.3 of Ausubel et al. (1994-1998) In: *Current Protocols in Molecular Biology*, John Wiley & Sons Inc.

The term "sequence identity" as used herein refers to the extent that sequences are identical or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, 1) or the identical amino acid residue (e.g. Ala, Pro, Ser, Thr, Gly, Val, Leu, lie, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For example, "sequence identity" is the "match percentage" calculated by the DNASIS computer program (Version 2.5 for windows; available from Hitachi Software Engineering Co., Ltd., South San Francisco, California, USA) using standard defaults as used in the reference manual accompanying the software.

The term "sequence identity", as used herein, includes exact identity between compared sequences at the nucleotide or amino acid level. This term is also used herein to include non-exact identity (i.e., similarity) at the nucleotide or amino acid level where any difference(s) between sequences are in relation to amino acids (or in the context of nucleotides, amino acids encoded by said nucleotides) that are nevertheless related to each other at the structural, functional, biochemical and/or conformational levels. For example, where there is non-identity (similarity) at the amino acid level, "similarity" includes amino acids that are nevertheless related to each other at the structural, functional, biochemical and/or conformational levels. In an embodiment, nucleotide and sequence comparisons are made at the level of identity rather than similarity. For example, leucine may be substituted for an isoleucine or valine residue.

This may be referred to as a conservative substitution. In an embodiment, the amino acid sequences may be modified by way of conservative substitution of any of the amino acid residues contained therein, such that the modification has no or negligible effect on the binding specificity or functional activity of the modified polypeptide when compared to the unmodified polypeptide.

Sequence identity with respect to the hemopexin, as herein described, relates to the percentage of amino acid residues in the candidate sequence that are identical with the residues of the corresponding peptide sequence after aligning the sequences and introducing gaps, if necessary, to achieve the maximum percentage homology, and not considering any conservative substitutions as part of the sequence identity. Neither N- or C-terminal extensions, nor insertions shall be construed as reducing sequence identity or homology.

Variants of hemopexin are also contemplated herein. As used herein, a "variant" of hemopexin is a molecule that shares at least some sequence identity with the amino acid sequence of a native (naturally-occurring) isoform of hemopexin (human or non-human), or a portion part thereof, yet still retains the ability to bind to heme. In some embodiments, the variant comprises, consists or consists essentially of an amino acid sequence having at least 60%, preferably at least 65%, preferably at least 70%, preferably at least 75%, preferably at least 80%, preferably at least 85%, preferably at least 90%, preferably at least 93%, preferably at least 95%, preferably at least 96%, preferably at least 97%, preferably at least 98% or preferably at least 99% sequence identity to amino acid residues 24-462 of SEQ ID NO:1.

In an embodiment disclosed herein, the variant is a heme-binding fragment of native hemopexin. A heme-binding fragments of hemopexin, also referred to interchangeably herein as a "binding fragment" or "heme-binding fragment", is a portion of the native hemopexin molecule (human or non-human) that retains at least part of the functional activity of the parent molecule to bind to heme. As noted elsewhere herein, heme binding can readily be determined by using methods known to persons skilled in the art, an illustrative example of which is the method described by Lipiski et al. (2013, *Antioxidants & Redox Signalling*, 19(14), pp. 1619-1633), the entire content of which is incorporated herein by reference. Slight modifications to the method by Lipiski et al. (2013) can also be used, as described elsewhere herein.

In an embodiment, the fragment of hemopexin comprises an intact heme-binding domain between the two four-bladed β-propeller domains, including amino acid residues His213 and His266, which have been described as coordinating the heme iron atom giving rise to a stable bis-histidyl complex.

It would be understood by persons skilled in the art that the binding affinity of the hemopexin (including variants thereof) for heme may vary depending on the amino acid sequence of the hemopexin (including a variant thereof). In an embodiment, the hemopexin, or heme-binding fragment thereof, binds to heme with a binding affinity having an equilibrium-dissociation constant ($K_D$) of $1\times10^{12}$ or less.

Also envisaged herein are fusion proteins comprising hemopexin, or a heme-binding fragment thereof. An illustrative example of a suitable fusion protein comprising hemopexin is described in WO2006/018428, the entire content of which is incorporated herein by reference.

The terms "at least partially purified", "isolated", "purified" and the like are used herein to mean that the hemopexin is provided in an isolated and/or purified form; that is, separated, isolated or purified from their natural environment, and are provided in a substantially pure or homogeneous form. Such proteins will typically be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo. For example, an at least partially purified hemopexin may comprise no more than 50% impurities (of total protein). Thus, in an embodiment disclosed herein, the purified hemopexin comprises, consists or consists essentially of no more than 50%, preferably no more than 45%, preferably no more than 40%, preferably no more than 35%, preferably no more than 30%, preferably no more than 25%, preferably no more than 20%, preferably no more than 15%, preferably no more than 10%, or preferably no more than 5% impurities (of total protein) or preferably no more than 1% impurities (of total protein).

In another embodiment disclosed herein, the hemopexin is provided in an isolated and/or purified form that is enriched, concentrated or otherwise has a specific activity, amount or concentration that is greater than the activity, amount or concentration of the hemopexin in the starting material from which it is derived. In an embodiment, the liquid formulation of purified hemopexin is derived from plasma.

Sodium Chloride

The present inventors have surprisingly found that the amount of sodium chloride that is incorporated into a liquid formulation of purified hemopexin is directly correlated with the stability of the hemopexin therein.

Reference to "at least 50 mM" includes 50 mM, 100 mM, 150 mM, 200 mM, 250 mM, 300 mM, 350 mM, 400 mM, 450 mM, 500 mM, 550 mM, 600 mM, 650 mM, and so on. Thus, in preferred embodiments of the present invention, the liquid formulation comprises at least 50 mM sodium chloride, at least 100 mM sodium chloride, at least 150 mM sodium chloride, at least 200 mM sodium chloride, at least 250 mM sodium chloride, at least 300 mM sodium chloride, at least 350 mM sodium chloride, at least 400 mM sodium chloride, at least 450 mM sodium chloride, at least 500 mM sodium chloride, at least 550 mM sodium chloride, at least 600 mM sodium chloride, at least 650 mM sodium chloride, and so on, including a range thereof.

In an embodiment disclosed herein, the liquid formulation comprises from about 50 mM to about 600 mM sodium chloride. In another embodiment, the liquid formulation comprises from about 150 mM to about 400 mM sodium chloride. In another embodiment, the liquid formulation comprises from about 150 mM to about 250 mM sodium chloride.

In an embodiment disclosed herein, the liquid formulation comprises 150 mM sodium chloride. In another embodiment, the liquid formulation comprises 400 mM sodium chloride.

Phosphate Buffer

The present inventors have surprisingly found that the type and amount of phosphate buffer that is incorporated into a liquid formulation of purified hemopexin is also has an impact on the stability of the hemopexin.

Suitable phosphate buffers will be familiar to persons skilled in the art, illustrative examples of which include sodium phosphate, potassium phosphate and citrate phosphate. The present inventors have unexpectedly found that citrate phosphate and sodium phosphate buffers perform better than potassium phosphate buffer, glycine buffer and Tris (Tris(hydroxymethyl)-aminomethane) buffers in stabilizing hemopexin in solution. Thus, in an embodiment disclosed herein, the phosphate buffer is selected from the group consisting of sodium phosphate, potassium phosphate and citrate phosphate. In a further embodiment disclosed herein, the phosphate buffer is selected from the group consisting of sodium phosphate and citrate phosphate.

In an embodiment, the phosphate buffer is sodium phosphate. In an embodiment, the sodium phosphate buffer comprises monobasic sodium phosphate and dibasic sodium phosphate.

The present inventors have unexpectedly found that citrate phosphate performs better than a sodium phosphate buffer in stabilizing hemopexin in solution. Thus, in another embodiment, the phosphate buffer is a citrate phosphate. In an embodiment, the citrate phosphate buffer comprises citric acid and dibasic sodium phosphate.

Reference to "at least 15 mM" includes 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 100 mM, 150 mM, 200 mM, 250 mM, 300 mM, 350 mM, 400 mM, 400 mM, and so on. Thus, in preferred embodiments of the present invention, the liquid formulation comprises at least 15 mM, at least 20 mM, at least 25 mM, at least 30 mM, at least 35 mM, at least 40 mM, at least 45 mM, at least 50 mM, at least 55 mM, at least 60 mM, at least 65 mM, at least 70 mM, at least 75 mM, at least 80 mM, at least 85 mM, at least 90 mM, at least 100 mM, at least 150 mM, at least 200 mM, at least 250 mM, at least 300 mM, at least 350 mM, at least 400 mM, at least 400 mM phosphate buffer, and so on, including a range thereof.

Whilst the present inventors have shown that a range of phosphate buffer and sodium chloride concentrations are useful for improving the stability of hemopexin in solution, they have also unexpectedly found that certain concentrations of phosphate buffer and certain concentrations of sodium chloride, when combined, provide optimal stability. In an embodiment disclosed herein, the liquid formulation comprises from 15 mM to 200 mM citrate phosphate and from 150 mM to 400 mM sodium chloride. In another embodiment, the liquid formulation comprises from 15 mM to 200 mM citrate phosphate and from 150 mM to 250 mM sodium chloride.

In another embodiment, the liquid formulation comprises 200 mM citrate phosphate and 150 mM sodium chloride. In another embodiment, the liquid formulation comprises 50 mM citrate phosphate and 400 mM sodium chloride. In yet another embodiment, the liquid formulation comprises 15 mM citrate phosphate and 150 mM sodium chloride.

In another embodiment disclosed herein, the liquid formulation comprises from 50 mM to 200 mM sodium phosphate and from 50 mM to 400 mM sodium chloride. In another embodiment disclosed herein, the liquid formulation comprises from 50 mM to 200 mM sodium phosphate and from 150 mM to 250 mM sodium chloride. In yet another embodiment disclosed herein, the liquid formulation comprises 200 mM sodium phosphate and 150 mM sodium chloride.

pH

The present inventors have also found that pH also plays a part in maintaining the stability of hemopexin in solution.

Reference to "pH from 5.8 to 8" includes 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 and 8.0. Thus, in preferred embodiments of the present invention, the liquid formulation comprises a pH of 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0.

In an embodiment disclosed herein, the pH of the liquid formulation is from 6.5 to 8.0. In an embodiment disclosed herein, the pH of the liquid formulation is from 7.0 to 7.6. In another embodiment disclosed herein, the pH of the liquid formulation is 7.2.

Suitable methods of determining and, where necessary, adjusting the pH of the liquid formulation will be familiar to persons skilled in the art. Preferably, the pH will be measured at room temperature.

Conductivity

The present inventors have also found that conductivity may contribute, at least in part, to the stability of hemopexin in solution. In an embodiment disclosed herein, the liquid formulation of purified hemopexin comprises a conductivity of at least 10 mS/cm. By "at least 10 mS/cm" means 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mS/cm and so on. In another embodiment, the liquid formulation of purified hemopexin comprises a conductivity of from 10 to 45 mS/cm.

Reference to a conductivity "from 10 to 45 mS/cm" includes 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 and 45 mS/cm.

In another embodiment disclosed herein, the conductivity of the liquid formulation is from 10 to 25 mS/cm. In yet another embodiment disclosed herein, the conductivity of the liquid formulation is from 15 to 25 mS/cm. In yet another embodiment disclosed herein, the conductivity of the liquid formulation is from 10 to 15 mS/cm. In a further embodiment disclosed herein, the conductivity of the liquid formulation is at least 30 mS/cm.

Suitable methods of determining and, where necessary, adjusting the conductivity of the liquid formulation will be familiar to persons skilled in the art, illustrative examples of which are described elsewhere herein. Preferably, conductivity is measured at room temperature.

Stabilisers

In some embodiments, the liquid formulations may further comprise a stabiliser. Suitable stabilisers will be known to persons skilled in the art, illustrative examples of which include amino acids, carbohydrates, salts, and/or detergents (e.g., non-ionic detergent). In some embodiments, the stabiliser comprises a mixture of a sugar alcohol and an amino acid. The stabilizer may comprise a mixture of a sugar (e.g. sucrose or trehalose), a sugar alcohol (e.g. mannitol or sorbitol), and an amino acid (e.g. proline, glycine and arginine). In a preferred embodiment, the formulation comprises an amino acid such as arginine. In other embodiments, the formulation comprises divalent metal ions in a concentration up to 100 mM and a complexing agent as described in U.S. Pat. No. 7,045,601.

In an embodiment disclosed herein, the liquid formulation further comprises a non-ionic detergent. Suitable non-ionic detergents will be familiar to persons skilled in the art, an illustrative example of which includes polysorbate 80 (Polyoxyethylene (20) sorbitan monooleate). The present inventors have found that the presence of polysorbate 80 in the liquid formulation of purified hemopexin improved the stability of the hemopexin therein. Thus, in an embodiment disclosed herein, the non-ionic detergent is polysorbate 80.

In an embodiment, the non-ionic detergent is present in an amount of at least 0.0005% v/v. Reference to "at least 0.0005% v/v" includes 0.0005%, 0.0006%, 0.0007%, 0.0008%, 0.0009%, 0.001%, 0.002%, 0.003%, 0.004%, 0.005%, 0.006%, 0.007%, 0.008%, 0.009%, 0.01%, 0.015%, 0.02%, 0.05%, 0.10%, 0.15% v/v and so on. Thus, in preferred embodiments of the present invention, the liquid formulation comprises at least 0.001% v/v, preferably at least 0.002% v/v, preferably at least 0.005% v/v, preferably at least 0.01% v/v, preferably at least 0.015% v/v, preferably at least 0.02% v/v, preferably at least 0.05% v/v, preferably at least 0.10% v/v, preferably at least 0.15% v/v and so on.

In an embodiment disclosed herein, the non-ionic detergent is present in an amount of less than 0.01% v/v.

In particular embodiments of the present invention, there is provided a stable liquid formulation of purified hemopexin comprising:
(a) a hemopexin content from 100 to 300 mg/mL;
(b) from 15 mM to 200 mM phosphate buffer;
(c) a pH from 6.5 to 8.0;
(d) from 150 mM to 400 mM sodium chloride; and
(e) optionally a non-ionic detergent in an amount of less than 0.02% v/v.

In a preferred embodiment the stable liquid formulation has a viscosity of less than 20 mPa*S when measured at 25° C.

In another preferred embodiment the stable liquid formulation has a hemopexin content of from 100 to 250 mg/mL and a viscosity of less than 20 mPa*S when measured at 25° C.

In particular embodiments of the present invention, there is provided a stable liquid formulation of purified hemopexin comprising:
(a) a hemopexin content from 100 to 300 mg/mL;
(b) from 15 mM to 200 mM phosphate buffer;
(c) a pH from 6.5 to 8.0;
(d) from 150 mM to 400 mM sodium chloride; and
(e) a non-ionic detergent in an amount of less than 0.02% v/v.

In a preferred embodiment the stable liquid formulation has a viscosity of less than 20 mPa*S when measured at 25° C.

In another preferred embodiment the stable liquid formulation has a hemopexin content of from 100 to 250 mg/mL and a viscosity of less than 20 mPa*S when measured at 25° C.

In particular embodiments of the present invention, there is provided a stable liquid formulation of purified hemopexin comprising:
(a) a hemopexin content from 100 to 300 mg/mL;
(b) from 15 mM to 200 mM citrate phosphate buffer;
(c) a pH from 6.5 to 8.0;
(d) from 150 mM to 400 mM sodium chloride; and
(e) optionally a non-ionic detergent in an amount of less than 0.02% v/v.

In a preferred embodiment the stable liquid formulation has a viscosity of less than 20 mPa*S when measured at 25° C.

In another preferred embodiment the stable liquid formulation has a hemopexin content of from 100 to 250 mg/mL and a viscosity of less than 20 mPa*S when measured at 25° C.

In particular embodiments of the present invention, there is provided a stable liquid formulation of purified hemopexin comprising:
(a) a hemopexin content from 100 to 300 mg/mL;
(b) from 15 mM to 200 mM citrate phosphate buffer;
(c) a pH from 6.5 to 8.0;
(d) from 150 mM to 400 mM sodium chloride; and
(e) a non-ionic detergent in an amount of less than 0.02% v/v.

In a preferred embodiment the stable liquid formulation has a viscosity of less than 20 mPa*S when measured at 25° C.

In another preferred embodiment the stable liquid formulation has a hemopexin content of from 100 to 250 mg/mL and a viscosity of less than 20 mPa*S when measured at 25° C.

In particular embodiments of the present invention, there is provided a stable liquid formulation of purified hemopexin comprising:
  (a) a hemopexin content from 100 to 300 mg/mL;
  (b) from 15 mM to 200 mM citrate phosphate buffer;
  (c) a pH from 7.0 to 7.6;
  (d) from 150 mM to 400 mM sodium chloride; and
  (e) optionally a non-ionic detergent in an amount of less than 0.02% v/v.

In a preferred embodiment the stable liquid formulation has a viscosity of less than 20 mPa*S when measured at 25° C.

In another preferred embodiment the stable liquid formulation has a hemopexin content of from 100 to 250 mg/mL and a viscosity of less than 20 mPa*S when measured at 25° C.

In particular embodiments of the present invention, there is provided a stable liquid formulation of purified hemopexin comprising:
  (a) a hemopexin content from 100 to 300 mg/mL;
  (b) from 15 mM to 200 mM citrate phosphate buffer;
  (c) a pH from 7.0 to 7.6;
  (d) from 150 mM to 400 mM sodium chloride; and
  (e) a non-ionic detergent in an amount of less than 0.02% v/v.

In a preferred embodiment the stable liquid formulation has a viscosity of less than 20 mPa*S when measured at 25° C.

In another preferred embodiment the stable liquid formulation has a hemopexin content of from 100 to 250 mg/mL and a viscosity of less than 20 mPa*S when measured at 25° C.

Stability

As noted elsewhere herein, purified hemopexin is inherently unstable in standard buffer solutions such as PBS. This introduces significant problems, in particular with storage of formulations over time. For example, as noted by the inventors' own data disclosed herein, purified hemopexin that is formulated in phosphate buffered saline (PBS; 10 mM sodium phosphate, 1.8 mM potassium phosphate, 137 mM NaCl, 2.7 mM KCl; pH 7.4) is relatively unstable, as determined by Differential Scanning Fluorimetry (DSF). In contrast to PBS, the inventors identified an unexpected and significant shift towards a higher Tm when hemopexin was formulated in sodium chloride and an alternative phosphate buffer such as citrate phosphate, sodium phosphate or potassium phosphate. This shift towards a higher Tm is indicative of stabilizing effect on the hemopexin.

Similarly, the inventors have found that, when purified hemopexin was formulated in PBS, there was significant degradation of hemopexin in solution over time, as evidenced by an increase in the amount of hemopexin aggregates (including hemopexin dimers) and hemopexin fragments. For instance, after storage at 37° C. for 3 months, a liquid formulation of hemopexin in PBS (pH 7.4) contained 54.6% w/w aggregates, 3.1% w/w dimers and 9.8% fragments of hemopexin, with only 32.5% w/w of hemopexin monomers remaining. This was also reflected by a loss of heme binding activity. By contrast, when purified hemopexin is formulated in a solution of NaCl in combination with an alternative phosphate buffer of at least 15 mM (e.g., such as citrate phosphate or sodium phosphate) and stored at 37° C. for the same period of time, there was a significant reduction in the proportion of hemopexin aggregates and fragments in the solution, with greater than 50% hemopexin monomers remaining in the solution. This was also reflected in the preservation of heme binding, denoting a significant stabilizing effect on hemopexin. In an embodiment disclosed herein, the concentration of monomeric hemopexin in solutions comprising NaCl and phosphate buffer is at least 75%, at least 80%, at least 90% or at least 95% by weight of total protein, as measured by size exclusion HPLC.

Preferably, the liquid formulation disclosed herein will retain substantially its original stability characteristics for at least 2, 3, 4, 5, 6, 7, 8, 9, 10, 12, 18, 24, 36 or more months. For example, liquid formulations stored at 2-8° C. or 25° C. will typically retain substantially the same molecular size distribution as measured by HPLC-SEC, or retain substantially the same hemopexin monomer content when stored for 1 month or longer. Particular embodiments of the liquid formulation can be stable and suitable for commercial pharmaceutical use for at least 3 months or even longer when stored at 2-8° C. and/or 25° C. room temperature.

In an embodiment disclosed herein, the liquid formulation comprises at least 70% hemopexin monomers when stored at 37° C. for 1 month.

In an embodiment disclosed herein, the liquid formulation comprises at least 50% hemopexin monomers when stored at 37° C. for 2 months.

In an embodiment disclosed herein, the liquid formulation comprises at least 50% hemopexin monomers when stored at 37° C. for 3 months.

In an embodiment disclosed herein, the liquid formulation comprises at least 80% hemopexin monomers when stored at 37° C. for 1 month.

In an embodiment disclosed herein, the liquid formulation comprises at least 70% hemopexin monomers when stored at 37° C. for 2 months.

In an embodiment disclosed herein, the liquid formulation comprises at least 60% hemopexin monomers when stored at 37° C. for 3 months.

The liquid formulations disclosed herein may be formulated with a pharmaceutically acceptable carrier. Suitable pharmaceutically acceptable carriers, diluents and/or excipients are known to those skilled in the art. Examples include solvents, dispersion media, antifungal and antibacterial agents, surfactants, isotonic and absorption agents and the like.

The formulation may also be sterilised by filtration prior to dispensing and long term storage. The compositions described herein may be formulated into any of many possible dosage forms such as injectable formulations. The formulations and their subsequent administration (dosing) are within the skill of those in the art. Dosing is dependent on the responsiveness of the subject to treatment, but will invariably last for as long as the desirable effect (e.g., a reduction in the level of heme) is desired. Persons of ordinary skill can easily determine optimum dosages, dosing methodologies and repetition rates.

In another aspect of the present invention, there is provided a method for determining the heme binding activity of hemopexin in a liquid formulation, the method comprising:
  (a) providing a complex of heme and a heme carrier molecule;
  (b) mixing the complex of (a) with a liquid formulation comprising hemopexin and incubating the admixture for a period of time to allow the heme to transfer from the carrier molecule to the hemopexin; and (c) measuring the absorbance of the admixture of (b) at two or more wavelengths selected from the range of 450 nm to 700 nm, wherein the difference between the absorbance values at the two or more wavelengths as measured in (c) is indicative of the heme binding activity of the hemopexin in the liquid formulation.

This aspect of the present disclosure is predicated on the inventors' findings that the different spectral characteristics of heme when it is bound to albumin or to hemopexin can be used to determine the concentration of the heme-hemopexin complex in the solution and, hence, the heme binding activity of hemopexin. In an embodiment, a molar excess of a heme-carrier molecule complex is mixed with a liquid formulation comprising hemopexin (diluted in an appropriate buffered solution such a phosphate buffered saline, if necessary) and the admixture is incubated for a period of time to allow the transfer of heme from the heme-carrier protein to the hemopexin. The absorbance of the mixture is then measured at a minimum of two wavelengths in the visible spectrum. Beer's Law can then be used with extinction coefficients for heme bound to the carrier molecule and to the hemopexin and the measured absorbance values to calculate the concentration of the resulting heme-hemopexin complex. This concentration is typically corrected for any dilutions of the original hemopexin solution performed during the assay, and the resulting concentration corresponds to the amount of active hemopexin in the original liquid formulation. The heme carrier molecule will typically bind heme with a lower affinity than hemopexin and is generally capable of binding heme in an aqueous environment. Suitable examples of heme carrier molecules will be familiar to persons skilled in the art, illustrative examples of which include haemoglobin and albumin. Thus, in an embodiment disclosed herein, the heme carrier molecule is selected from the group consisting of haemoglobin and albumin. It would be understood by persons skilled in the art that the heme carrier molecule may be a naturally-occurring molecule (e.g., a serum-derived heme carrier such as haemoglobin or albumin) or it may be non-naturally-occurring (e.g., a recombinantly produced carrier molecule such as human recombinant albumin). In an embodiment, the heme carrier protein is albumin. More preferably, the heme carrier protein is human albumin. Advantages of using albumin include (i) it is readily available, (ii) it is a physiologically relevant heme carrier in plasma, (iii) it is known to transfer heme to hemopexin, and (iv) it forms a defined 1:1 complex with heme (see Ascenzi & Fasano, 2009, *Life*, 61(12) 1118-1122).

A minimum of two wavelengths is required that exhibit an absorbance change when heme is transferred from the carrier molecule to the hemopexin. In an embodiment, the two or more wavelengths are selected such that absorbance at one wavelength will increase and the absorbance at the other wavelength will decrease. It is expected that the greater the magnitude of change of absorbances between the two or more wavelengths, the greater the sensitivity of the method in determining heme binding activity. Wavelengths near a peak or valley in the mixture spectrum, and not on a steep slope, are preferred and can make the method more tolerant to errors in spectrophotometer calibration. Reference herein to "450 nm to 700 nm" includes 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm and 700 nm. In the visible spectrum, heme bound to albumin has absorbance peaks at about 500 nm, 533 nm and 622 nm, while heme bound to hemopexin has absorbance peaks at about 533 nm and 565 nm. Thus, in an embodiment disclosed herein, the two or more wavelengths are selected from the range of 500 nm to 630 nm. In a preferred embodiment, the two or more wavelengths are selected from the group consisting of 500 nm, 533 nm, and 622 nm. In a further embodiment, the two or more wavelengths are 533 nm and 622 nm. Absorbance at 622 nm has the advantage over 500 nm (both of which exhibit the same direction of change) due to the higher magnitude of the change in absorbance as heme transferred from albumin to hemopexin.

Based on the absorbance of the heme transfer mixture and the extinction coefficients of heme-albumin and heme-hemopexin at these wavelengths, the concentration of the heme-hemopexin complex can be calculated. The amount of heme-hemopexin determined in the final mixture represents the amount of biologically active hemopexin. The incubation time and temperature are typically chosen to allow transfer of heme from the heme binding molecule to the hemopexin in the solution. The method is typically performed so that there is a significant excess of heme-albumin relative to hemopexin (approximately 2.5×) to ensure that there is sufficient heme to fully saturate all active hemopexin molecules. In an embodiment disclosed herein, the incubation is conducted at 20-25° C. or 37° C. for about 5 to 60 minutes. In a preferred embodiment, the incubation is conducted at 37° C. for 10 to 20 minutes. The pH and buffer concentration of the admixture are typically selected to allow the heme carrier molecule to transfer heme to the hemopexin. In a preferred embodiment, the pH is close to physiological conditions; that is, from about pH 6.5 to 7.5. In an embodiment, the pH is 7.0. The concentration of the heme binding molecule and the hemopexin is selected such that the total absorbance at the two or more wavelengths is in the linear range of the spectrophotometer. The method can be set up such that there is a significant excess amount of heme-carrier molecule relative to hemopexin (e.g., about 2.5-fold) to ensure that there is sufficient heme to fully saturate all active hemopexin molecules in the admixture.

In an embodiment disclosed herein, the liquid formulation comprises at least 90% hemopexin with heme binding activity when stored at 2-8° C. for 6 months.

In an embodiment disclosed herein, the liquid formulation comprises at least 90% hemopexin monomers when stored at room temperature (e.g., 25° C.) for 6 months.

In an embodiment disclosed herein, the liquid formulation comprises at least 50% hemopexin monomers when stored at 37° C. for 6 months.

Methods of Treatment

In another aspect of the present invention, there is provided a method of treating a condition associated with haemolysis, the method comprising administering to a subject in need thereof a composition comprising, consisting or consisting essentially of the stable liquid formulation of purified hemopexin, as disclosed herein.

The term "subject", as used herein, refers to an animal which includes a primate (for example, a lower or higher primate). A higher primate includes human. Whilst the present invention has particular application to targeting conditions in humans, it would be understood by those skilled in the art that non-human animals may also benefit from the compositions and methods disclosed herein. Thus, it will be appreciated by the skilled art that the present invention has both human and veterinary applications. For convenience, an "animal" includes livestock and companion animals such as cattle, horses, sheep, pigs, camelids, goats, donkeys, dogs and cats. With respect to horses, these include horses used in the racing industry as well as those used recreationally or in the livestock industry.

The compositions or formulations of the present invention may be administered to the subject a number of ways. Examples of suitable routes of administration include intravenous, subcutaneous, intra-arterial or by infusion. In an embodiment, the compositions or formulations are administered intravenously. In another embodiment, the compositions or formulations are administered subcutaneously.

Where necessary, the methods of the present invention may further comprise administering a second therapeutic agent. The second therapeutic compound may be co-administered to the subject sequentially (before or after administration of the compositions or formulations disclosed herein) or concurrently. In an embodiment, the second therapeutic agent is an iron chelating agent (e.g., deferoxamine or deferiprone).

In another aspect of the present invention, there is provided use of the compositions or formulations of the present invention, as disclosed herein, in the manufacture of a medicament for treating a condition associated with haemolysis. Such compositions or formulations are preferably suitable for use in human patients.

In another aspect of the present invention, there is provided the compositions or formulations of the present invention, as disclosed herein, for use in treating a condition associated with haemolysis in a subject in need thereof.

Conditions associated with haemolysis and which are at risk of haemoglobin/heme-mediated toxicity are known in the art. In an embodiment, the condition is selected from an acute haemolytic condition and/or a chronic haemolytic condition. In an embodiment, the condition is selected from the group consisting of haemolytic anaemia, aplastic crisis, hyper-haemolytic crisis, transfusion-induced haemolysis, haemolytic uraemic syndrome, myocardial infarcts, acute chest syndrome, pulmonary hypertension, leg ulcers, growth retardation, bone infarcts, pre-eclampsia, renal failure, acute kidney injury, acute respiratory distress syndrome (ARDS), stroke including haemorrhagic stroke, intra-cranial haemorrhage (ICH), splenic sequestration, splenic infarcts, an autoimmune disease (e.g., autoimmune haemolytic anaemia), microbial infection or increased susceptibility to infection (e.g., malaria infection), trauma, a transplant related condition, open heart surgery using cardiopulmonary bypass, and burns, including in the treatment of haemoglobinemia or haemoglobinuria accompanied with haemolysis after burn.

In an embodiment, the condition is selected from the group consisting of sickle cell anaemia, hereditary spherocytosis, hereditary elliptocytosis, thalassemia, congenital dyserythropoietic anemia and paroxysmal nocturnal haemoglobinuria (PNH), systemic lupus erythematosus and chronic lymphocytic leukemia.

In an embodiment, the condition is selected from the group consisting of haemorrhagic stroke and intra-cranial haemorrhage (ICH).

In an embodiment, the condition is a genetic or hereditary disease or disorder that causes haemolysis and inflammation.

In an embodiment, the condition is ARDS.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Material and Methods

A. Sample Preparation

For the reported formulation development, hemopexin (Hpx) was purified from human plasma (Kistler-Cohn Fraction IV) in Kankakee. Purification process details were based on the processes previously described in WO2014/055552, the contents of which are incorporated herein by reference in their entirety. Purified Hpx was provided in PBS, pH 7.4, at a protein concentration of 3-4%.

Protein concentration of the formulations was determined by measuring the UV-absorbance at 280 nm with a Cary60 spectrophotometer (Agilent). Briefly, the protein solution was diluted in NaCl 0.9% to a concentration that is within the accurate range of the instrument (<1.5 mg/mL) and placed into a UV-Vis disposable cuvette (path length: 1 cm). The measured absorption was converted according the Beer-Lambert law using extinction coefficient of 1.971: $A=\varepsilon \times c \times l$, where c is the concentration, l is the path length of the cuvette (cm), $\varepsilon$ is the extinction coefficient (0.1% at 280 nm; 1 cm path length) and A is the absorbance at a given wavelength. Protein concentration was expressed as average mg/mL from two independent measurements.

For DSF experiments, Hpx was diluted into the buffers/excipients of investigation to a final concentration of 0.1 mg/mL. Higher concentrated (up to 35%) Hpx formulations for stress induced stability studies were obtained by diafiltration with an Äkta flux device (GE Healthcare) using a 10 kDa MW cut-off filtration cassette (PES, 50 cm$^2$, PALL Life Sciences).

TABLE 1a

Overview of stability tests described in this report

| Stability Study | Hpx Batch | Storage conditions | Protein g/L | Excipients analyzed |
|---|---|---|---|---|
| Thermal and physical stress induced stability studies | | | | |
| I | TO271228 | Temperature Ramp (DSF) | 0.1 g/L | Buffer screening I |
| II | TO271228 | Temperature Ramp (DSF) | 0.1 g/L | Buffer screening II |

TABLE 1a-continued

Overview of stability tests described in this report

| Stability Study | Hpx Batch | Storage conditions | Protein g/L | Excipients analyzed |
|---|---|---|---|---|
| III | TO271228 | Temperature Ramp (DSF) | 0.1 g/L | Sugars |
| IV | TO271228 | Temperature Ramp (DSF) | 0.1 g/L | Salt (NaCl) |
| V | TO271228 TO294063 | Temperature Ramp (DSF) | 0.1 g/L | Ionic strength |
| VI | TO271228 TO294063 | Temperature Ramp (DSF) | 0.1 g/L | citrate phosphate |
| VII | TO271228 | Agitation and freeze/thaw cycles | 100 g/L | Polysorbate 80 |

(Accelerated) Stability studies (3-24 months)

| | | | | |
|---|---|---|---|---|
| 1 | TO271204 | 37° C., RT, 2-8° C. | 100 g/L | several buffers, 150 mM NaCl |
| 2 | TO271228 | 37° C., RT | 100 g/L | Polysorbate 80 |
| 3 | TO294063 | 37° C., RT, 2-8° C. | 100 g/L | several buffers, different NaCl concentrations |
| 4 | TO294063 | 37° C., RT | 100 g/L | Polysorbate 80 |
| 5 | TO29010/ TO294001 + TO294023 | 37° C., RT, 2-8° C. | 100 g/L | 200 mM citrate buffer, pH 7.2, different NaCl concentrations |
| 7 | TO294267 + TO318001 | 37° C., RT, 2-8° C. | 100 g/L | Different combinations of citrate phosphate buffer and NaCl |

C. Differential Scanning Fluorimetry (DSF)

Figure 1:
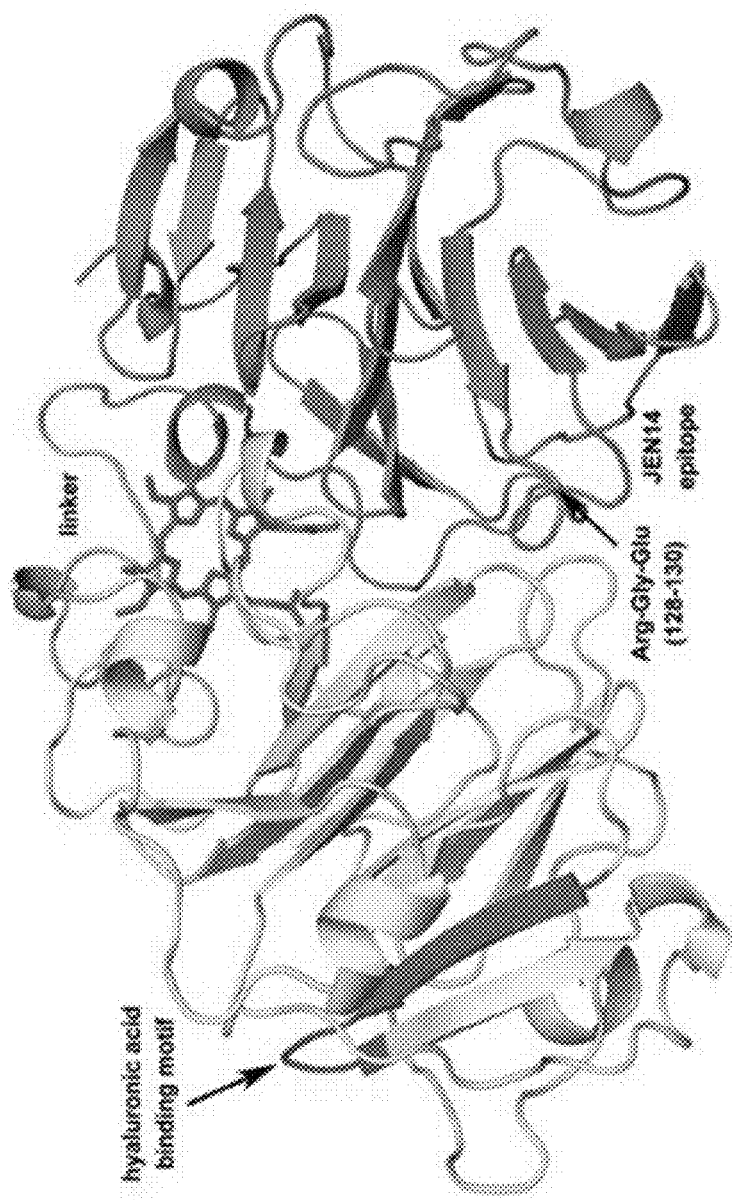
FIG. 1 is a diagrammatic representation of the structure of the heme-hemopexin complex, showing the β-propeller C-domain (light grey), the N-domain (dark grey), the linker sequence, and heme. The hyaluronic acid binding motif [348-358 (dark grey)] located in the β-propeller C-domain, the Arg-Gly-Glu sequence [128-130 (arrow)] at the interface of the N- and C-domains, and the location of the JEN14 epitope is also indicated.
Figure 2:
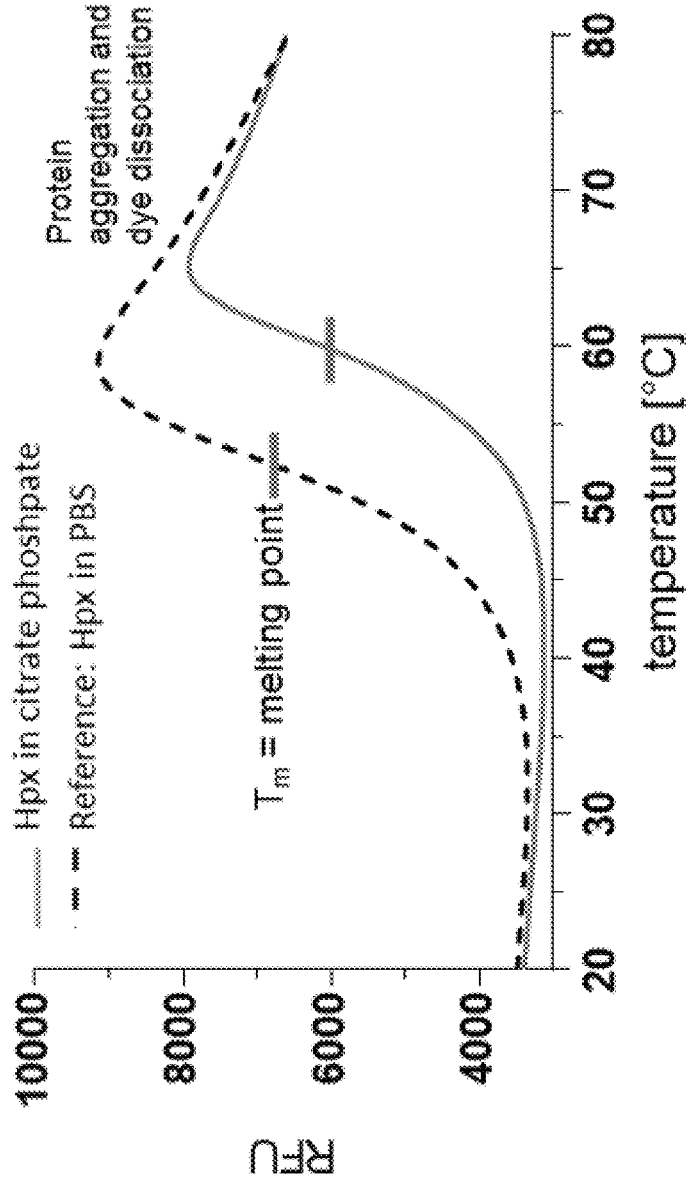
FIG. 2 shows a typical recording of relative fluorescence intensity (RFU) versus temperature for the unfolding of protein in the presence of SYPRO orange. $T_m$ is determined by the midpoint of the melt curve (grey horizontal bar). Hpx formulated in PBS, pH 7.4 (dashed line, $T_m$=53.0 C) and Hpx formulated in citrate phosphate, pH 7.4 (solid line, $T_m$ 60.5° C.) are shown.

Differential scanning fluorimetry (DSF) is a rapid method to investigate thermal stability of purified proteins in the presence of different stabilizers and excipients. The temperature at which a protein unfolds is measured by an increase in the fluorescence of a dye with affinity for hydrophobic parts of the protein, which are exposed as the protein unfolds. An assay protocol by Niesen et al. (Niesen, 2007) was adapted and modified accordingly. Briefly, purified Hpx (approx. 4%) was diluted into the desired buffers in presence of different excipients to a final protein concentration of 0.1 mg/mL. The samples were distributed into the wells of a PCR plate, by adding 20 µL 0.1 mg/mL protein and 0.5 µL of SYPRO Orange (pre-diluted 1:400 in PBS). Each condition was measured in triplicates. The plate was sealed with an optical foil and spun down shortly to collect all solution at the bottom of the wells. Temperature ramps from 25 to 80° C. (at 0.5° C./min) were performed on a CFX96 Real-Time PCR System (BioRad) and excitation and emission wavelengths were set to 492 and 610 nm, respectively. Data collection was performed with the CFX Manager™ Software (BioRad). Through unfolding of the protein with increasing temperature, strong fluorescent light at 610 nm was emitted by the dye binding to the newly exposed hydrophobic patches. In this way, a melting curve for each condition was generated as illustrated in FIG. 2. After peaking, the fluorescence intensity gradually decreased, which is mainly explained by protein being removed from solution owing to precipitation and aggregation. The sigmoidal ascending curve of the peak could be described by a two-state transition and the inflection point of each melting curve was used for the determination of the $T_m$ ($1^{st}$ derivation). To identify buffer conditions that (de)stabilize Hpx, the $T_m$ value of the protein under each condition of the screen was compared with the reference $T_m$ (Hpx in PBS, pH 7.4).

D. Heme Binding Assay I

Heme binding was measured by an adaptation of the method previously described by Lipiski (2013; Human Hp1-1 and Hp2-2 Phenotype-Specific Haptoglobin Therapeutics Are Both Effective In Vitro and in Guinea Pigs to Attenuate Haemoglobin Toxicity. *Antioxidants & Redox Signalling*, 19(14), pp. 1619-1633). Briefly, either met-Hb ($Fe^{3+}$) (15 µM in PBS) or hemin bound to human albumin (25 µM in PBS) was incubated with 10 µM human Hpx. Serial UV-VIS spectra were recorded (350-650 nm) using a Cary 60 UV-VIS Spectrophotometer (Agilent Technologies) in order to follow the transition of met-Hb/hemin to heme-Hpx over time. For each time-point, the concentrations of met-Hb/hemin and heme-Hpx in the reaction mixtures were resolved by deconvolution of the full spectrum by applying Lawson-Hanson's Non Negative Least Squares algorithm of SciPy (www.scipy.org). Deconvolution scripts were provided by UZH (J. Deuel and D. Schaer). After reaching the plateau, at least 15 data points were averaged and expressed as amount of transferred heme in µM. Hpx activity was expressed in percentage as the amount of heme/hemin binding Hpx compared to the total amount of Hpx initially applied.

E. Heme Binding Assay II

The following is an alternative assay for measuring the amount of active hemopexin in a solution.

Hemopexin binds hemin (also known as ferriheme, consisting of protoporphyrin IX containing iron(II) with a chloride ligand, the fully oxidized form of heme) with the highest affinity of any known protein and is able to compete for hemin which is bound to albumin. Hemin has a characteristic strong absorption band in the Soret region, as well as less intense bands in the visible region of the spectra. The absorbance maxima of those bands shifts depend on the oxidation and ligand binding state of hemin in solution. Free hemin has an absorbance maximum at 385 nm, which can be used for accurate concentration determination of free hemin in solution. In the visible range, the spectrum of hemin bound to albumin has peaks with maxima at 500 nm, 533 nm and 622 nm, while the spectrum of hemin bound to hemopexin has peaks maxima at 533 nm and 565 nm. In this method, purified hemopexin is added to excess amounts of a heme-albumin complex, and spectrophotometry is used to measure the absorbance change during the hemin transfer from albumin to hemopexin at 533 nm and 622 nm. Based on the absorbance of the hemin transfer mixture and the extinction coefficients of heme-albumin and heme-hemopexin at the above mentioned wavelengths, the concentration of the heme-hemopexin complex can be calculated. The amount of heme-hemopexin determined in the final mixture corresponds to the amount of active hemopexin.

Abbreviations

CV Coefficient of Variation
Hpx Hemopexin
PBS Phosphate buffered saline
PVDF Polyvinylidene fluoride
Q.S. Quantum satis
SOP Standard operating procedure
UV Ultraviolet
Vis Visible Materials and Equipment:
Hemin: Frontier Scientific H651-9.
Purified human albumin: i.e., CSLB Albuminar 25% or AlbuRx 25%.
Hemopexin control and samples for testing.
PBS pH 7.4: ThermoFisher 28348 20× concentrate or equivalent.
Phosphoric acid: Fisher A260-500, 85 wt % (equals 14.62 M).
Water: Fisher W5-4, HPLC grade or better.
Disposable UV Cuvette: 1.5 mL, semi-micro (12.5×12.5× 45 mm) Cat No.: 7591 65, BRAND GmbH, 1 cm path length.
0.22 µm PVDF syringe filters (Millipore SLGV033RS, low protein binding Durapore or equivalent).
UV-Vis spectrophotometer equipped with thermostated multi-cell changer (or equivalent).
Calibrated adjustable pipettes.
Calibrated pH meter.

Procedure (i) Buffer Preparation

5 M phosphoric acid solution: slowly add 3.42 mL of 85 wt % phosphoric acid to 2.5 mL deionized water. 1×PBS: Dilute 20×PBS concentrate in deionized water for 1×PBS.

(ii) Preparation of Heme-Albumin Complex

Approximately 66 mg of hemin was dissolved and Q.S. to 10 mL in a volumetric flask using 0.1 M NaOH, incubated at 37° C. for 3 minutes and adjusted to a final concentration of about 10 mM. To determine the concentration of the hemin stock solution, 10× serial dilutions were performed thrice by adding 500 µL of hemin solution in 4500 µL of 5 mM NaOH, such that the final dilution factor was 1000 with a hemin concentration of about 10 µM. The UV-Vis spectrophotometer was zeroed with 5 mM NaOH and absorbance of the diluted solution was read at $A_{385}$ and the actual concentration (mM) for the hemin stock was calculated using Equation 1, below. The hemin extinction coefficient in 5 mM NaOH is 58400 M$^{-1}$ cm$^{-1}$ (Kirschner-Zilber et al., 1982; Biochimica et Biophysica Acta 690:20-30).

$$C_{stock\ hemin\ from\ Step\ (ii)\ above} = A_{385} \div 58400 \times 10^6 \quad \text{Equation 1}$$

Approximately 2.5 mL of the stock hemin solution was diluted to 10 mL (4× dilution, approximately 2.5 mM) using 0.1 M NaOH. Mix 8 mL 25% albumin, 2 mL of HPLC grade water and 10 mL of 2.5 mM hemin in 0.1 M NaOH solution and then incubated at 37° C. for 1 hr. The pH was adjusted to 7.4 with 5 M phosphoric acid (~80-100 µL was required). In a volumetric flask, the diluted solution was Q.S. to 25 mL using HPLC grade water or better, then passed through a 0.22 µm filter and aliquoted to 0.5 mL for subsequent storage at −80° C., as required. The final concentration of albumin was around 1.21 mM (based on 66 kDa, 80 mg/mL). The final concentration of the heme-albumin complex equals the calculated stock hemin concentration from Equation 1, above, divided by the total dilution factor of 10.

(iii) Hemopexin Testing Sample Dilution

Hemopexin solutions were diluted using calibrated adjustable pipettes to approximately 10 mg/mL hemopexin in PBS.

(iv) Hemopexin Assay Control

A hemopexin assay control is a hemopexin sample with an established (known) functional activity. When analyzing hemopexin testing samples, the assay control is included in each assay. To establish the activity value of a hemopexin control sample, the heme transfer assay described above can be performed at least three times on different days on the control sample. The % CV of different repeats will ideally be within 10%, otherwise repeat the assay with freshly made buffer and reagent.

(v) Heme Transfer from Albumin to Hemopexin

In a plastic cuvette, 250 µL of heme-albumin solution was mixed with 600 µL of 10 mg/mL hemopexin testing sample or assay control, and 1150 µL PBS. Mixtures for each sample were then prepared in triplicate using a single hemopexin dilution, as outlined above. The mixtures were incubated at 37° C. for 10-20 min and absorbance values on the UV-Vis spectrophotometer were measured using the Advanced Reads Mode and 18-cell holder. The spectrophotometer was zeroed with PBS before measurement. The following settings were used:

Wavelengths: 533 nm, 622 nm and 700 nm. Average Time: 1 sec. Cuvette temperature: 37° C.

(vi) Calculation, Data Analysis and Acceptance Criteria

Absorbance values at 700 nm are typically kept below 0.1 AU to ensure minimal light scattering interference of the readings. The concentration of heme-hemopexin (i.e. total active hemopexin) was then calculated for each transfer reaction using Equation 2, below. The calculated concentrations of hemopexin are reported in units of µM and the cuvettes had a path length (t) of 1 cm:

$$c_{Hx} = (99.19)\frac{A_{533}}{\ell} - (143.0)\frac{A_{622}}{\ell} \quad \text{Equation 2}$$

The result was then multiplied by the dilution factor to determine the active hemopexin concentration in the original solution. The triplicates of each sample were then averaged. The average active hemopexin concentration for the assay control should typically be within 10% of the value previously established for that batch of assay control.

F. Methods for Stability Assessment and Indicative Protein Characterization

Table 2 summarizes all other assays and procedures, which were used for further investigation of Hpx stability and protein characterization.

TABLE 2

Assays to assess Hemopexin stability and characterization

| Assay | Unit | Methods | Procedure (SOP) |
|---|---|---|---|
| Molecular size distribution | % | SEC-HPLC | Analogous to BRN-TEI-0000165 Column: Diol 300, Flow 0.5-1.0 mL/min |
| IEF and size distribution | — | 2D PAGE | laboratory protocol |
| Protein distribution | — | SDS-PAGE | Analogous to BRN-TEI-0000274 |
| Protein | g/L | Biuret | BRN-TEI-0000265 |
| Protein | g/L | A280 | laboratory protocol |
| Viscosity | mPa*s | Rheometer | laboratory protocol |
| Dynamic light scattering | — | DLS | laboratory protocol |
| Static light scattering | — | SEC-MALS | laboratory protocol |

Figure 3:
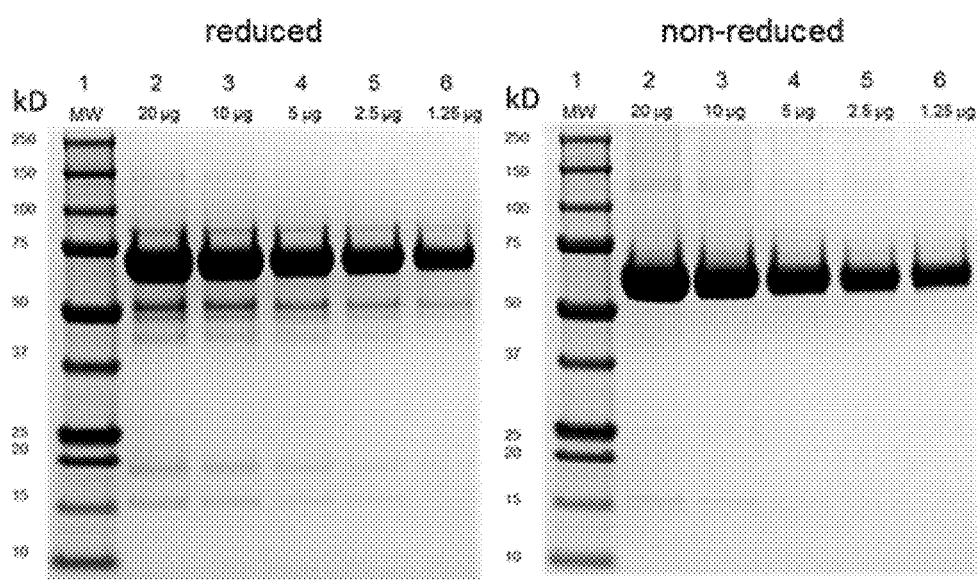
FIG. 3 shows the biochemical characterization of human plasma-derived hemopexin (Hpx). A: SDS-PAGE analysis of Hpx batch TO290016 (20-1.25 µg) under reducing and non-reducing conditions. MW marker was loaded in lane 1 for both conditions; the bands were visualized by Coomassie Staining (SimplyBlue; Invitrogen); B: 2D-PAGE analysis: hemopexin samples (5 µg) were separated by immobilized pH gradient strips (pI 3-10, Invitrogen) followed by SDS polyacrylamide gel electrophoresis. The spots were visualized by colloidal blue staining (SimplyBlue; Invitrogen), the multiple bands of Hpx are marked within the box; C: Molecular size distribution of 10% untreated (solid line) and aged Hpx ("aged", 3 months at 37° C.; dashed line), analyzed by SEC-HPLC (Column: YMC Pack Diol-300, 5 µm, 300×8 mm). Molar mass of each species was determined in-line with a MALS (Dawn HELEOS, Wyatt Technologies) and RI detector (Optilab T-rEX, Wyatt Technologies) (light grey line); D: Different concentrations of hemopexin (formulated in PBS, pH 7.4) and the corresponding viscosities were plotted and compared to a viscosity curve of polyclonal IgG (triangles). Viscosity measurements were performed in duplicates on a rotational rheometer at 25° C. (HAAKE, ThermoScientific).
Figure 3:
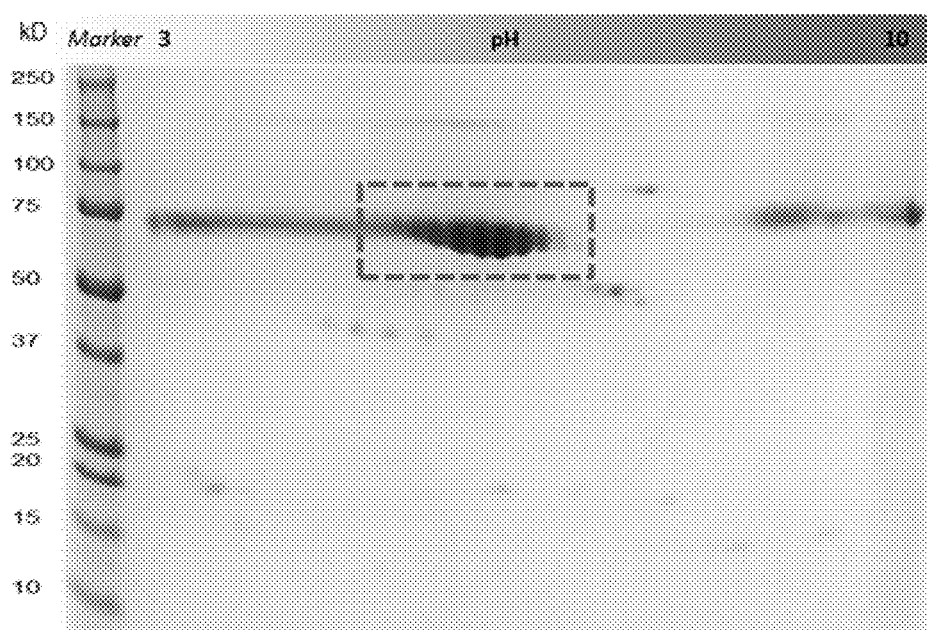
Figure 3:
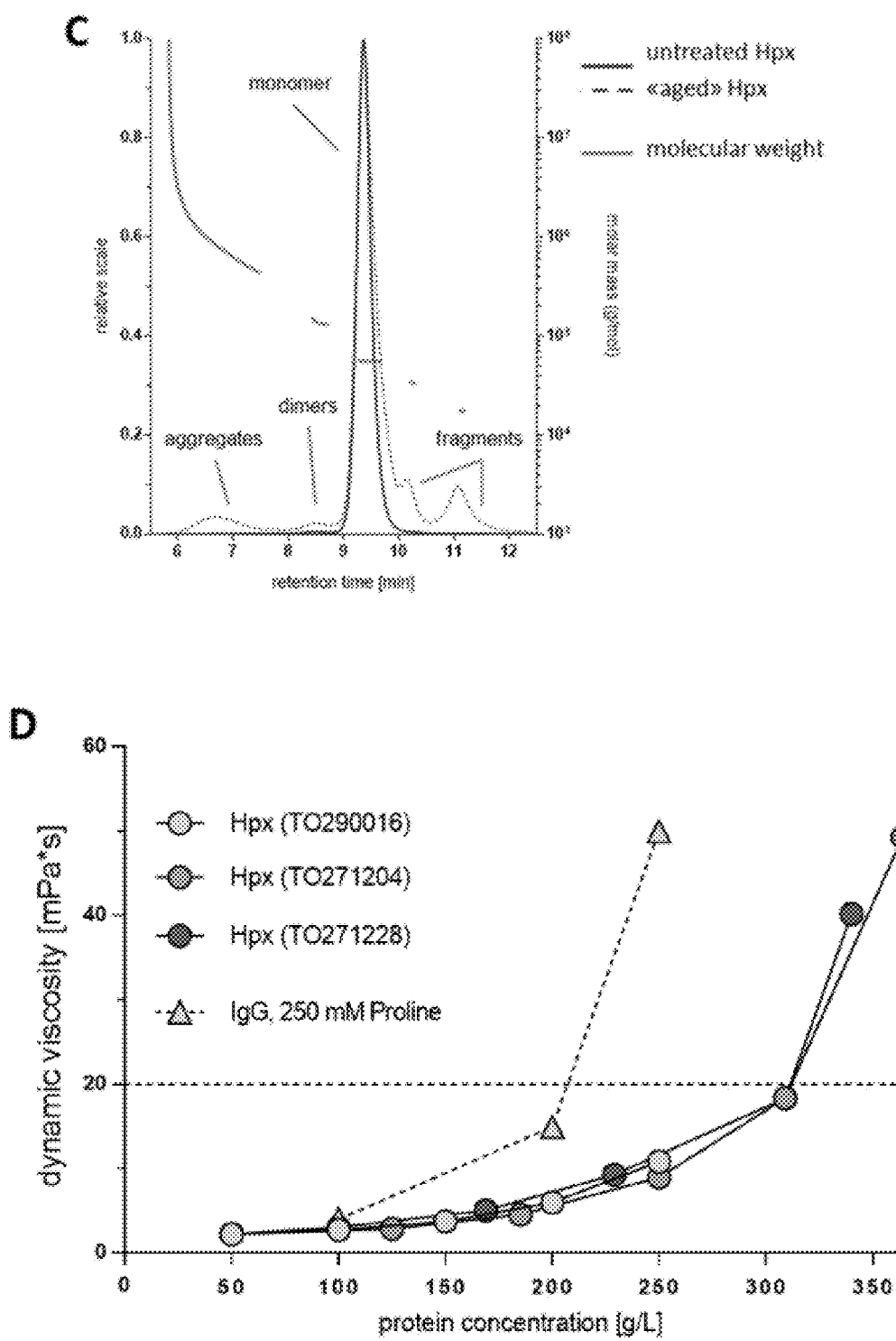

Example 1. Biochemical Characterization of Purified (PBS-Formulated) Human Hemopexin In a first approach, purified PBS-formulated Hpx was analyzed by several biochemical methods to set the analytical benchmarks (reference values). SDS-PAGE and SEC-HPLC data demonstrated protein purity of >98% for purified Hpx (FIG. 3). As shown before by others (Mauk, 2011) Hpx exhibited an increased molecular weight under reducing (approx. 65-70 kDa) compared to the non-reducing conditions (approx. 60 kDa) (FIG. 3A). The molecular size distribution by SEC-HPLC, revealed one main peak, which corresponds to monomeric Hpx with a molar mass of 57 kDa (confirmed by SLS measurement, FIG. 3C). In aged and heat-stressed samples, two distinct fragment peaks could be identified (32-35 kDa and 17-20 kDa) and two peaks corresponding to higher molecular weight species, one of which was identified as a Hpx-dimer (130-138 kDa). The second peak corresponded to an even higher molecular weight, reflecting the higher polymers or aggregates.

Further, by isoelectric focusing, the theoretical isoelectric point at pH 6.55 could be confirmed (approx. pH 6) as shown in FIG. 3B, and multiple Hpx bands could be attributed to carbohydrate variability, especially the extent of sialylation as described by Mauk, 2011. 2D-PAGE analysis revealed only a minor amount of impurities.

At last, human hemopexin was concentrated (formulated in PBS, pH 7.4) up to 350 g/L (35%) and samples were taken intermittently to analyze solution viscosity at the corresponding protein concentration (FIG. 3D). As shown below, up to a concentration of 300 g/L the viscosity remained below 20 mPa*s, which is considered as a permissive viscosity for any delivery system (Du, 2011; *Biotechnology and Bioengineering*, pp. 632-636).

Example 2. Buffer Screening

Several buffer candidates were defined and the screening for optimal buffer conditions in terms of thermal stability was performed by DSF. This high-throughput method had been shown to correlate very well with DSC data (differential scanning calorimetry) but has the advantage that several conditions can be analyzed simultaneously. In a first screen, all buffers were analyzed in presence and absence of 150 mM sodium chloride, and pH steps of at least 0.5 within the buffer capacity range of the corresponding buffers. In Table 3, below, all analyzed conditions are summarized. Additionally, the most promising buffer environments for Hpx (D, G and K) were further analyzed in regard of different buffer concentrations (15-300 mM) and the addition of different sodium chloride concentrations (50-600 mM) as shown in Table 3, below.

TABLE 3

Overview of buffers analyzed.

| No | Buffer | pH range | Ionic strength [mM] | NaCl [mM] |
|---|---|---|---|---|
| A | PBS* | 7.4 | 10 | 140 |
| B | Sodium acetate | 3.7-5.6 | 100 | 0; 150 |
| C | Citrate | 3.0-6.2 | 100 | 0; 150 |
| D | Citrate phosphate (a) | 2.6-7.6 | 15-200 | 0; 50-600 |
| E | Histidine | 5.5-7.4 | 100 | 0; 150 |
| F | Imidazole | 6.2-7.8 | 100 | 0; 150 |
| G | Sodium phosphate (b) | 5.7-8.0 | 25-300 | 0; 50-300 |
| H | Potassium phosphate | 5.8-8.0 | 100 | 0; 150 |
| I | Tris (Tris(hydroxymethyl) aminomethane) | 7.2-9.0 | 100 | 0; 50-250 |
| J | Arginine | 8.0-12.0 | 100 | 150 |
| K | Glycine (c) | 8.8-10.6 | 25-200 | 150 |
| L | Sodium carbonate | 9.2-10.8 | 100 | 0; 150 |

*Hpx formulated in PBS (10 mM sodium phosphate, 140 mM NaCl, pH 7.4) served as a reference.

Figure 25:
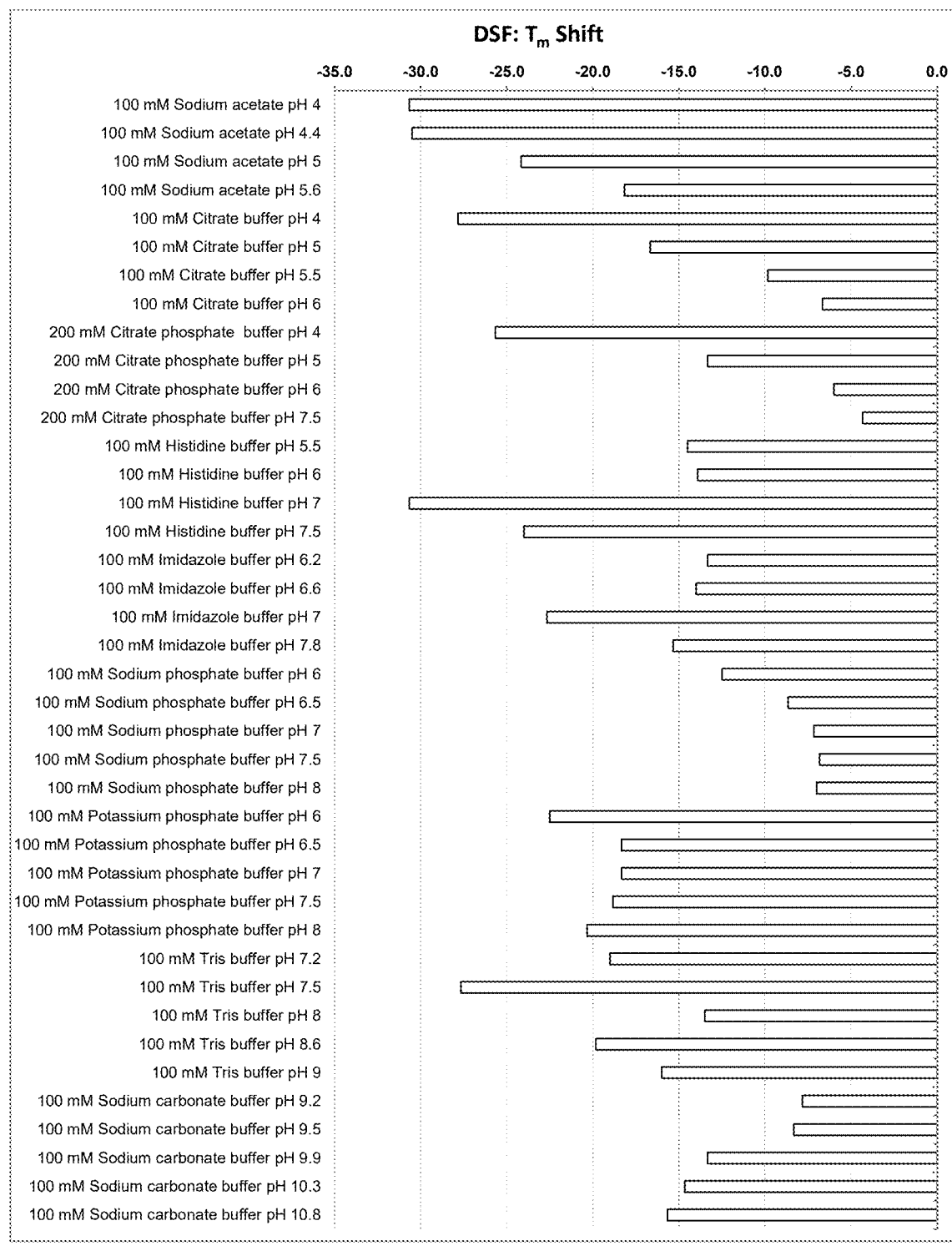
FIG. 25 shows a horizontal bar graph depicting shift in $T_m$ (as measured by DSF) in various buffers of varying pH (100 mM sodium acetate buffer, 100 mM citrate buffer, 200 mM citrate phosphate buffer, 100 mM histidine buffer, 100 mM imidazole buffer, 100 mM sodium phosphate buffer, 100 mM potassium phosphate buffer, 100 mM Tris buffer, and 100 mM sodium carbonate buffer), each of which do not comprise NaCl.
Figure 26:
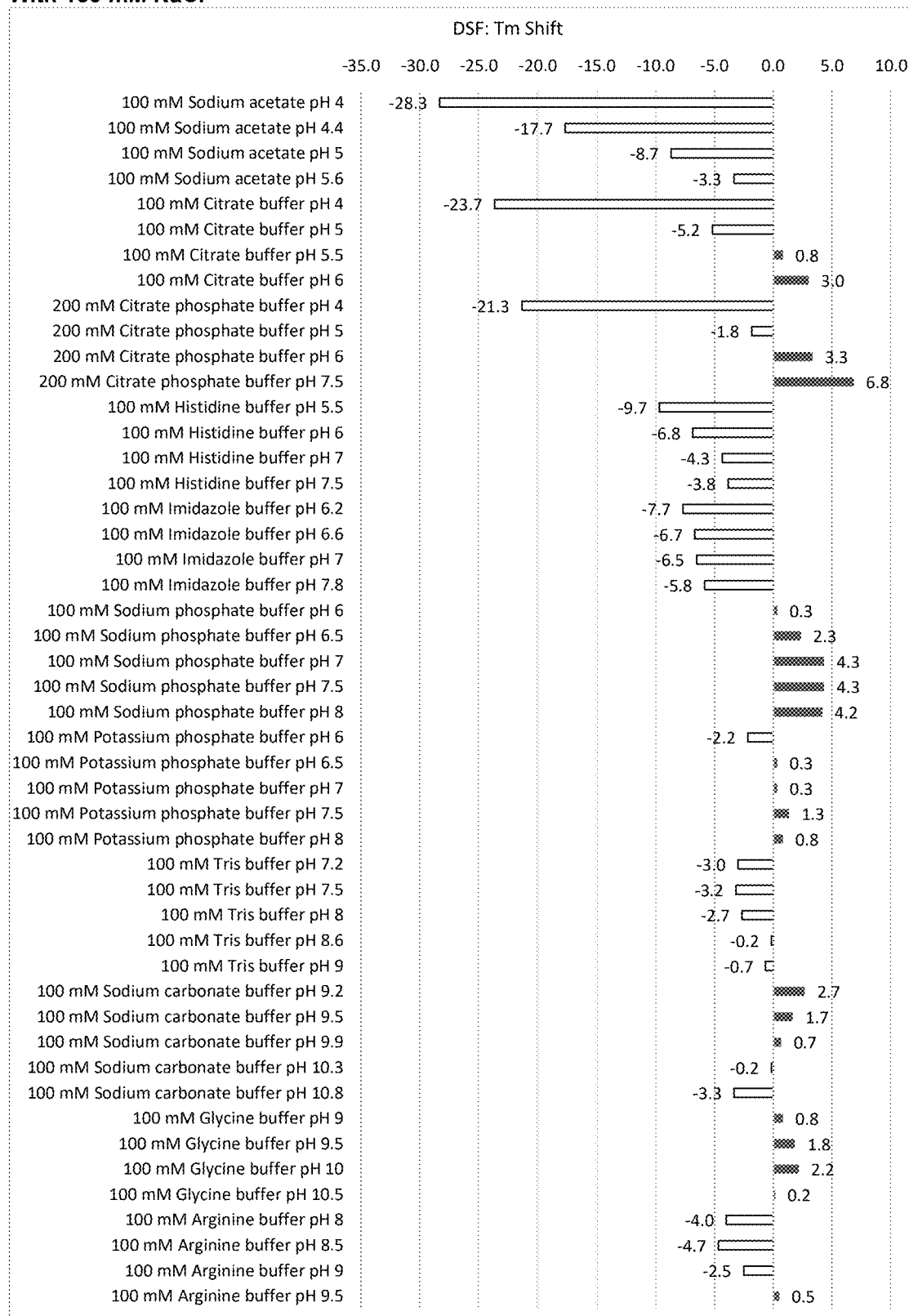
FIG. 26 shows a horizontal bar graph depicting shift in $T_m$ (as measured by DSF) in various buffers of varying pH (100 mM sodium acetate buffer, 100 mM citrate buffer, 200 mM citrate phosphate buffer, 100 mM histidine buffer, 100 mM imidazole buffer, 100 mM sodium phosphate buffer, 100 mM potassium phosphate buffer, 100 mM Tris buffer, 100 mM sodium carbonate buffer, 100 mM glycine buffer, and 100 mM arginine buffer), each of which comprises 150 mM NaCl.

For each condition, the corresponding $T_m$ value was determined and compared to Hpx in PBS, pH 7.4, which served as reference $T_m$. The results were either expressed as the absolute $T_m$ or as delta $T_m$ in relation to the reference ($T_m$ of Hpx diluted in PBS). As shown in FIG. 4A, three buffers (a, b and c; citrate phosphate, sodium phosphate and glycine) induced a thermal shift towards a clearly higher $T_m$ of Hpx, which implicated a stabilizing effect on the protein. Furthermore, in the absence of sodium chloride all three buffers showed an early onset of protein melting (data shown in FIG. 25; screening 1) demonstrating the necessity of sodium chloride as a stabilizer. This observation was further analyzed by supplementing the three stabilizing buffers with different concentrations of sodium chloride (50-250 mM). As shown in FIGS. 4A and B, with increasing concentrations of sodium chloride, an enhanced thermal stability could be achieved in a dose-dependent manner. A broad pH range could be covered with all the buffers tested, however, according to FIG. 4C a pH between 7.0 and 7.6 seemed to be the optimal condition.

Hpx formulated in citrate phosphate buffer (200 mM) and in presence of 150 mM NaCl at pH 7.2 resulted in fairly good thermal stability ($\Delta T_m$: 7° C.), but the resulting osmolarity was unfavorably high (approx. 880 mOsm/L). Therefore, several combinations of citrate phosphate concentrations and sodium chloride concentrations were analyzed as shown in FIG. 4D. To maintain a similar thermal stability at lower citrate phosphate concentrations, a higher sodium chloride concentration needs to be applied which has no or even increasing impact on the overall osmolarity of the solution. A lower osmolarity can only be achieved by lowering both, buffer and sodium chloride, but this also causes reduced thermal stability.

In summary, a buffer system comprising of either citrate or sodium phosphate at neutral pH and in combination with sodium chloride (>150 mM) might be an appropriate formulation for hemopexin derived from human plasma at least in terms of thermal stability. Hemopexin was subsequently diafiltrated into different buffer systems of the above mentioned salts and at different combination of concentrations, as described in the following sections.

The complete data sets of all combinations analyzed are summarized in FIGS. 25-32.

Example 3. Excipient Screenings 3.1. Sugars

The impact of sugars on thermal stability was explored. The previously defined buffers, which yielded enhanced thermal protein stability, were supplemented with different sugars at different concentrations. Briefly, sucrose, trehalose or mannitol at concentrations of 2.5%, 5%, 7.5% and 10% were added in presence of 150 mM NaCl into the corresponding buffers as shown in Table 4, below.

TABLE 4

Overview of sugars analyzed

| Buffer | pH | Sugar | Concentration [%] | Osmolarity [mOsm/L] |
|---|---|---|---|---|
| 200 mM Citrate phosphate | 7.2 | Sucrose | 2.5, 5, 7.5, 10 | 908-1127 |
| 200 mM Citrate phosphate | 7.2 | Trehalose | 2.5, 5, 7.5, 10 | 901-1099 |
| 200 mM Citrate phosphate | 7.2 | Mannitol | 2.5, 5, 7.5, 10 | 972-1384 |
| 100 mM Sodium phosphate | 7.8 | Sucrose | 2.5, 5, 7.5, 10 | 665-884 |
| 100 mM Sodium phosphate | 7.8 | Trehalose | 2.5, 5, 7.5, 10 | 658-856 |
| 100 mM Sodium phosphate | 7.8 | Mannitol | 2.5, 5, 7.5, 10 | 729-1141 |
| 100 mM Glycine buffer | 9.6 | Sucrose | 2.5, 5, 7.5, 10 | 473-692 |
| 100 mM Glycine buffer | 9.6 | Trehalose | 2.5, 5, 7.5, 10 | 466-664 |
| 100 mM Glycine buffer | 9.6 | Mannitol | 2.5, 5, 7.5, 10 | 537-949 |

Figure 5:
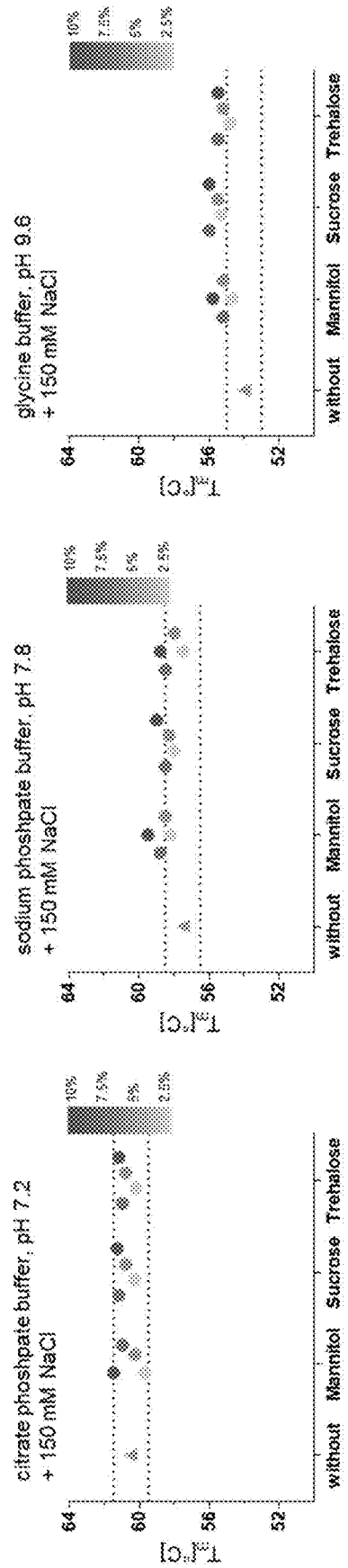
FIG. 5 shows thermal stability in the presence of different sugars by DSF. Visualization of $T_m$ and the corresponding buffer types in a scatter plot. The different sugar concentrations in the three different buffers analyzed are in different shades of grey.

Thermal stability was assessed with the same settings as described above and the results were either expressed as the absolute $T_m$ or as delta $T_m$ in relation to the $T_m$ of Hpx diluted in PBS. As shown in FIG. 5, there is none or only marginal increase of thermal stability, which is limited to the highest sugar concentrations. Per definition, a significant effect on thermal stability is needed to depict a change of at least one degree (marked in the figures as dashed lines); all changes below that are most probably within the measurement error.

For Hpx formulated with citrate phosphate, all sugars tested had no additive effect on thermal stability, since the $T_m$ was already elevated (approx. 60° C.) compared to the reference formulation (PBS; $T_m$: 53° C.). In case of sodium phosphate-formulated Hpx, there was a clear dose-dependent increase upon addition of the three sugars, but again a significant increase was only achieved with the highest concentrations. In glycine formulated-Hpx, there was also a sugar dose-dependent increase of $T_m$, but the achieved thermal stability was still much lower than with the citrate phosphate formulation.

3.2. Amino Acids

To complete the DSF screening, amino acids as excipients were analyzed for their capacity of stabilizing Hpx. Amino acids were selected according to their potential stabilizing effects based on reported publications. Each subtype, i.e. polar, charged and hydrophobic amino acid, was represented. A summary of all analyzed conditions is shown in Table 5, below.

TABLE 5

Overview of amino acids

| Buffer | pH | Amino Acid | Concentration [mM] | Osmolarity [mOsm/L] |
|---|---|---|---|---|
| 200 mM citrate phosphate | 7.2 | L-arginine | 50, 100 | 885-935 |
| 200 mM citrate phosphate | 7.2 | L-proline | 50, 100 | 885-935 |
| 200 mM citrate phosphate | 7.2 | L-glutamic acid | 50 | 885 |
| 200 mM citrate phosphate | 7.2 | L-serine | 50, 100 | 885-935 |
| 200 mM citrate phosphate | 7.2 | L-glycine | 50, 100 | 885-935 |
| 200 mM citrate phosphate | 7.2 | L-isoleucine | 50, 100 | 885-935 |
| 200 mM citrate phosphate | 7.2 | L-valine | 50, 100 | 885-935 |

Figure 6:
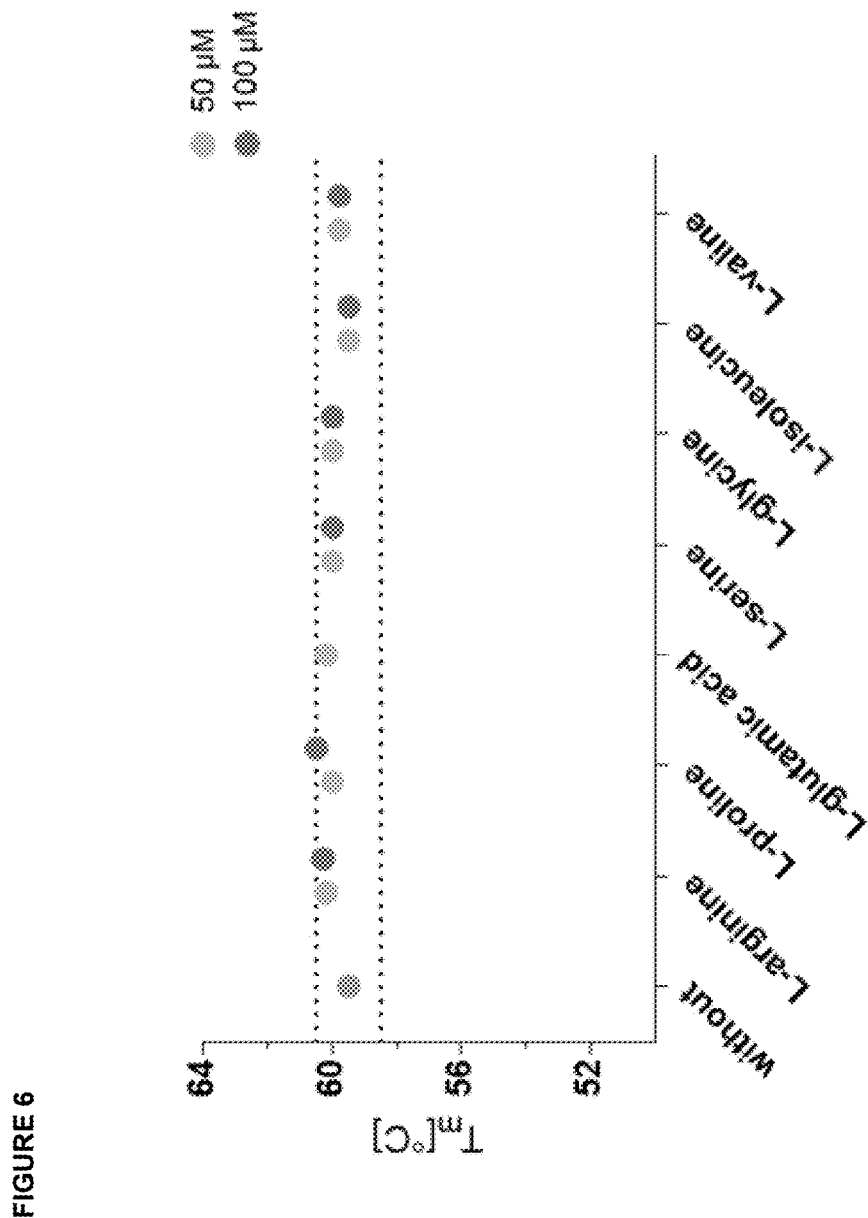
FIG. 6 shows thermal stability in the presence of different amino acids by DSF. Visualization of $T_m$ and the corresponding amino acids in citrate phosphate buffer in a scatter plot. Each amino acid was tested in two different concentrations (except for Glutamic acid, where only 50 µM was analyzed).

Each amino acid was analyzed in presence of 200 mM citrate phosphate buffer at pH 7.2 at two different concentrations (50 μM and 100 μM). Due to insolubility at 100 μM, glutamic acid was only analyzed at 50 μM. The data are presented in FIG. 6, and similar to the results achieved with sugars, only marginal increases in thermal stability were achieved by the addition of amino acid, the highest margin seen with arginine and proline. Based on these results, the contribution of amino acids to the stability of hemopexin in solution appears to be negligible.

3.3. Non-Ionic Detergents: Polysorbate 80 (P80)

Non-ionic surfactants can be used in protein formulations to inhibit protein aggregation due to agitation or shaking. The ability to stabilize proteins is attributed primarily to their ability to outcompete protein molecules for hydrophobic surfaces such as air-water interfaces, thereby preventing proteins from unfolding at these hydrophobic interfaces. In this study, the potential stabilizing effects of polysorbate 80 (P80) on hemopexin in solution was investigated. As the fluorescent dye used for DSF analyses binds to the hydrophobic tail of P80, alternative stability assays were used to assess the influence of P80 in Hpx formulations. Briefly, Hpx was concentrated to a final protein concentration of 10% (100 mg/mL) and diafiltrated either against (i) 200 mM citrate phosphate, 150 mM NaCl, pH 7.2 or (ii) PBS, pH 7.4 as shown in Table 6, below. Polysorbate 80 was spiked into the finally formulated Hpx solutions at concentrations starting from 0.001% to 0.1%. An unspiked sample served as control.

TABLE 6

Overview of polysorbate 80-containing formulations

| Buffer | pH | NaCl [mM] | concentrations [%] |
|---|---|---|---|
| 200 mM citrate phosphate | 7.2 | 150 | 0.1, (0.02,) 0.01, (0.002,) 0.001, w/o |
| PBS | 7.4 | 140 | 0.1, (0.02,) 0.01, (0.002,) 0.001, w/o |

The P80 spiked formulations were exposed to varying stress conditions, including agitation and freeze/thaw cycles, as shown in Table 7, below, to assess their relative stabilities over a storage period of three months at room temperature (RT) and at 37° C.

TABLE 7

Stress conditions and time points

| Stress | Conditions | Stability time point (months) |
|---|---|---|
| agitation | 1000 rpm at 25° C. for 4 h | 0 |
| freeze/thaw cycles | −70° C. to ambient temperature, 5 consecutive cycles | 0 |
| temperature | 25° C. and 37° C. | 0, 1, 2 and 3 |

Figure 7:
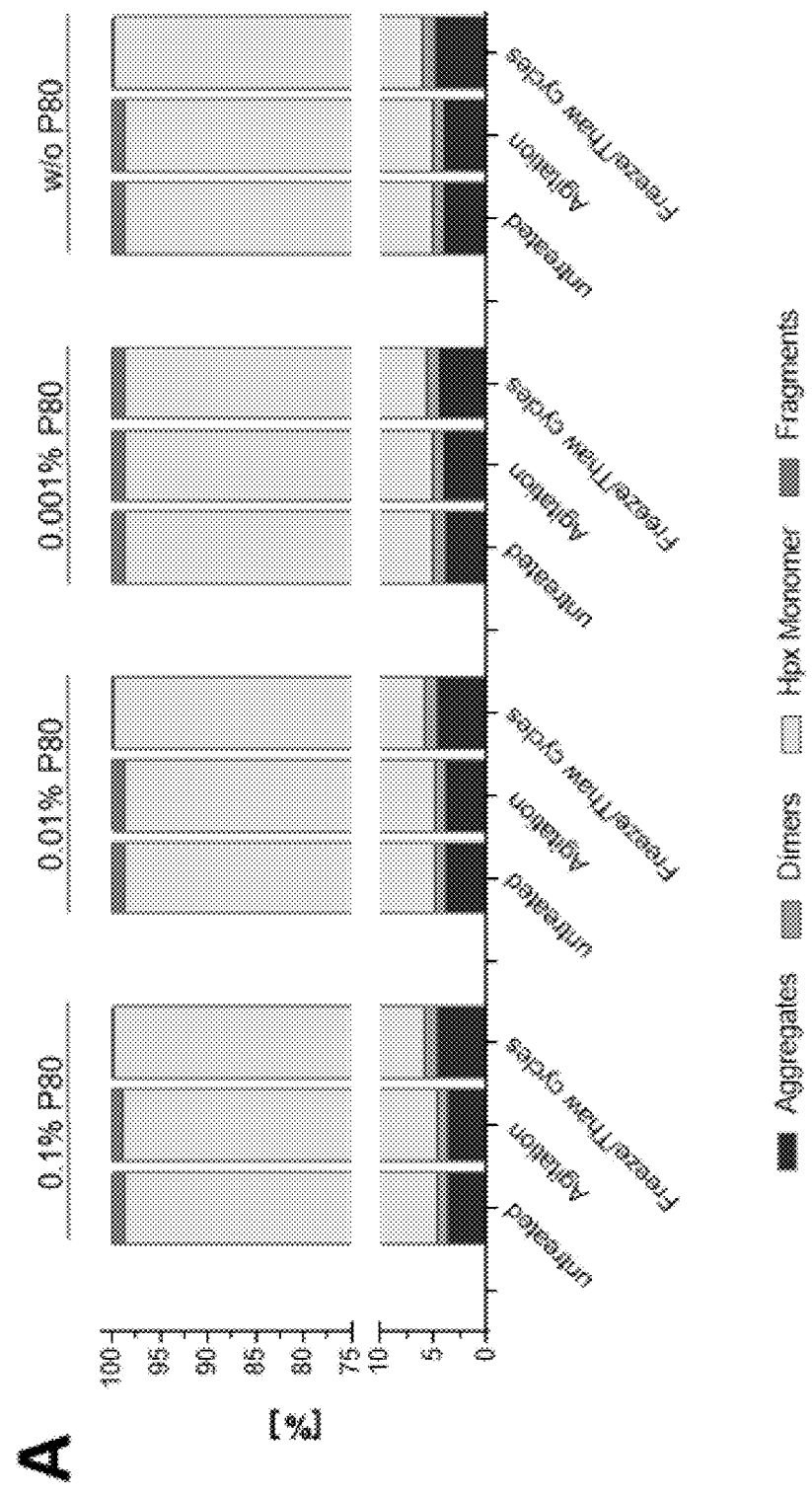
FIG. 7 shows data from the SEC-HPLC analysis upon physical stress-induced stability. A: Hpx formulated in PBS, pH 7.4, at different concentrations of P80; B: Hpx formulated in citrate phosphate, pH 7.4 at different concentrations of P80. Molecular size distribution is presented as a 100% stacked column chart and each molecular species is shown as the respective amount in percentage. Aggregates and dimers are highlighted at the bottom of each column (black and grey, respectively); fragments are shown at the top of each column (grey).
Figure 7:
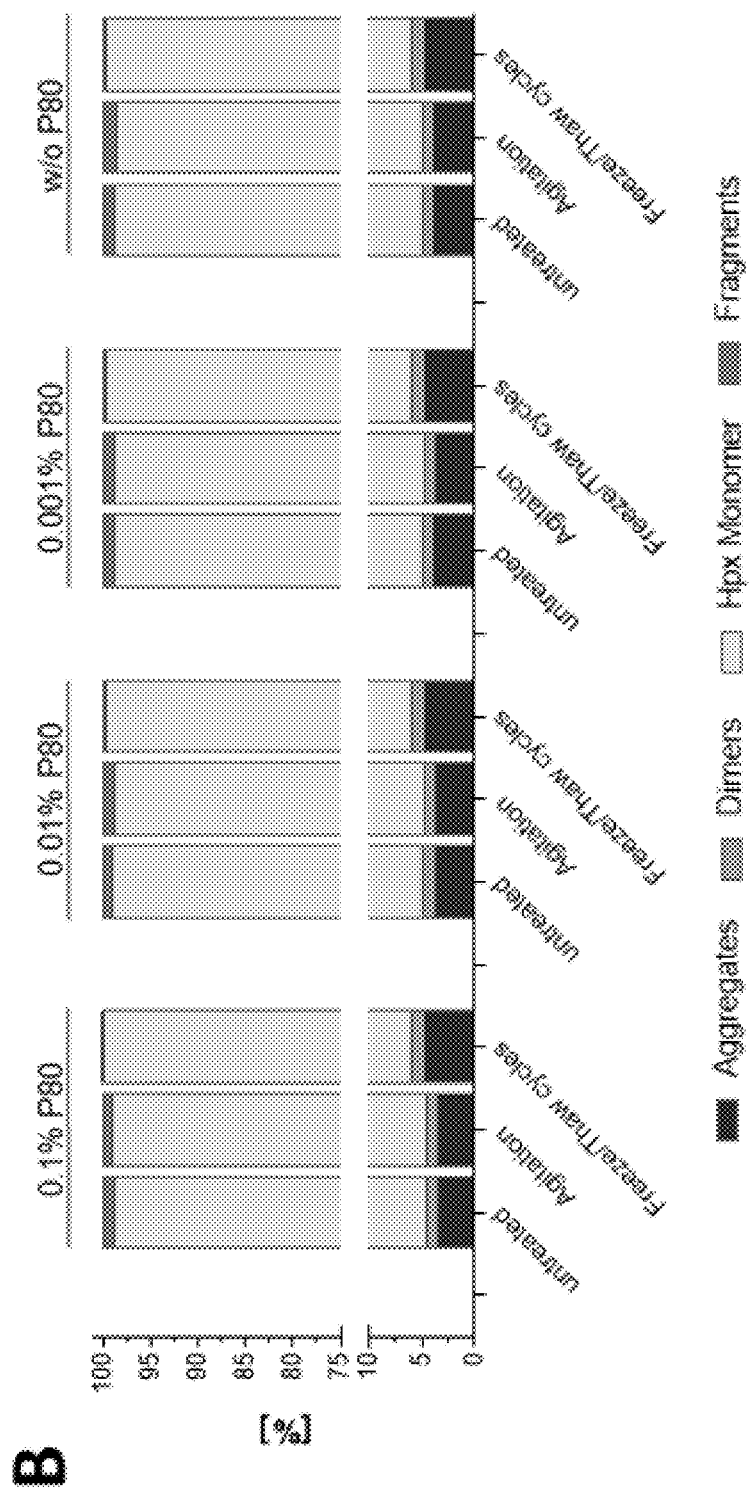
Figure 8:
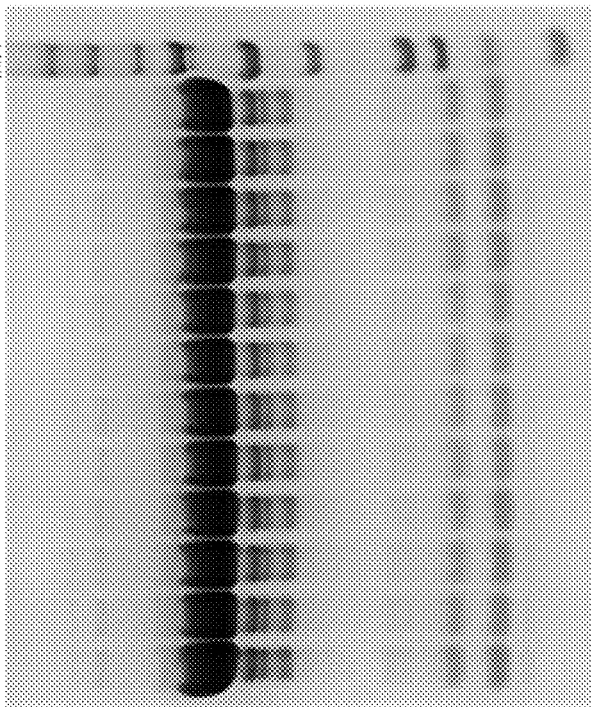
FIGS. 8A-D are photographs of SDS-PAGE gels for samples run after treatment with different physical induced stresses. Hpx samples formulated in PBS, pH 7.4 were analyzed under reducing (A 500 mM dithiothreitol, DTT) and non-reducing (C) conditions. Hpx samples formulated in citrate phosphate, pH 7.4 were analyzed under reducing (B 500 mM dithiothreitol, DTT) and non-reducing (D) conditions. U: untreated; A: agitated; F/T: Freeze/Thaw cycles.
Figure 8:
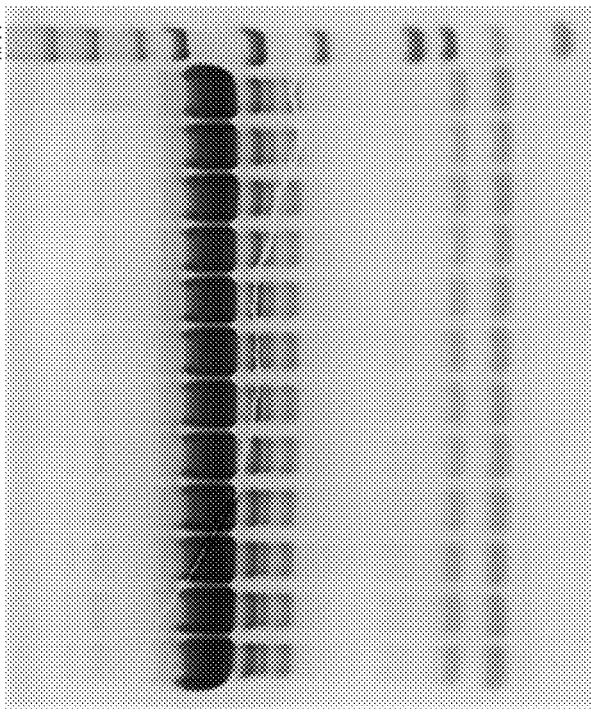
Figure 8:
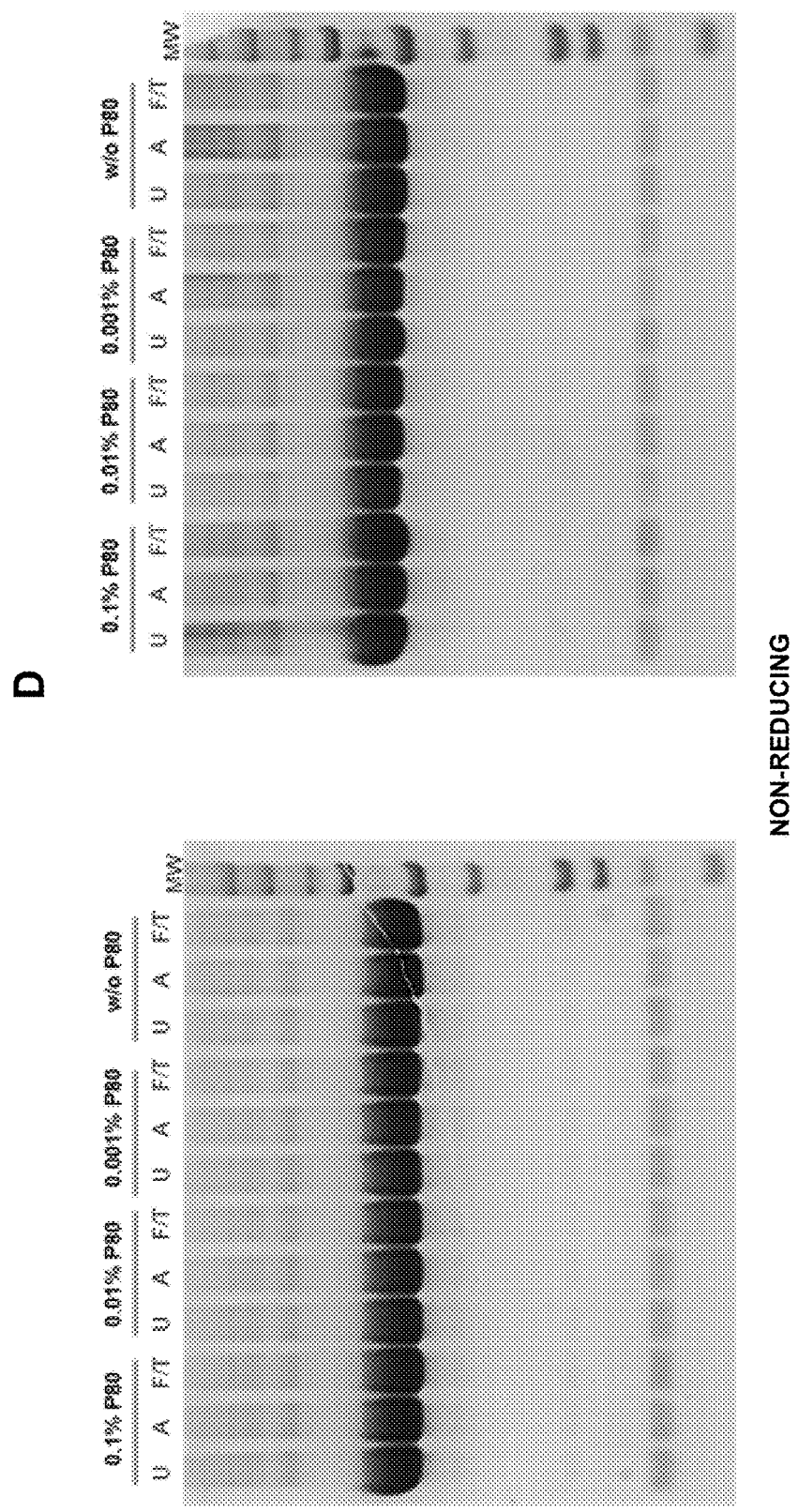

In a first series of experiments, each Hpx formulation was subjected to constant agitation to understand the stability of the product under shear stress to determine if the non-ionic surfactant would be beneficial or not, regarding protein stability. The samples were agitated on a bench-top thermocycler at 1000 rpm for 4 hours at 25° C. An identical set of samples without agitation served as control. After the agitation period, samples were analyzed by SEC-HPLC as shown in FIG. 7. The agitated formulations demonstrated no major aggregation upon stress as well as no change in dimer or fragment formation. Further, all 8 formulations were subjected to 5 consecutive freeze/thaw cycles, from −70° C. to ambient temperature, to assess for physical stability; again a set of identical formulations without undergoing freeze/thaw cycles was used as control. SEC-HPLC, as shown in FIG. 7, revealed that after 5 consecutive freeze/thaw cycles the amount of aggregates was slightly increased compared to the untreated control group. This observation was made in all 8 formulations, independent of a specific P80 concentration. Interestingly, the formulations undergoing freeze/thaw cycles did not depict any fragments.

Figure 9:
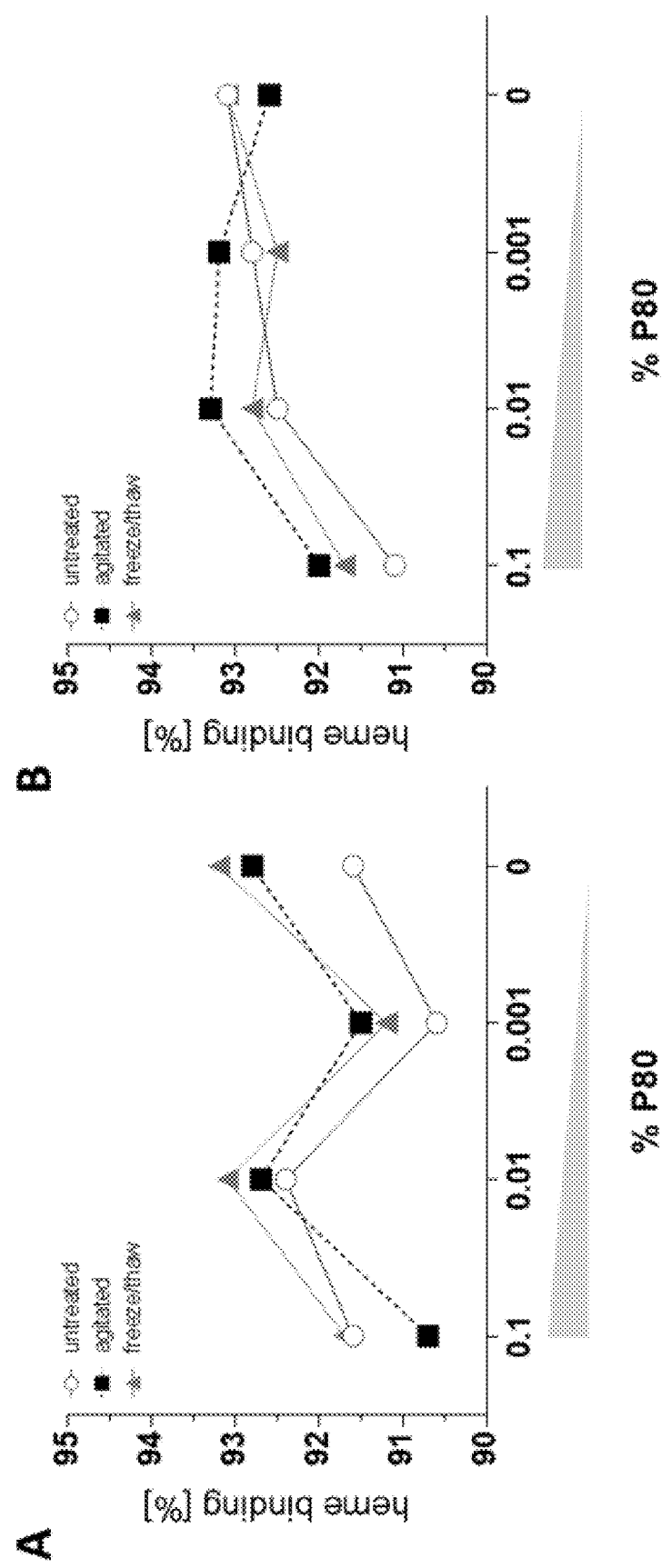
FIG. 9 shows Heme binding to hemopexin upon physical-induced stress. A: PBS, 140 mM NaCl, pH 7.4; and B: Hpx formulated in citrate phosphate, pH 7.4 at different concentration of P80. Heme binding is shown in percentage after treatments as indicated; Untreated—open circles; Agitated—black squares; freeze/thaw—grey triangles.

Whereas SEC-HPLC revealed a slight increase in aggregates after consecutive freeze/thaw cycles, although independent of a specific P80 concentration, no differences were observed after all samples were analyzed by SDS-PAGE (reduced and non-reduced) as shown in FIGS. 8A-D. Moreover, the capability of Hpx to bind heme, which was demonstrated by the heme binding assay (FIG. 9), was not affected by the presence of different P80 concentrations. Differences in heme binding capacity between the various P80 concentrations are within the assay variability (<5%). Hence, P80 does not impair heme binding at any concentration and treatment tested.

As described above, all formulations were stored under accelerated conditions (37° C.) and at RT for at least 3 months and samples were analyzed after each month of storage (see Example 4, below).

Example 4. Stability Studies Under Various Conditions 4.1. Formulation Preparation The previously preferred conditions, based on DSF as described above, were further investigated by performing stability studies under different storage conditions (short and long term). Briefly, Hpx formulated in PBS was concentrated to 10% Hpx and diafiltrated into the desired buffer and excipient compositions as shown in Table 8, below. pH adjustments were performed by carefully titrating 0.2 M HCl or 0.2 M NaOH if necessary. Afterwards, each formulation was sterile filtered, filled into sterile glass vials and stored at different temperatures for subsequent analysis at time points 0, 1, 2, and 3 months or as otherwise indicated.

TABLE 8

| No | Buffer | NaCl [mM] | pH | P80 [%] | osmolarity [mOsm/L] | $T_m$ [° C.] | viscosity [mPa*s] |
|---|---|---|---|---|---|---|---|
| Short term stability study with P80 (Hpx stability study 2 & 4) | | | | | | | |
| I | PBS | 140 | 7.4 | 0.1 | 307 | n/a | 2.9 |
| II | PBS | 140 | 7.4 | 0.02 | 307 | n/a | 2.8 |
| III | PBS | 140 | 7.4 | 0.01 | 307 | n/a | 3.0 |
| IV | PBS | 140 | 7.4 | 0.002 | 307 | n/a | 2.7 |
| V | PBS | 140 | 7.4 | 0.001 | 307 | n/a | 3.3 |
| VI | PBS | 140 | 7.4 | — | 307 | n/a | 3.2 |
| Stability study: lead formulations | | | | | | | |
| a | 200 mM citrate phosphate | 150 | 7.2 | 0.002 | 876 | 60.3 ± 0.5 | 2.2 |
| b | 200 mM citrate phosphate | 300 | 7.2 | 0.002 | 1176 | 63.4 ± 0.2 | 3.4 |
| c | 100 mM sodium phosphate | 150 | 7.6 | 0.002 | 587 | 57.2 ± 0.2 | 2.5 |
| d | 100 mM sodium phosphate | 300 | 7.6 | 0.002 | 887 | 59.7 ± 0.5 | 3.0 |
| e | 300 mM sodium phosphate | 150 | 7.6 | 0.002 | 1161 | 64.3 ± 0.5 | 3.1 |
| f | PBS | 140 | 7.4 | — | 307 | 53.1 ± 0.5 | 3.2 |
| Stability study: lead formulation with reduced phosphate and reduced osmolarity | | | | | | | |
| (1) | 15 mM citrate phosphate | 150 | 7.2 | 0.01 | 343 | 53.7 ± 0.1 | 2.8 |
| (2) | 15 mM citrate phosphate | 300 | 7.2 | 0.01 | 643 | 56.1 ± 0.4 | 2.7 |
| (3) | 50 mM citrate phosphate | 200 | 7.2 | 0.01 | 544 | 57.3 ± 0.2 | 2.8 |
| (4) | 50 mM citrate phophate | 400 | 7.2 | 0.01 | 944 | 59.8 ± 0.2 | 2.6 |
| (5) | 200 mM citrate phosphate | 150 | 7.2 | 0.01 | 876 | 60.3 ± 0.5 | 3.2 |

4.2. Short Term Stability Study with Different Concentrations of Polysorbate 80 in PBS Hpx formulated in PBS was concentrated to 10% and subsequently spiked with different concentrations of P80 as shown in Table 8 (1-VI).

Figure 10:
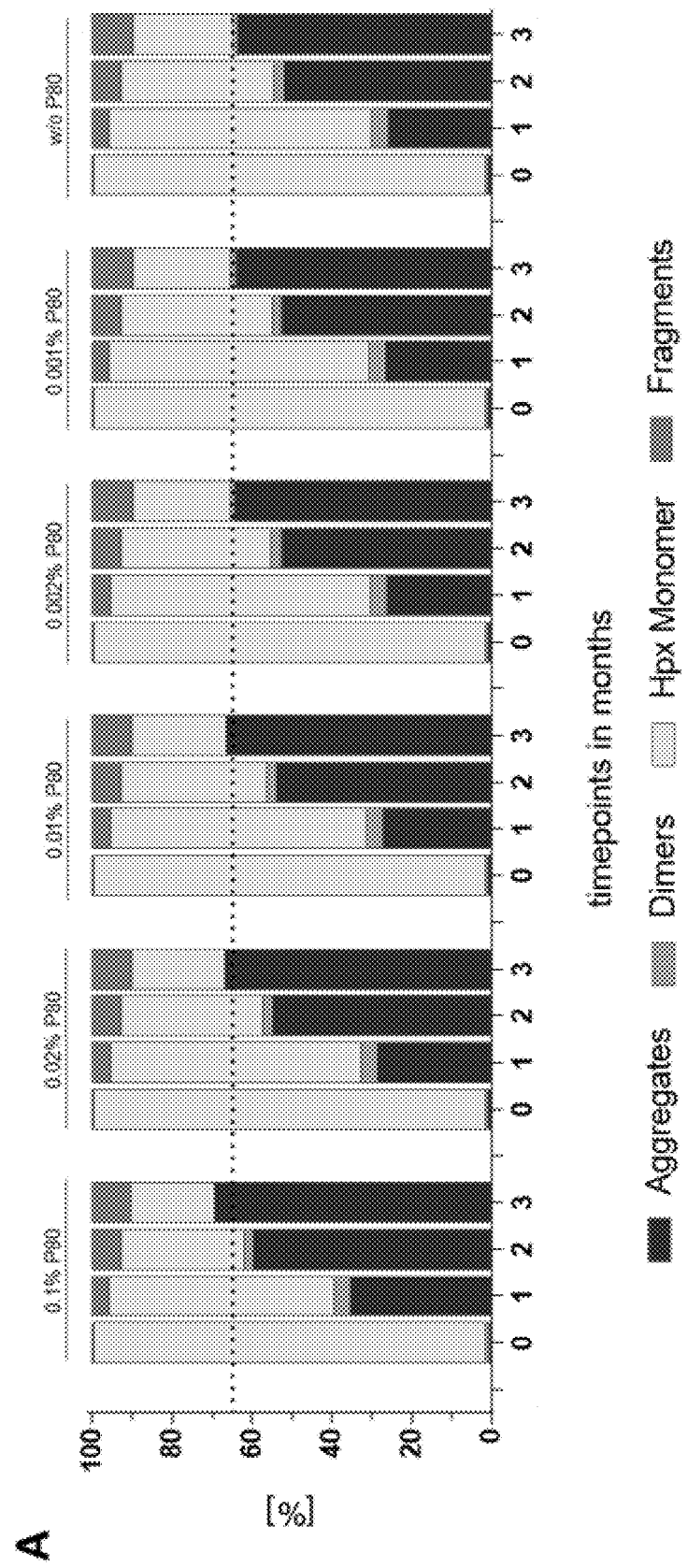
FIG. 10 shows the SEC-HPLC data of a 10% Hpx solution formulated in the absence of P80 (w/o P80) and with different concentrations of P80 (0.1-0.001% v/v) in PBS and analyzed over 3 months. Stored at A: 37° C. and B: 25° C. (RT). Molecular size distribution is presented as a 100% stacked column chart and each molecular species is shown as the respective amount in percentage. Aggregates and dimers are highlighted at the bottom of each column (black and grey, respectively); fragments are shown at the top of each column (grey).
Figure 10:
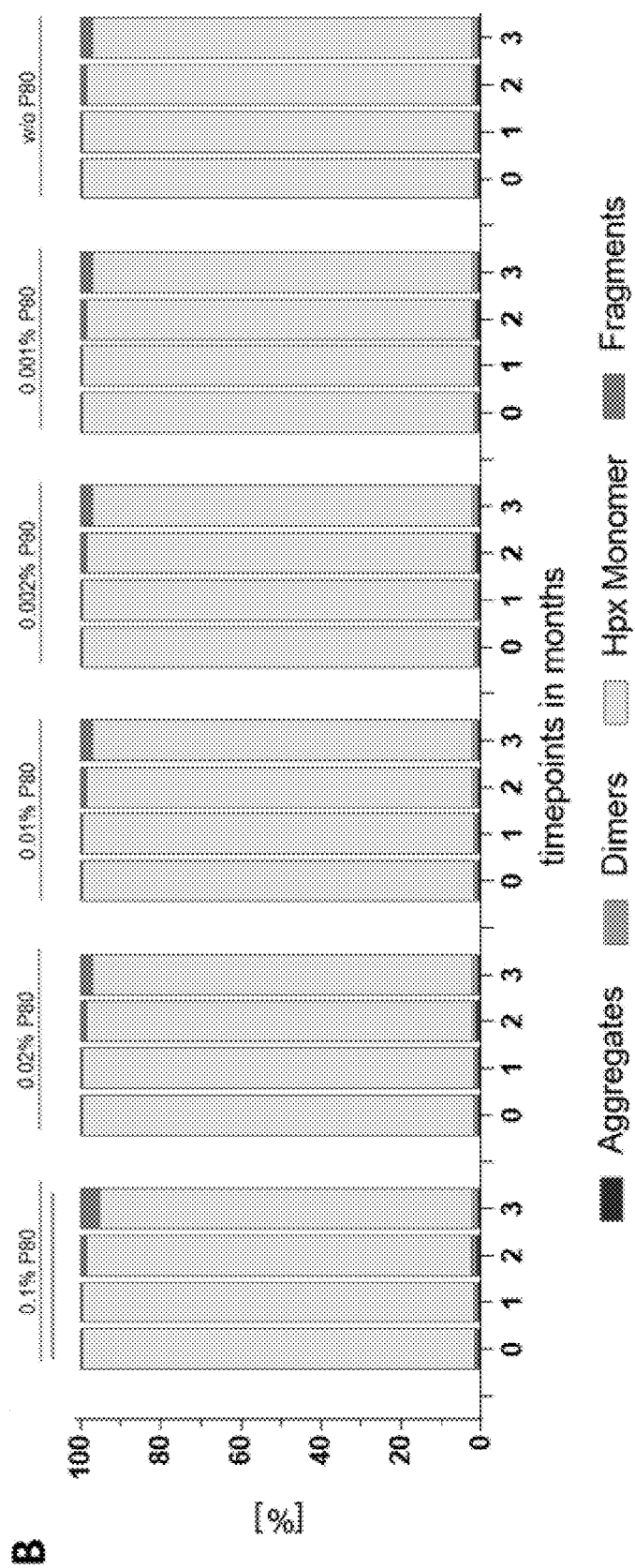

All formulations were stored for 3 months protected from light at room temperature and 37° C. At each time point, samples were analyzed by SEC-HPLC to monitor potential generation of oligomers and fragments. The molecular size distribution results for each P80 concentration after 3 months are shown in FIG. 10.

Following 37° C. storage, each of the Hpx formulations showed a significant increase in aggregates (after 3 months 63-70%), compared to the formulations stored for 3 months at RT (<1% increase in aggregates). The percent peak area results from the SEC-HPLC analysis of the control and P80 containing samples after storage at 37° C. for 3 months are displayed in Table 9, below. The complete SEC-HPLC results from zero, one, two and three-month time points for both storage conditions are shown in FIGS. 25-32.

TABLE 9

SEC-HPLC data after storage at 37° C. for 3 months.

| No | Formulation | Aggregates [%] | Dimers [%] | Monomers [%] | Fragments [%] |
|---|---|---|---|---|---|
| I | PBS, 0.1% P80, pH 7.2 | 69.6 | 0.0 | 20.7 | 9.7 |
| II | PBS, 0.02% P80, pH 7.2 | 66.8 | 0.0 | 23.3 | 10.0 |
| III | PBS, 0.01% P80, pH 7.2 | 66.4 | 0.0 | 23.5 | 10.1 |
| IV | PBS, 0.002% P80, pH 7.2 | 64.5 | 1.0 | 24.3 | 10.2 |
| V | PBS, 0.001% P80, pH 7.2 | 64.3 | 1.1 | 24.5 | 10.1 |
| VI | PBS, pH 7.4 | 63.8 | 1.2 | 24.9 | 10.2 |

Figure 11:
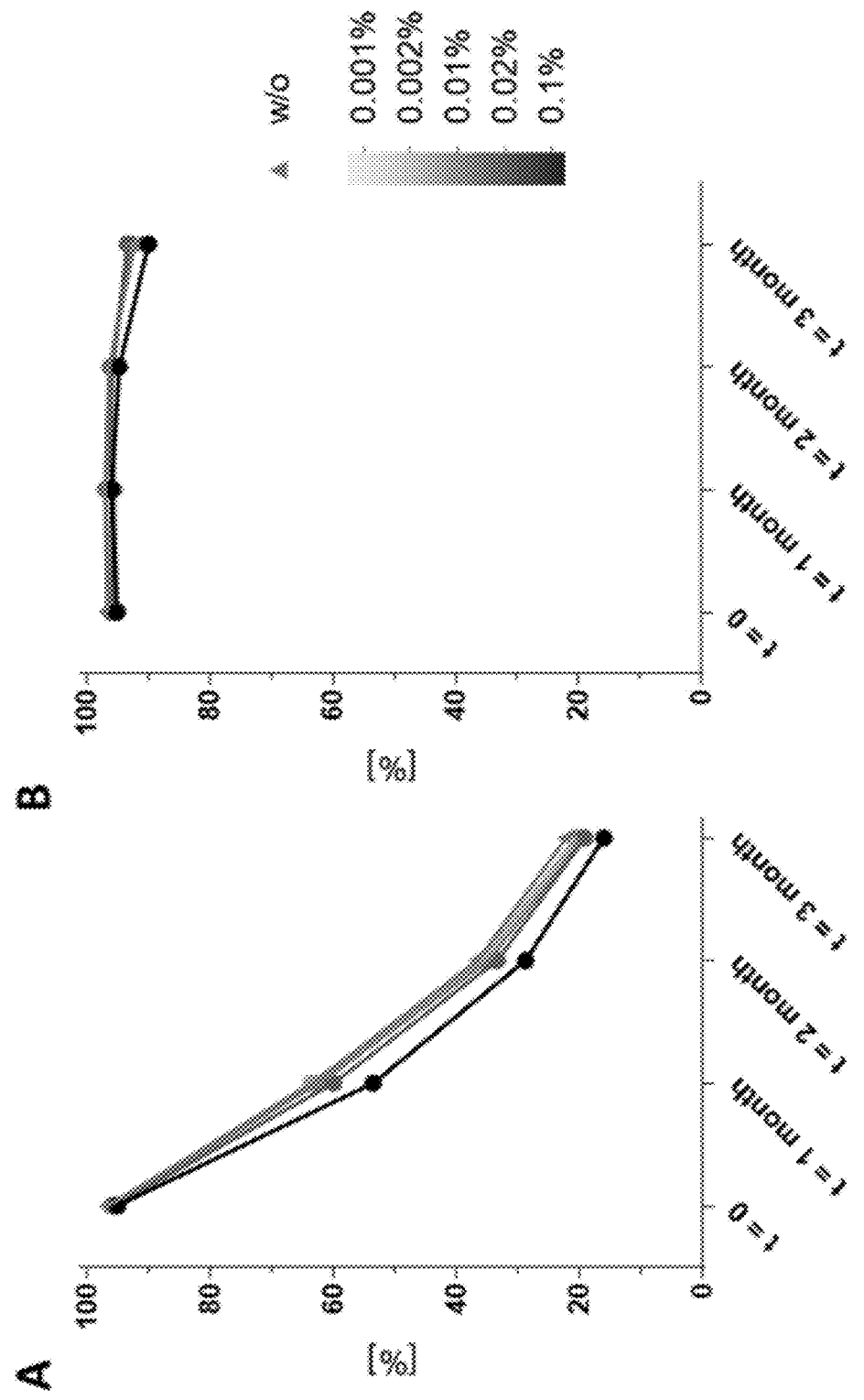
FIG. 11 shows the heme binding capability of a 10% Hpx solution formulated in the absence of P80 (w/o, triangles) and with different concentrations of P80 (0.1-0.001% v/v) in PBS and analyzed over 3 months. Stored at A: 37° C. and B: 25° C. (RT).

Further, the heme binding capability of hemopexin was assessed at each time point over a three-month period and the data (FIG. 11) revealed a similar picture as observed after SEC-HPLC data analysis. Heme binding was highly reduced from 95% to approx. 20-25% after storage at 37° C. for 3 months, which correlates very well with the amount of Hpx monomers at that time point (Table 9). Again, no differences between the P80 concentrations were observed, apart from the highest P80 concentration (0.1%, black curve), which showed lower heme binding activity compared to the other concentrations.

Samples stored at RT for three months showed a similar correlation between activity and Hpx monomer content. However, the difference between the sample containing 0.1% P80 and all other samples was less pronounced at RT than at 37° C. (FIG. 11B).

In summary, P80 concentrations of 0.02% and below did not impair stability with regard to molecular size distribution and heme binding activity. It was also found that Hpx formulated in PBS, irrespective of P80 concentration, exhibited a strong reduction of protein monomer content and heme binding activity over 3 months at 37° C. Hence, the PBS formulation is not providing the required Hpx stability at accelerating temperatures.

4.3. Stability Study: Lead Formulations

Figure 12:
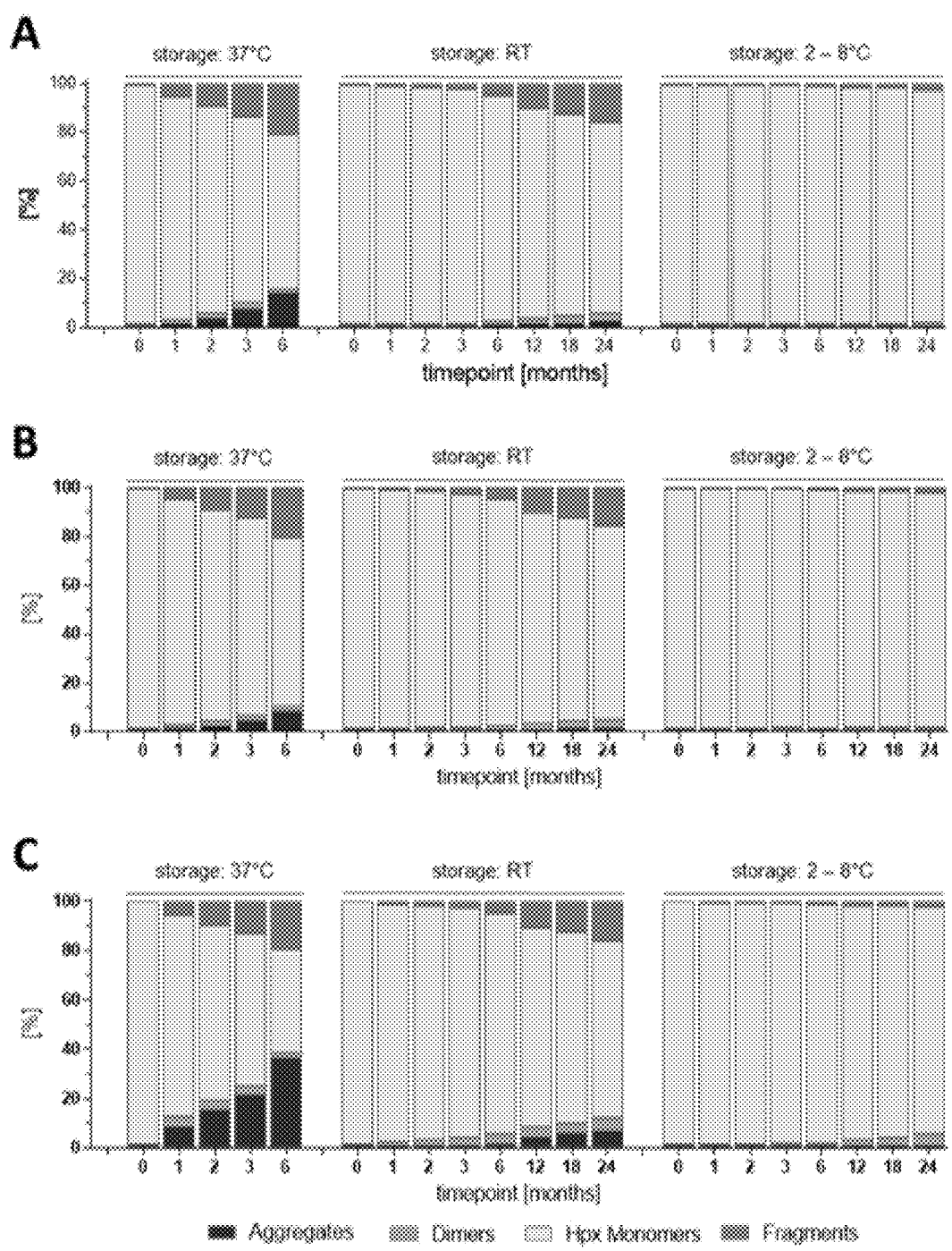
FIG. 12 shows the SEC-HPLC data of a 10% Hpx solution formulated with different buffers and analyzed over 6 months upon accelerated conditions (37° C.) storage and up to 24 months upon storage at room temperature (RT) and at 2-8° C. A: 200 mM citrate phosphate, 150 mM NaCl, pH 7.2; B: 200 mM citrate phosphate, 300 mM NaCl, pH 7.2; C: 100 mM sodium phosphate, 150 mM NaCl, pH 7.6; D: 100 mM sodium phosphate, 300 mM NaCl, pH 7.6; E: 300 mM sodium phosphate, 150 mM NaCl, pH 7.6; F: PBS, 140 mM NaCl, pH 7.4. All formulations (except PBS) contain 0.002% v/v P80. Molecular size distribution is presented as a 100% stacked column chart and each molecular species is shown as the respective amount in percentage. Aggregates and dimers are highlighted at the bottom of each column (black and grey, respectively); fragments are shown at the top of each column (grey).
Figure 12:
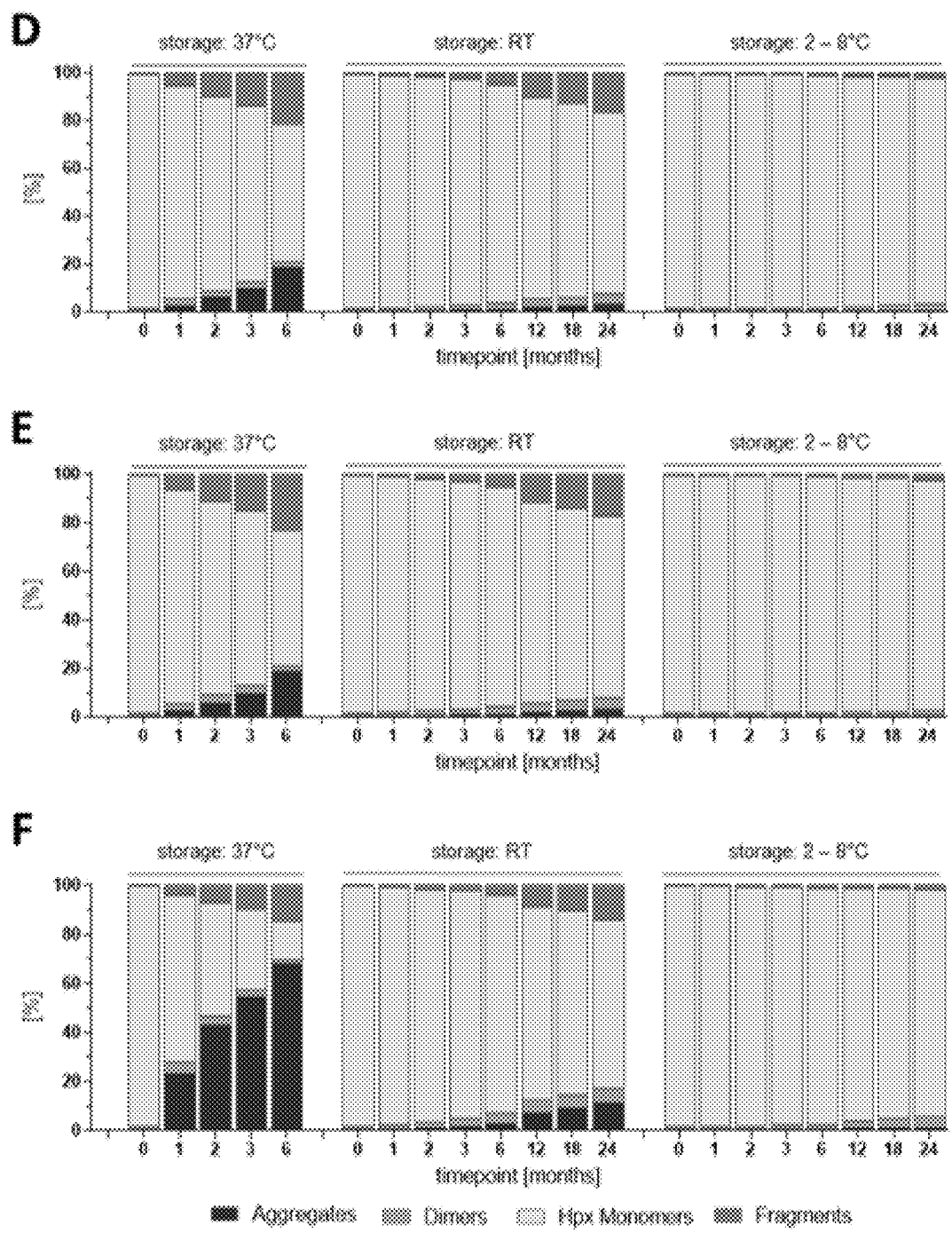

Hpx formulated in different buffers and salt concentrations were produced, as outlined in Table 8 (a-f). All formulations were spiked with P80 to achieve a final P80 concentration of 0.002% (except in PBS) and were stored for a least 6 months protected from light at 2-8° C., RT (25° C.) or 37° C. At each time point, samples were taken and subjected to SEC-HPLC analysis to measure the amount of monomers, oligomers and fragments of Hpx (Table 10). Molecular size distribution results are shown in FIG. 12. No significant changes in aggregates and fragments were observed between the different formulations and monomeric Hpx (>94%) remained stable throughout the whole study period (24 months) if stored at 2-8° C. Similarly, formulations stored at RT (24 months) remained nearly unchanged, except for a slight increase in fragments over time, which was observed independently of the formulation. Following 37° C. storage, each of the Hpx formulations showed an increase in aggregates and fragments, whereas Hpx formulated with citrate phosphate appeared to be the most stable formulation. Stability in the citrate phosphate formulation was further improved by an increased sodium chloride concentration (formulations A and B), as shown by 63.3% (150 mM NaCl) and 68.9% (300 mM NaCl) Hpx monomer content after 6 months under accelerated conditions (37° C.).

Formulations comprising sodium phosphate buffer were less stable and exhibited an increase of aggregates of up to 36% after 6 months (with better outcome in the presence of higher salt concentrations or increased buffer concentrations). The fragment content remained very low at RT and at 2-8° C., whereas around 20% fragments were generated over time at 37° C.

These data correlate very well with the thermal stability data derived by DSF. Hence, the $T_m$ of Hpx in a specific formulation can be used as an indicator for the outcome of a short term stability study at higher protein concentrations.

TABLE 10

| No | Formulation | Aggregates [%] | Dimers [%] | Monomers [%] | Fragments [%] |
|---|---|---|---|---|---|
| | SEC-HPLC data after storage at 37° C. for 6 months | | | | |
| a | 200 mM citrate phosphate, 150 mM NaCl, 0.002% P80, pH 7.2 | 14.2 | 1.8 | 63.3 | 20.8 |
| b | 200 mM citrate phosphate, 300 mM NaCl, 0.002% P80, pH 7.2 | 8.5 | 2.0 | 69.0 | 20.6 |
| c | 100 mM sodium phosphate, 150 mM NaCl, 0.002% P80, pH 7.6 | 36.7 | 1.9 | 41.6 | 19.7 |
| d | 100 mM sodium phosphate, 300 mM NaCl, 0.002% P80, pH 7.6 | 18.6 | 2.3 | 57.5 | 21.6 |
| e | 300 mM sodium phosphate, 150 mM NaCl, 0.002% P80, pH 7.6 | 19.1 | 1.9 | 55.6 | 23.4 |
| f | PBS, pH 7.4 | 68.3 | 1.5 | 15.3 | 14.8 |
| | SEC-HPLC data after storage at RT for 12 months | | | | |
| a | 200 mM citrate phosphate, 150 mM NaCl, 0.002% P80, pH 7.2 | 1.4 | 2.6 | 85.3 | 10.6 |
| b | 200 mM citrate phosphate, 300 mM NaCl, 0.002% P80, pH 7.2 | 1.1 | 2.7 | 85.9 | 10.3 |
| c | 100 mM sodium phosphate, 150 mM NaCl, 0.002% P80, pH 7.6 | 4.5 | 4.4 | 80.3 | 10.9 |
| d | 100 mM sodium phosphate, 300 mM NaCl, 0.002% P80, pH 7.6 | 2.2 | 3.3 | 83.8 | 10.7 |
| e | 300 mM sodium phosphate, 150 mM NaCl, 0.002% P80, pH 7.6 | 2.2 | 3.8 | 82.1 | 11.85 |
| f | PBS, pH 7.4 | 7.5 | 5.0 | 78.5 | 9.0 |
| | SEC-HPLC data after storage at 2-8° C. for 12 months | | | | |
| a | 200 mM citrate phosphate, 150 mM NaCl, 0.002% P80, pH 7.2 | 0.8 | 0.9 | 96.7 | 1.6 |
| b | 200 mM citrate phosphate, 300 mM NaCl, 0.002% P80, pH 7.2 | 0.8 | 1.0 | 96.6 | 1.6 |
| c | 100 mM sodium phosphate, 150 mM NaCl, 0.002% P80, pH 7.6 | 1.0 | 2.6 | 94.7 | 1.8 |
| d | 100 mM sodium phosphate, 300 mM NaCl, 0.002% P80, pH 7.6 | 0.9 | 1.4 | 96.1 | 1.7 |
| e | 300 mM sodium phosphate, 150 mM NaCl, 0.002% P80, pH 7.6 | 0.9 | 1.4 | 96.0 | 1.8 |
| f | PBS, pH 7.4 | 1.2 | 2.7 | 94.5 | 1.6 |

TABLE 10-continued

SEC-HPLC data after storage as indicated.

| No | Formulation | Aggregates [%] | Dimers [%] | Monomers [%] | Fragments [%] |
|---|---|---|---|---|---|
| | SEC-HPLC data after storage at 2-8° C. for 24 months | | | | |
| a | 200 mM citrate phosphate, 150 mM NaCl, 0.002% P80, pH 7.2 | 0.8 | 1.5 | 95.2 | 2.6 |
| b | 200 mM citrate phosphate, 300 mM NaCl, 0.002% P80, pH 7.2 | 0.8 | 1.4 | 95.4 | 2.4 |
| c | 100 mM sodium phosphate, 150 mM NaCl, 0.002% P80, pH 7.6 | 1.1 | 4.7 | 91.7 | 2.4 |
| d | 100 mM sodium phosphate, 300 mM NaCl, 0.002% P80, pH 7.6 | 0.9 | 2.6 | 94.2 | 2.3 |
| e | 300 mM sodium phosphate, 150 mM NaCl, 0.002% P80, pH 7.6 | 0.9 | 2.2 | 94.4 | 2.6 |
| f | PBS, pH 7.4 | 1.5 | 4.4 | 92.2 | 2.0 |

Figure 13:
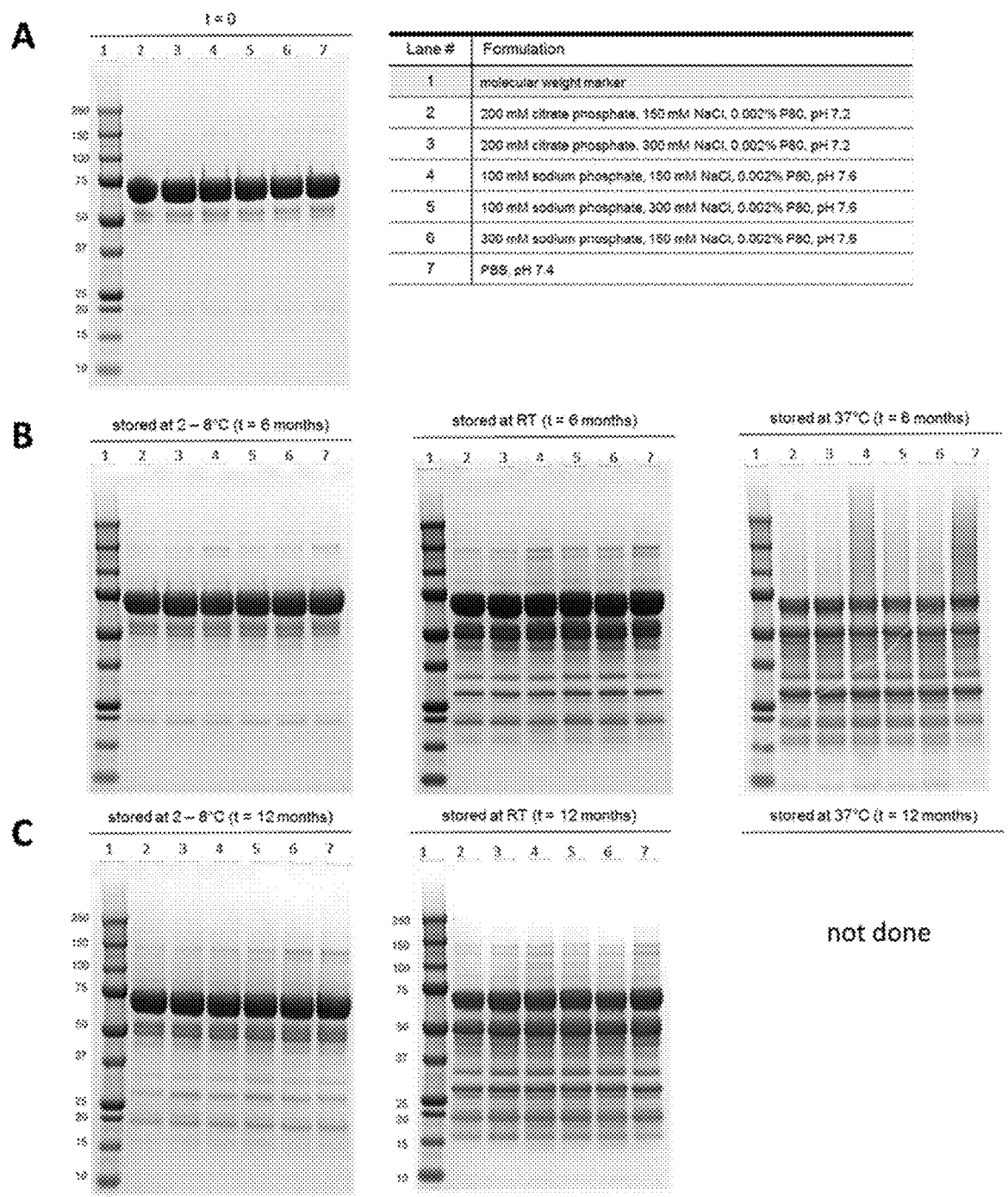
FIG. 13 shows photographs of SDS-PAGE gels with samples from time zero, 6 and 12 months. A-C: Samples were analyzed under reducing conditions (500 mM dithiothreitol, DTT). D-F: Samples were analyzed under non-reducing conditions. 15 µg protein was loaded into each lane. Each formulation was analyzed at time zero, 6- and 12-months storage as indicated. Molecular weight marker is shown in left lane, kDa values as indicated in the figure. Lane 1—molecular weight marker, Lane 2—200 mM citrate phosphate, 150 mM NaCl, 0.002% P80, pH 7.2; Lane 3—200 mM citrate phosphate, 300 mM NaCl, 0.002% P80, pH 7.2; Lane 4—100 mM sodium phosphate, 150 mM NaCl, 0.002% P80, pH 7.6; Lane 5—100 mM sodium phosphate, 300 mM NaCl, 0.002% P80, pH 7.6; Lane 6—300 mM sodium phosphate, 150 mM NaCl, 0.002% P80, pH 7.6; Lane 7—PBS, pH 7.4.
Figure 13:
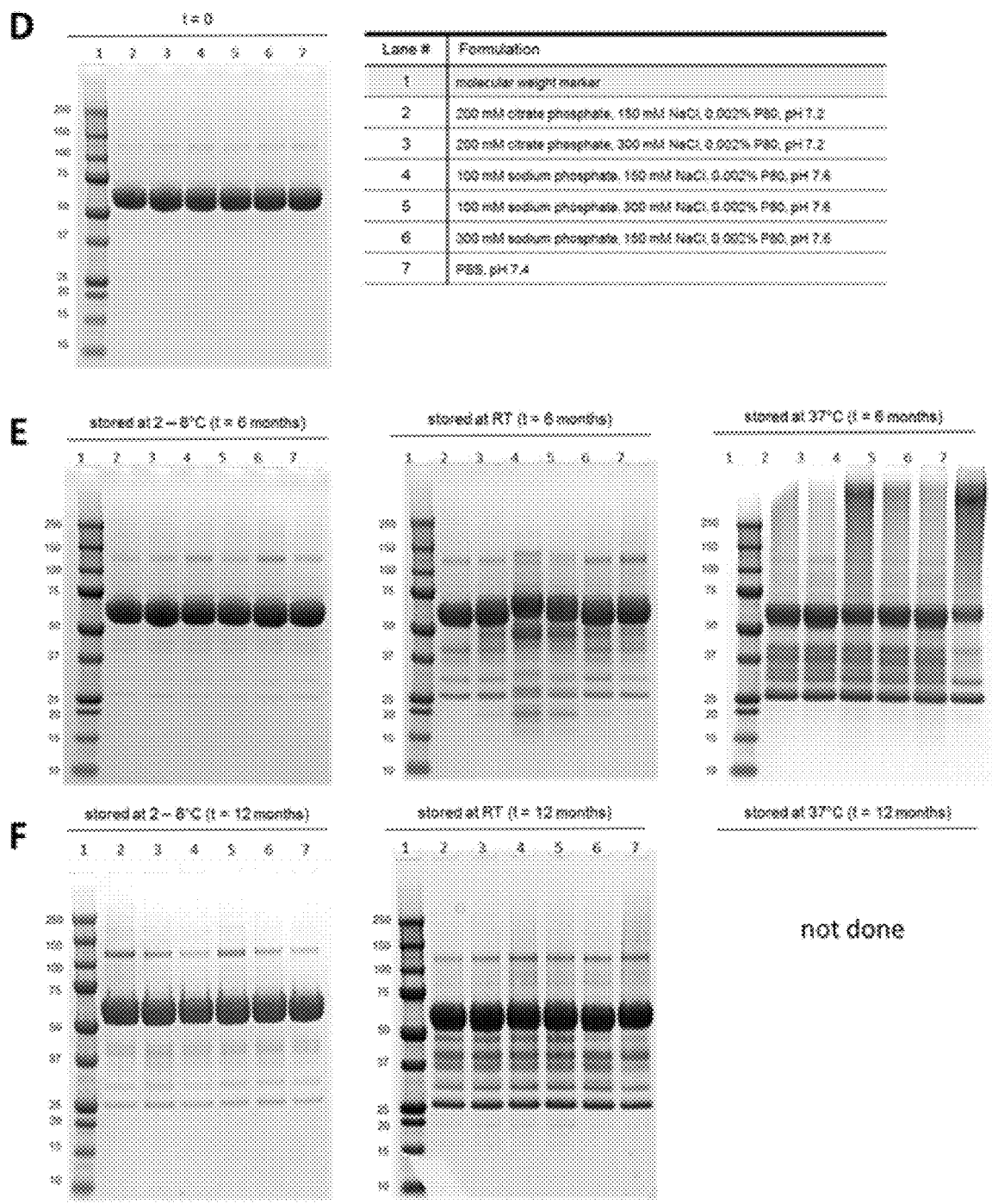

The stability of Hpx in these formulations was also analyzed by SDS-PAGE. From each formulation, a sample was taken at time zero and after 3 months and analyzed either by non-reduced or reduced SDS-PAGE for each storage temperature, as illustrated in FIG. 13. The data from the SDS-PAGE analyses were consistent with the SEC-HPLC results. At 2-8° C. storage, no additional bands or significant changes in band intensity were observed under reduced and non-reduced conditions. The samples stored at RT showed a band of low intensity at approximately 125 kDa, most probably reflecting the formation of Hpx dimers, and several low molecular weight bands, most prominently around 30 kDa and 20 kDa. These findings are in agreement with the fragment size determination by SLS in "aged and heat stressed" samples (see FIG. 3C). Under non-reduced SDS-PAGE, samples stored at 37° C. exhibited intense high molecular weight bands above 250 kDa, whereupon the intensity for each formulation correlated well with the detected aggregates by SEC-HPLC. Furthermore, a low-molecular weight band pattern as seen with the RT samples, but of increased intensity, was observed.

Figure 14:
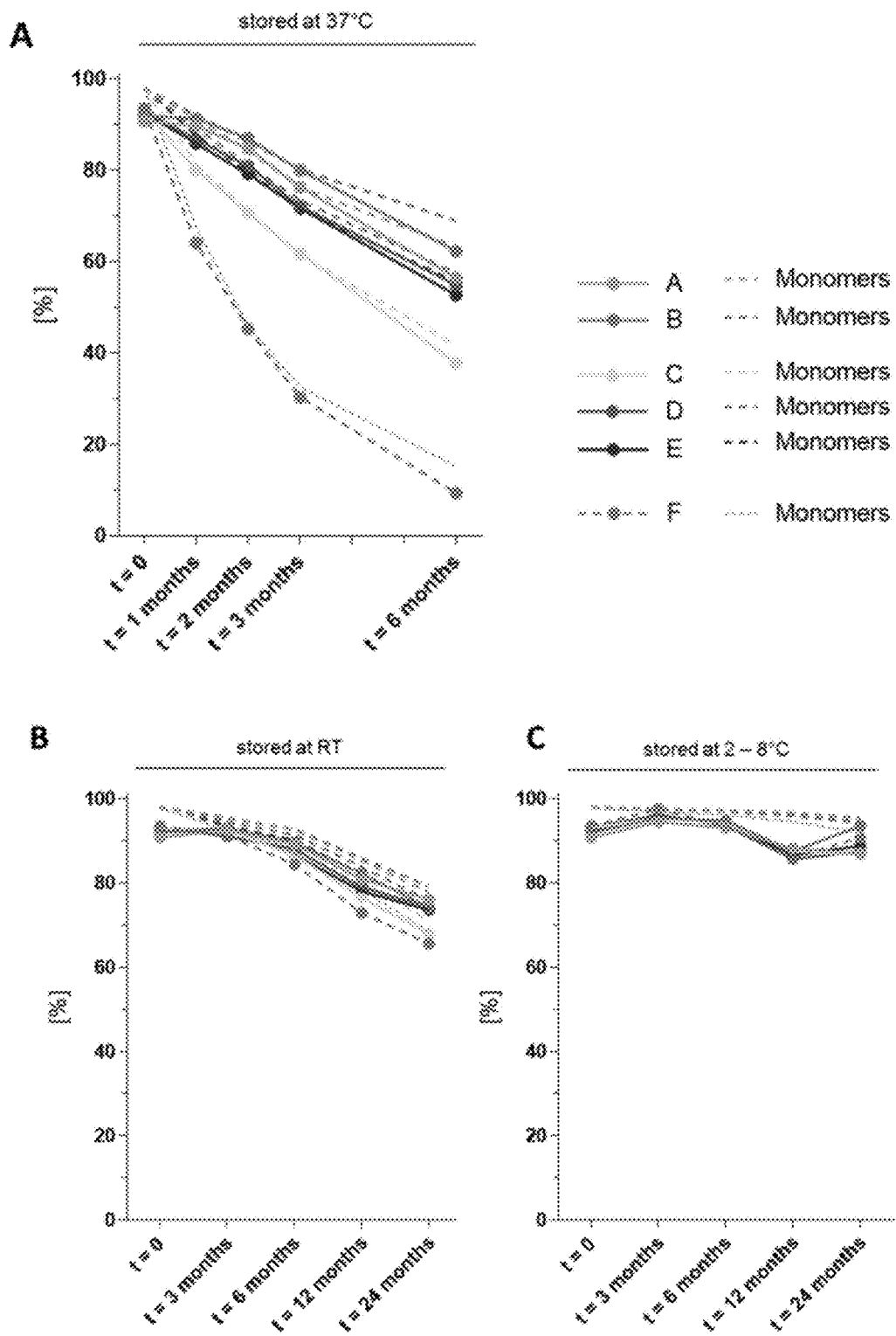
FIG. 14 shows heme binding to hemopexin. A-C: Heme binding shown in percentage at each time point (solid line) for samples stored at 2-8° C. (C), RT (B) and 37° C. (A). The corresponding percentage monomers at the given time points are shown in the same colour for each formulation (dashed lines); D: Overall correlation between heme binding and Hpx monomers. N=144, non-parametric Spearman correlation, r=0.83.
Figure 14:
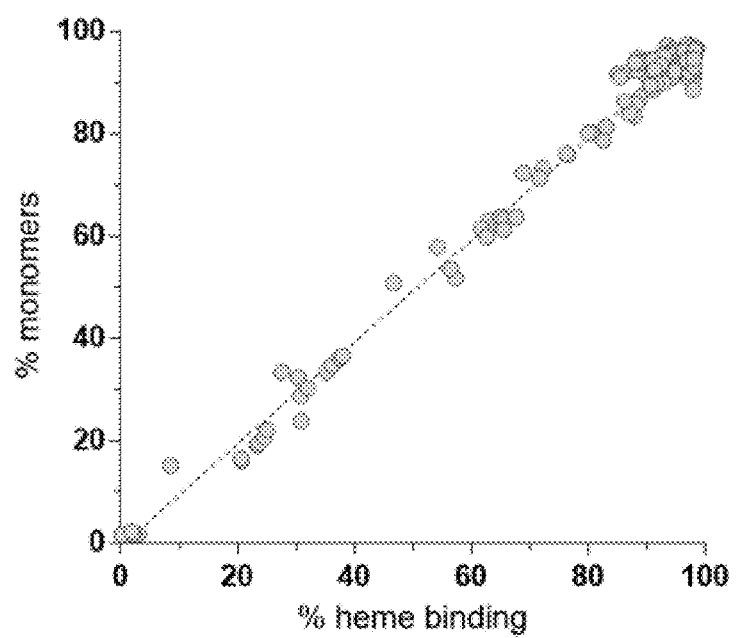

As a functional parameter, the heme binding of Hpx was assessed at each time point for each formulation. As is shown in FIG. 14, upon incubation at 37° C. the binding of hemopexin to heme decreased over time and this decrease correlated strongly with the corresponding Hpx monomer content (as determined by SEC-HPLC).

Figure 4:
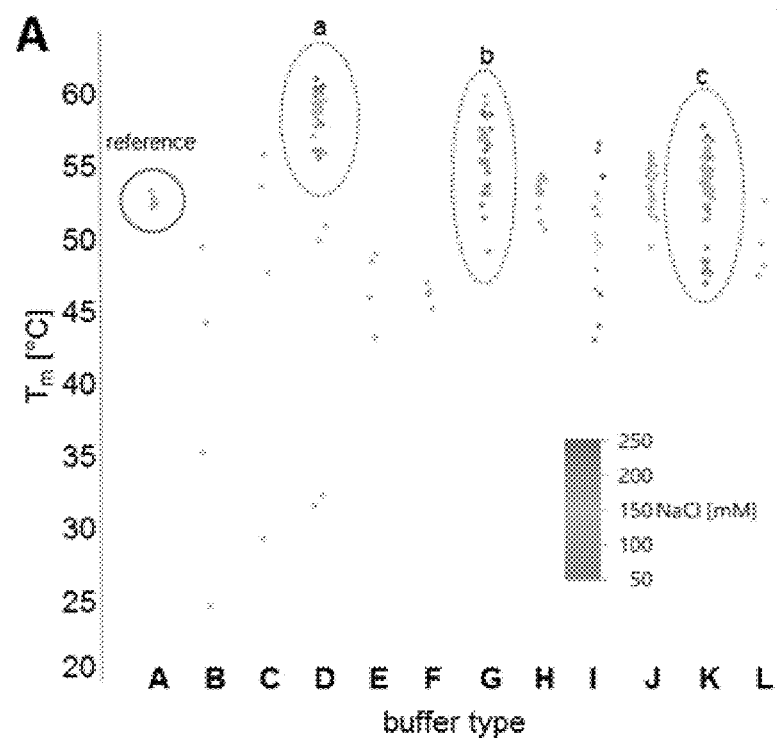
FIG. 4 shows the DSF data evaluation. A: Visualization of $T_m$ and the corresponding buffer types in a scatter plot. Buffer Type A (PBS, pH 7.4) serves as reference formulation. The different salt (NaCl) concentrations in the most stable buffers (dashed circles a-c) are highlighted by different shades of grey, where the lower data points within the dashed circles are representative of lower salt concentration (50-150 mM NaCl) and the higher data points within the dashed circles are representative of higher salt concentration (150-250 mM NaCl); (a) Citrate phosphate, (b) sodium phosphate, (c) glycine buffer. B: Visualization of the sodium chloride dependence of all conditions analyzed. Mean at each concentration is shown as a line. C: Density plot of $T_m$ against the pH; D: Visualization of $T_m$ and the corresponding salt (NaCl) concentrations in citrate phosphate formulated samples. PBS serves as reference formulation (asterix) and the 200 mM citrate phosphate, 150 mM NaCl is shown as an open circle. The different buffer strengths are highlighted by different shades of grey, with a decrease in buffer concentration from top to bottom (100 mM-15 mM citrate phosphate). Each condition was measured at least three times; error bars are indicating the standard deviation.
Figure 4:
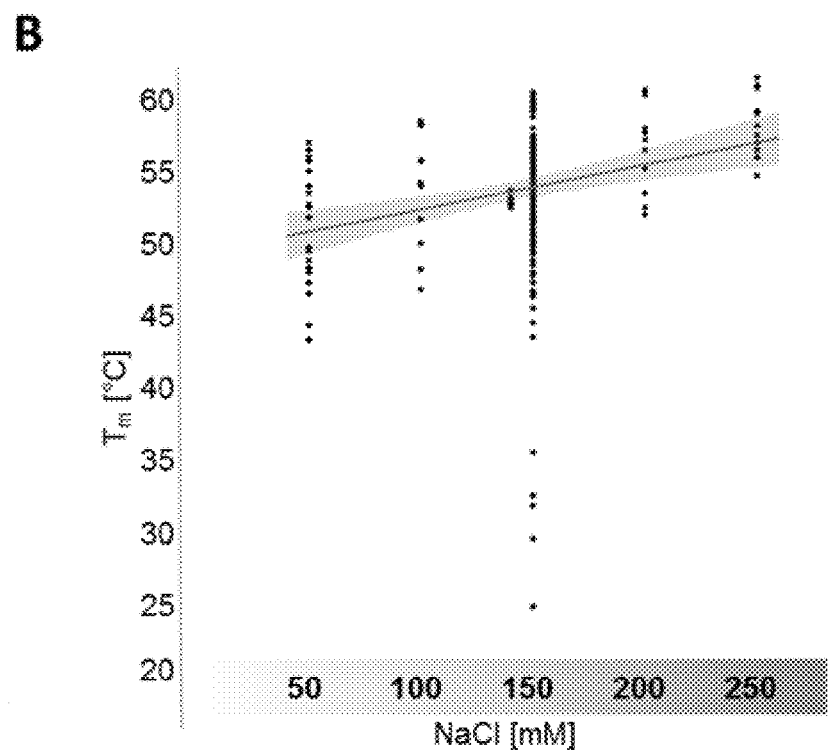
Figure 4:
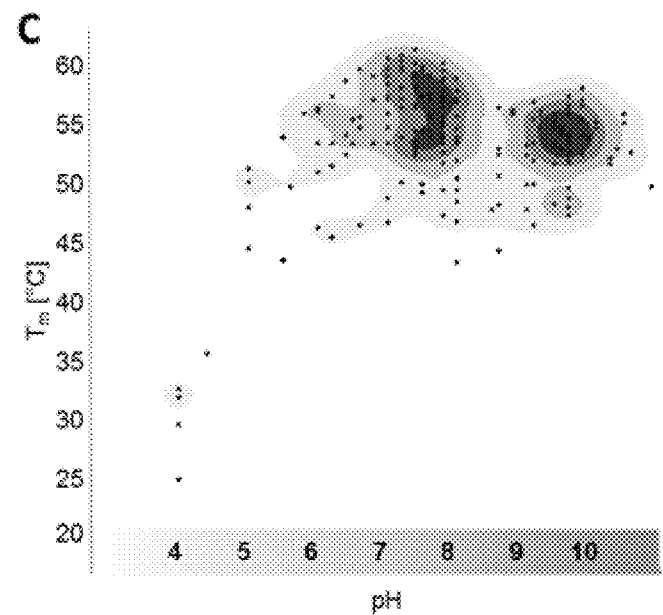
Figure 4:
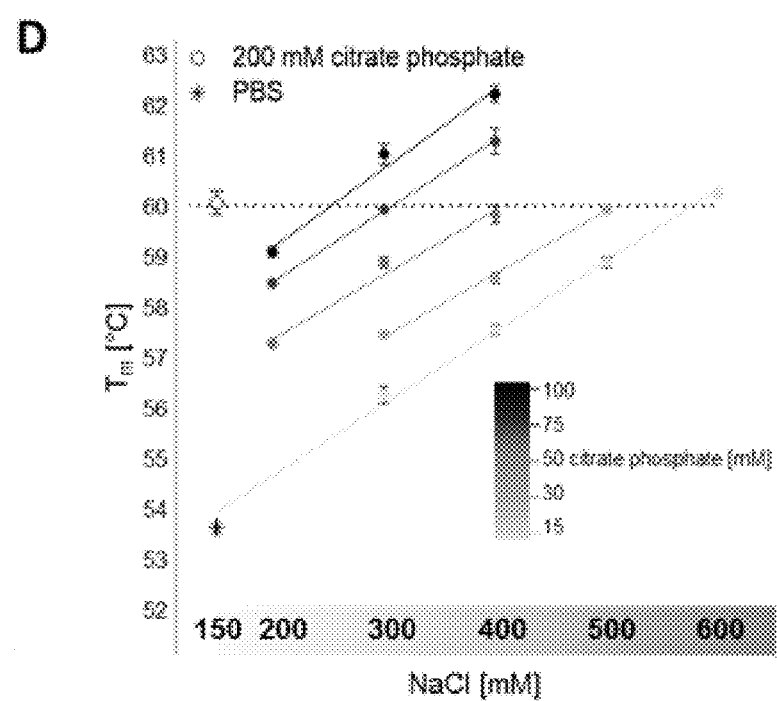

4.4. Stability Study: Lead Formulations with Lower Phosphate Concentration and Reduced Osmolarity Under accelerated conditions, the formulations (at a protein concentration of 10%) comprising (i) 200 mM citrate phosphate and 150 mM or (ii) 300 mM sodium chloride at pH 7.2 showed the greatest stability. Whilst their overall osmolarity (876 mOsm/L and 1176 mOsm/L, respectively) was high, they are still suitable for intravenous (i.v.) administration, noting that there are currently licensed drug products for i.v. application with formulations that have a comparably high osmolarity (i.e., 12% Sandoglobulin, 892.3 mOsm/L due to high sucrose concentration). Moreover, these drug products are infused at a much higher dosage (>100 mL/injection) than currently estimated for a Hpx product (i.e., <20-30 mL/injection). The DSF data suggest that there is a direct relationship between osmolarity and thermal stability, as shown in FIG. 4. To maintain equal thermal stability, a lower citrate phosphate concentration may be combined with a higher sodium chloride concentration, and vice versa. Although the results generated by DSF and the corresponding $T_m$ for each formulation are considered predictive in terms of the behaviour in short term stability studies under accelerated conditions (i.e., 37° C.), several Hpx solutions formulated with a lower excipient concentration were produced for three-month stability studies, as shown in Table 8 (1-5). All formulations were spiked with P80 to achieve a final P80 concentration of 0.01% and were stored for at least a 6-month time period protected from light at 2-8° C., RT (25° C.) or 37° C. At monthly time points, samples were taken from temperature storage and analyzed.

Figure 15:
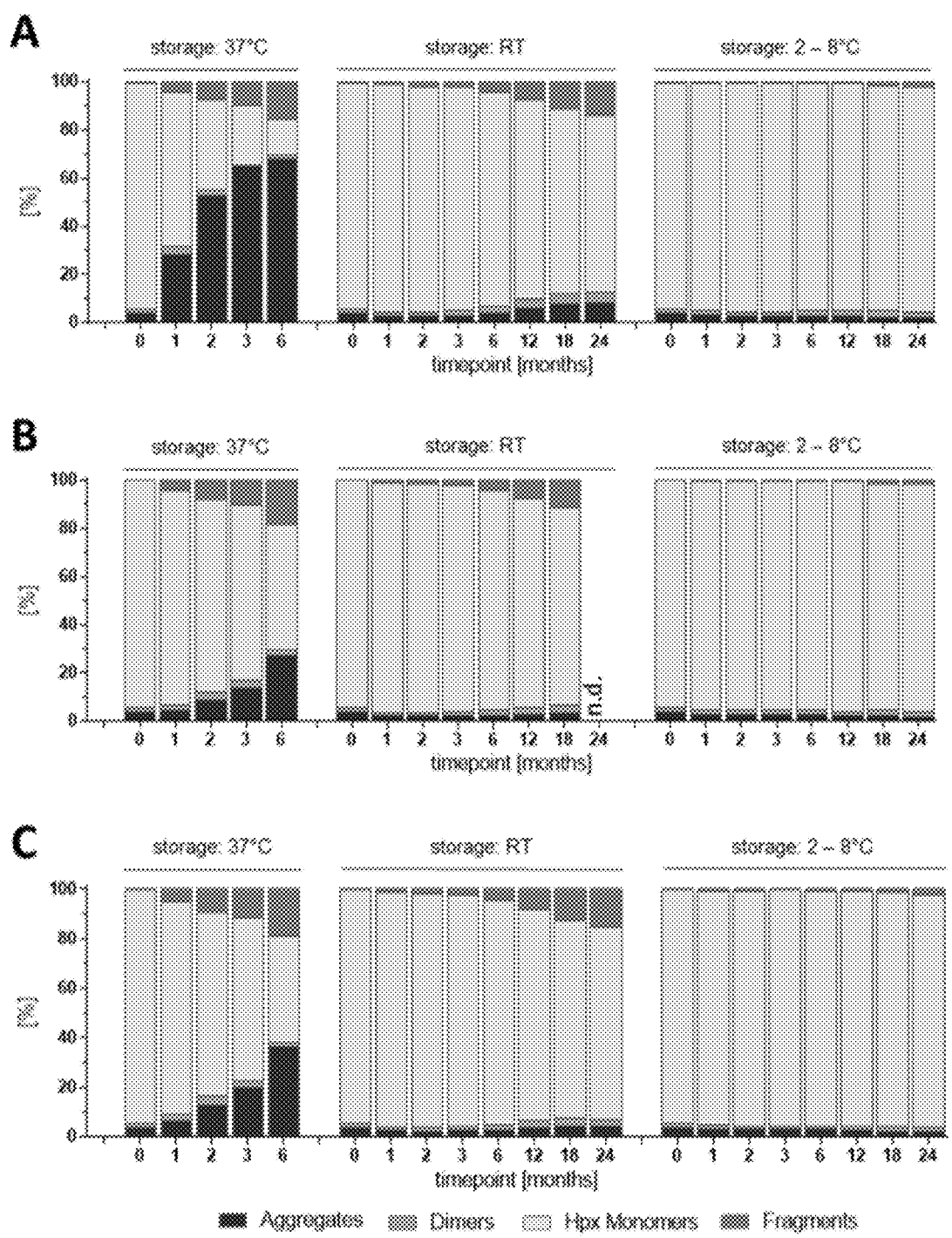
FIG. 15 shows the SEC-HPLC data of a 10% Hpx solution formulated with different buffers and analyzed over 6 months (stored at 37° C.) and 24 months (RT and 2-8° C. storage). A: 15 mM citrate phosphate, 150 mM NaCl, pH 7.2; B: 15 mM citrate phosphate, 300 mM NaCl, pH 7.2; C: 50 mM citrate phosphate, 200 mM NaCl, pH 7.2; D: 50 mM citrate phosphate, 400 mM NaCl, pH 7.2; E: 200 mM citrate phosphate, 150 mM NaCl, pH 7.2. All formulations contain 0.01% v/v P80. Molecular size distribution is presented as a 100% stacked column chart and each molecular species is shown as the respective amount in percentage. Aggregates and dimers are highlighted at the bottom of each column (black and grey, respectively); fragments are shown at the top of each column (grey).
Figure 15:
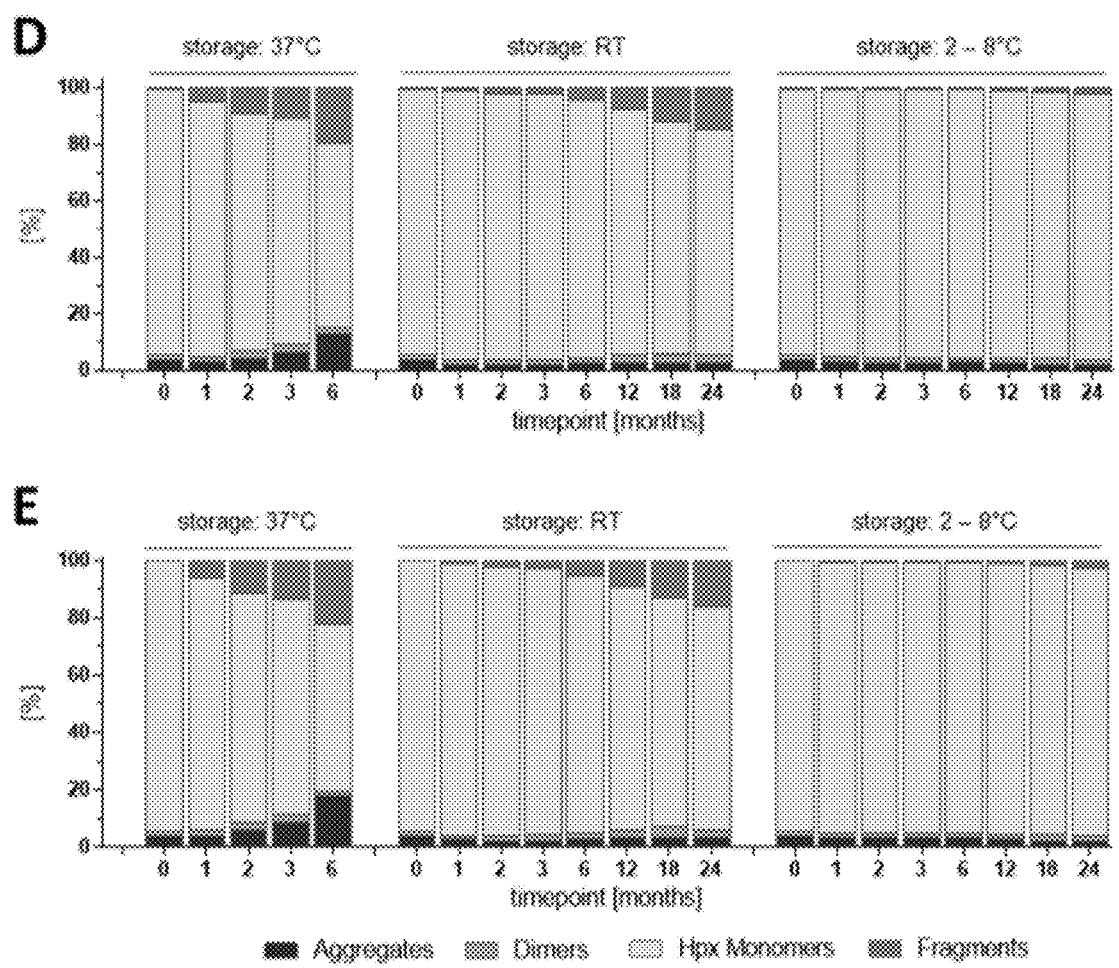

The molecular size distribution results for each formulation over a time period of at least 6 months are shown in Table 11 and FIG. 15. At 2-8° C., the content of monomeric Hpx (>93%) remained stable throughout the study period (24 months), and there are only minor differences at RT after 24 months. At the accelerating temperature of 37° C., each of the Hpx formulations showed a marked increase of aggregates and fragments over time. Large differences between the formulations were found regarding the aggregate content. Nearly isotonic formulations promoted aggregation, whereas hypertonic formulations seemed to stabilize the protein, as predicted by the former DSF analyses.

TABLE 11

SEC-HPLC data after storage at 37° C. for 6 months.

| No | Formulation | Aggregates [%] | Dimers [%] | Monomers [%] | Fragments [%] |
|---|---|---|---|---|---|
| | SEC-HPLC data after storage at 37° C. for 6 months | | | | |
| (1) | 15 mM citrate phosphate, 150 mM NaCl, 0.01% P80, pH 7.2 | 75.5 | 0.0 | 9.4 | 15.1 |
| (2) | 15 mM citrate phosphate, 300 mM NaCl, 0.01% P80, pH 7.2 | 27.3 | 2.1 | 52.1 | 18.5 |
| (3) | 50 mM citrate phosphate, 200 mM NaCl, 0.01% P80, pH 7.2 | 36.4 | 1.9 | 66.0 | 19.0 |
| (4) | 50 mM citrate phosphate, 400 mM NaCl, 0.01% P80, pH 7.2 | 13.1 | 1.9 | 65.3 | 19.8 |
| (5) | 200 mM citrate phosphate, 150 mM NaCl, 0.01% P80, pH 7.2 | 18.0 | 1.6 | 58.2 | 22.2 |
| | SEC-HPLC data after storage at RT for 9 months | | | | |
| (1) | 15 mM citrate phosphate, 150 mM NaCl, 0.01% P80, pH 7.2 | 4.8 | 3.2 | 85.1 | 6.9 |
| (2) | 15 mM citrate phosphate, 300 mM NaCl, 0.01% P80, pH 7.2 | 2.7 | 2.4 | 88.4 | 6.6 |
| (3) | 50 mM citrate phosphate, 200 mM NaCl, 0.01% P80, pH 7.2 | 3.0 | 2.4 | 87.4 | 7.2 |
| (4) | 50 mM citrate phosphate, 400 mM NaCl, 0.01% P80, pH 7.2 | 2.4 | 2.3 | 88.4 | 6.9 |
| (5) | 200 mM citrate phosphate, 150 mM NaCl, 0.01% P80, pH 7.2 | 2.9 | 2.5 | 86.3 | 8.3 |

TABLE 11-continued

SEC-HPLC data after storage at 37° C. for 6 months.

| No | Formulation | Aggregates [%] | Dimers [%] | Monomers [%] | Fragments [%] |
|---|---|---|---|---|---|
| | SEC-HPLC data after storage at 2-8° C. for 9 months | | | | |
| (1) | 15 mM citrate phosphate, 150 mM NaCl, 0.01% P80, pH 7.2 | 2.9 | 1.8 | 94.2 | 1.1 |
| (2) | 15 mM citrate phosphate, 300 mM NaCl, 0.01% P80, pH 7.2 | 2.6 | 1.6 | 94.8 | 1.0 |
| (3) | 50 mM citrate phosphate, 200 mM NaCl, 0.01% P80, pH 7.2 | 2.7 | 1.5 | 94.7 | 1.1 |
| (4) | 50 mM citrate phosphate, 400 mM NaCl, 0.01% P80, pH 7.2 | 2.7 | 1.6 | 94.7 | 1.1 |
| (5) | 200 mM citrate phosphate, 150 mM NaCl, 0.01% P80, pH 7.2 | 3.0 | 1.7 | 93.9 | 1.3 |
| | SEC-HPLC data after storage at 2-8° C. for 24 months | | | | |
| (1) | 15 mM citrate phosphate, 150 mM NaCl, 0.01% P80, pH 7.2 | 2.2 | 2.3 | 93.3 | 2.2 |
| (2) | 15 mM citrate phosphate, 300 mM NaCl, 0.01% P80, pH 7.2 | 1.9 | 2.3 | 93.9 | 1.9 |
| (3) | 50 mM citrate phosphate, 200 mM NaCl, 0.01% P80, pH 7.2 | 2.0 | 1.8 | 93.8 | 2.4 |
| (4) | 50 mM citrate phosphate, 400 mM NaCl, 0.01% P80, pH 7.2 | 1.9 | 1.9 | 94.2 | 2.0 |
| (5) | 200 mM citrate phosphate, 150 mM NaCl, 0.01% P80, pH 7.2 | 2.2 | 2.0 | 93.0 | 2.8 |

Figure 16:
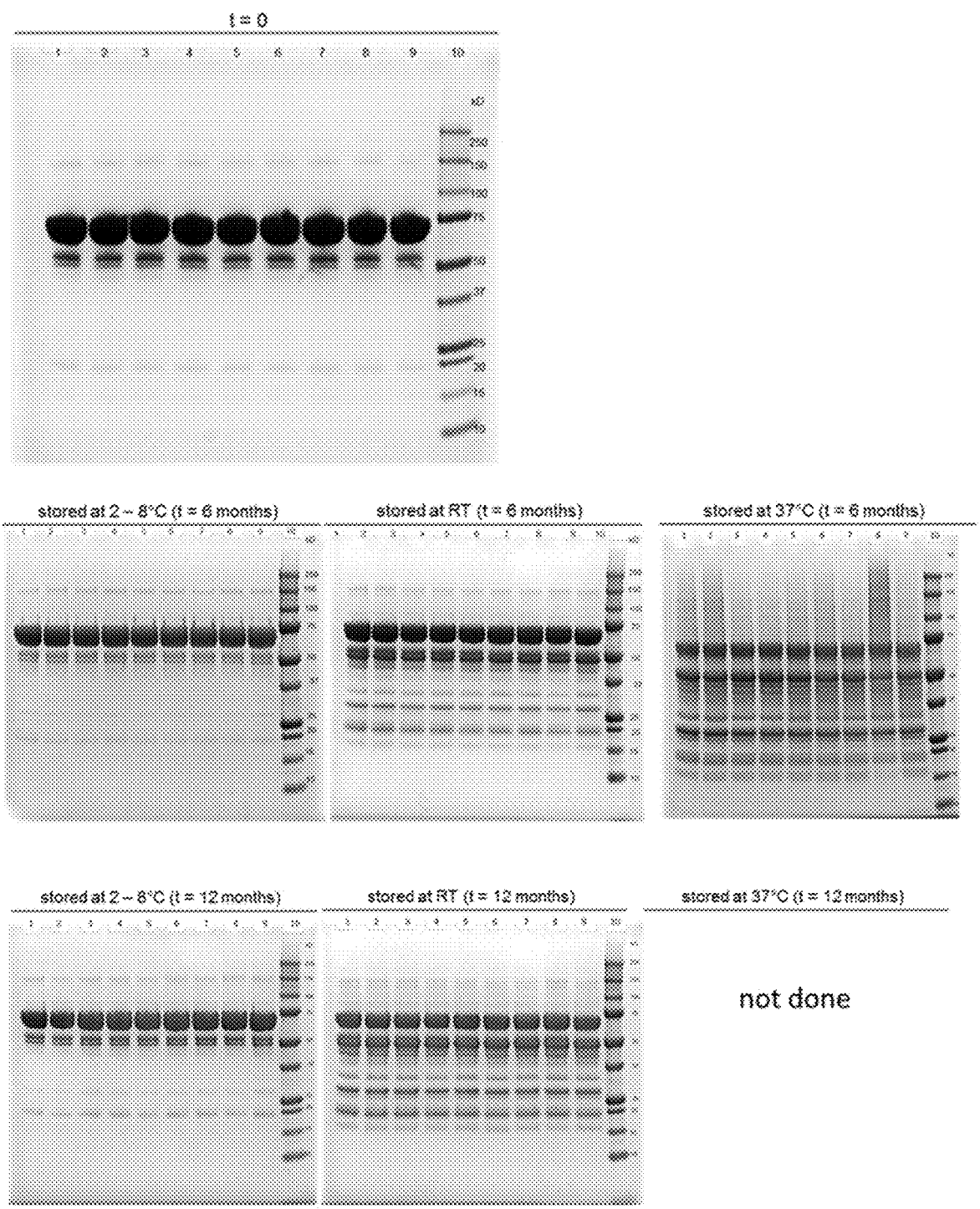
FIG. 16 shows photographs of SDS-PAGE gels with samples from time zero, 6 and 12 months. Samples were analyzed under reducing conditions (500 mM dithiothreitol, DTT). 15 µg protein was loaded into each lane. Each formulation was analyzed at time zero (upper left), 6- and 12-months storage as indicated. Molecular weight marker is shown in right lane, kDa values, as indicated in the figure; Lane 1—15 mM citrate phosphate, 300 mM NaCl, 0.01% P80, pH 7.2; Lane 2—50 mM citrate phosphate, 200 mM NaCl, 0.01% P80, pH 7.2; Lane 3—50 mM citrate phosphate, 400 mM NaCl, 0.01% P80, pH 7.2; Lane 4—30 mM citrate phosphate, 500 mM NaCl, 0.01% P80, pH 7.2; Lane 5—75 mM citrate phosphate, 300 mM NaCl, 0.01% P80, pH 7.2; Lane 6—100 mM citrate phosphate, 200 mM NaCl, 0.01% P80, pH 7.2; Lane 7—100 mM citrate phosphate, 400 mM NaCl, 0.01% P80, pH 7.2; Lane 8—15 mM citrate phosphate, 150 mM NaCl, 0.01% P80, pH 7.2; Lane 9—200 mM citrate phosphate, 150 mM NaCl, 0.01% P80, pH 7.2; Lane 10—molecular weight marker.
Figure 17:
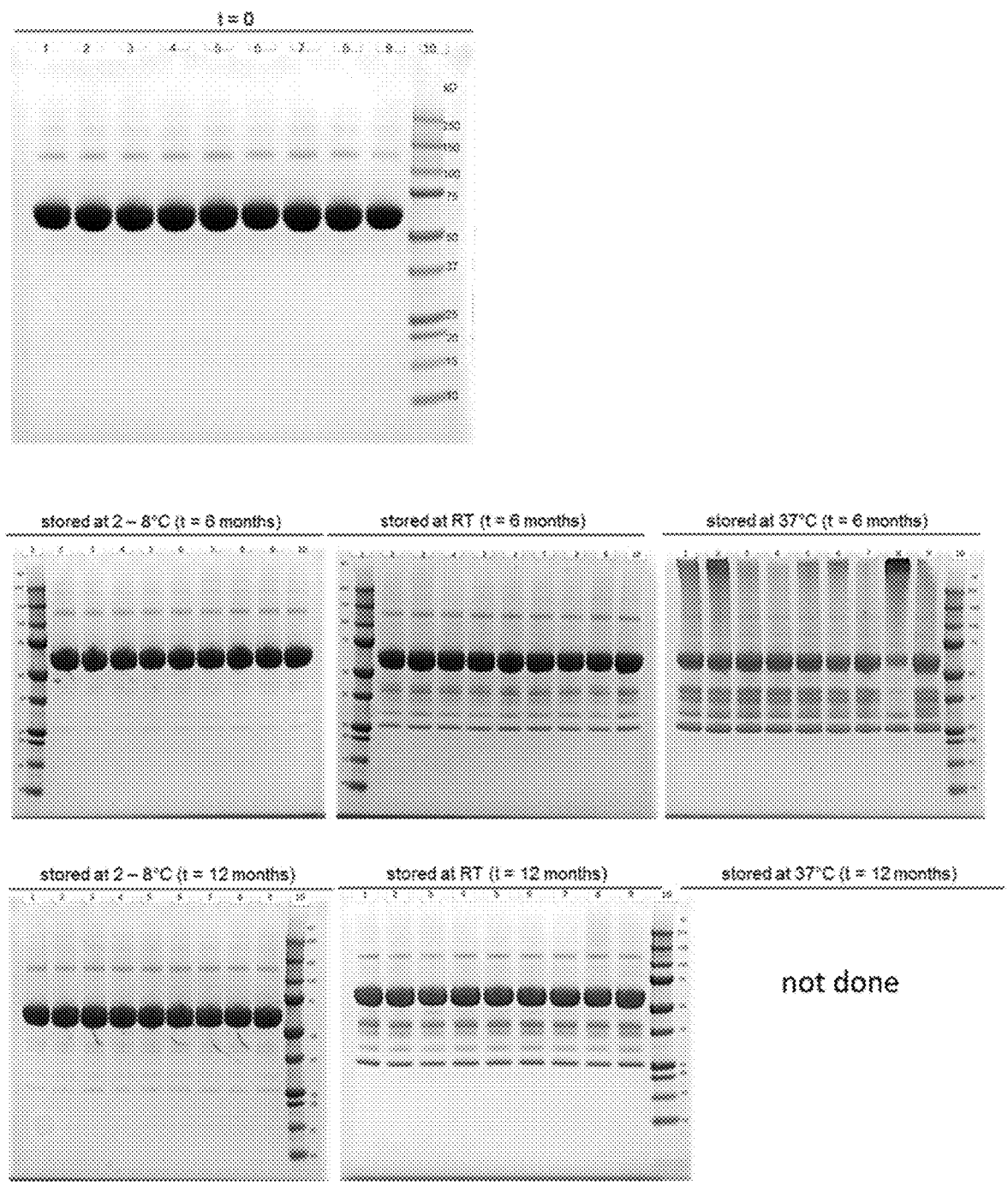
FIG. 17 shows photographs of SDS-PAGE gels with samples from time zero, 6 and 12 months. Samples were analyzed under non-reducing conditions. 15 µg protein was loaded into each lane. Each formulation was analyzed at time zero (upper left) 6- and 12-months storage as indicated. Molecular weight marker is shown in right lane, kDa values, as indicated in the figure; Lane 1—15 mM citrate phosphate, 300 mM NaCl, 0.01% P80, pH 7.2; Lane 2—50 mM citrate phosphate, 200 mM NaCl, 0.01% P80, pH 7.2; Lane 3—50 mM citrate phosphate, 400 mM NaCl, 0.01% P80, pH 7.2; Lane 4—30 mM citrate phosphate, 500 mM NaCl, 0.01% P80, pH 7.2; Lane 5—75 mM citrate phosphate, 300 mM NaCl, 0.01% P80, pH 7.2; Lane 6—100 mM citrate phosphate, 200 mM NaCl, 0.01% P80, pH 7.2; Lane 7—100 mM citrate phosphate, 400 mM NaCl, 0.01% P80, pH 7.2; Lane 8—15 mM citrate phosphate, 150 mM NaCl, 0.01% P80, pH 7.2; Lane 9—200 mM citrate phosphate, 150 mM NaCl, 0.01% P80, pH 7.2; Lane 10—molecular weight marker.

The aforementioned Hpx formulations were also analyzed by SDS-PAGE for each formulation content and storage temperature. A sample was taken at time zero and after 3 months and analyzed either by reducing (FIG. 16) and non-reducing (FIG. 17) SDS-PAGE, respectively. The data from these analyses were consistent with the SEC-HPLC results. At 2-8° C. storage, slight changes in terms of additional bands were observed, both under reduced and non-reduced conditions. The samples stored at RT showed a weakly increased intensity of the faint band at approximately 125 kDa, a stronger increase of bands around 50 kDa and several additional low molecular bands between 20 kDa and 40 kDa. Finally, samples stored at 37° C. exhibited pronounced high molecular weight bands the intensities of which correlated well with the aggregate content as determined by SEC-HPLC, as well as additional low molecular weight bands (observed already, though with lower band intensity, with the samples stored at RT).

Figure 18:
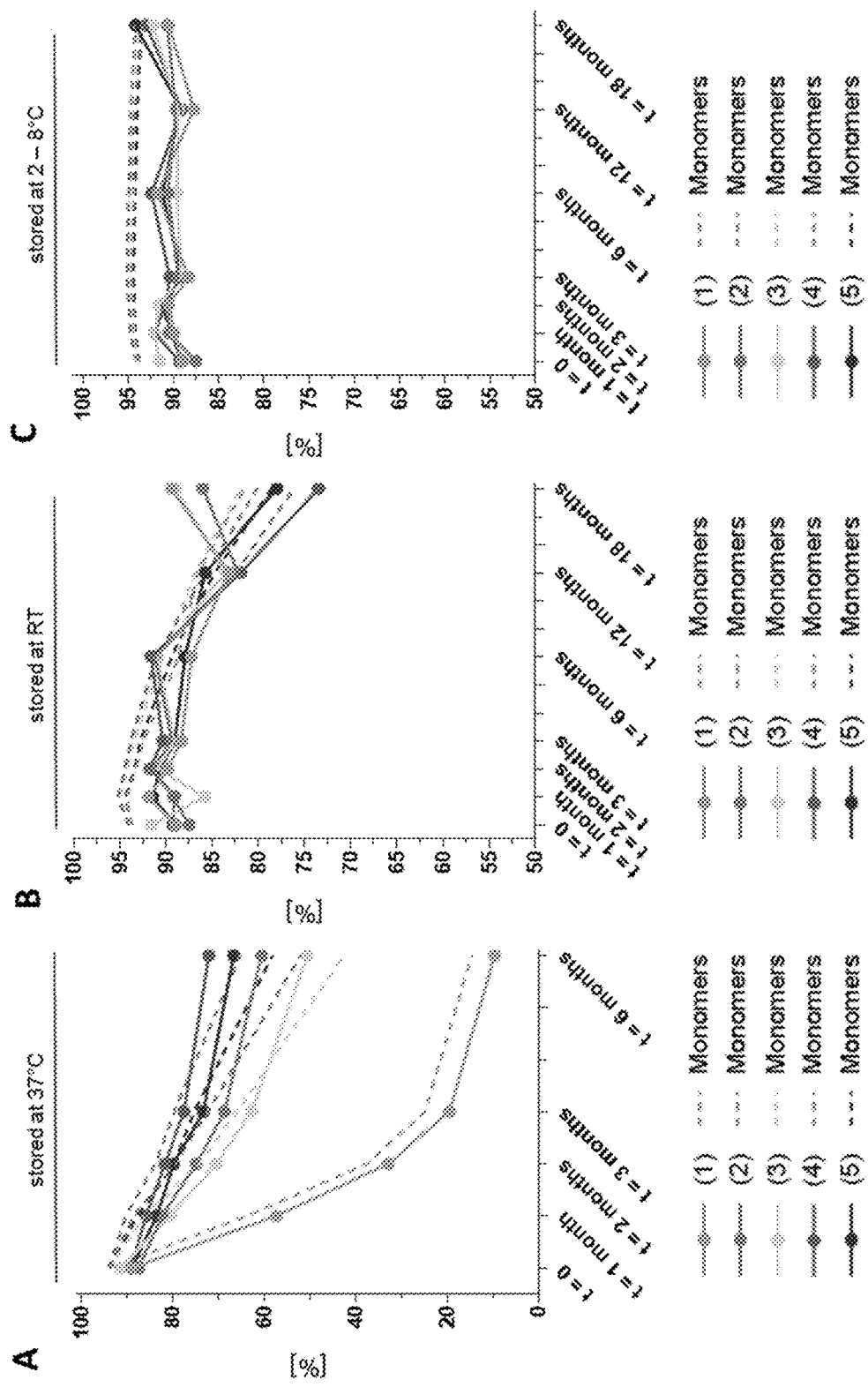
FIG. 18 shows heme binding to hemopexin. Heme binding shown in percentage at each time point (solid line) for samples stored at 37° C. (A), RT (B) and 2-8° C. (C). The corresponding percentage monomers at the given time points are shown in the same colour for each formulation (dashed lines).

The heme binding capability of Hpx as a functional parameter was also assessed at each time point for each storage temperature condition. As seen before with other formulations, the binding of hemopexin to heme correlated well with the corresponding Hpx monomer content (as determined by SEC-HPLC) and markedly decreased during storage at 37° C. (FIG. 18).

4.5. Short Term Stability Study—Reproducibility

To further generate a data set for the definition of a lead formulation for human Hpx, the two most stable formulations identified were prepared with two new Hpx batches, as described above, to check for reproducibility and any batch-to-batch variability. Samples were stored at 37° C. and analyzed by SEC-HPLC and heme binding assays.

As shown in Tables 12-14, below, the results derived from the two formulations based on citrate phosphate were comparable at all time points analyzed, demonstrating robust analytical reproducibility as well as batch-to-batch consistency.

TABLE 12

Hpx formulated in PBS, pH 7.4. Mean of SEC-HPLC data derived from different Hpx batches (TO294063, TO290102 and TO294001 + TO294023) stored over a time period of three months at 37° C. N = 4.

| time point [month] | Aggregates mean [%] | StDev | Dimers mean [%] | StDev | Monomers mean [%] | StDev | Fragments mean [%] | StDev |
|---|---|---|---|---|---|---|---|---|
| 0 | 0.8 | 0.1 | 0.7 | 0.1 | 98.1 | 0.3 | 0.4 | 0.0 |
| 1 | 24.4 | 1.5 | 4.1 | 0.7 | 67.0 | 1.2 | 4.5 | 0.2 |
| 2 | 50.7 | 6.6 | 2.8 | 0.8 | 38.9 | 6.2 | 7.7 | 0.4 |
| 3 | 62.3 | 6.6 | 2.1 | 0.9 | 25.6 | 6.0 | 10.0 | 0.2 |

| time point [month] | Heme binding | |
|---|---|---|
| | mean [%] | StDev |
| 0 | 95.4 | 1.7 |
| 1 | 63.0 | 1.5 |
| 2 | 35.6 | 8.5 |
| 3 | 21.0 | 8.1 |

TABLE 13

Hpx formulated in 200 mM citrate phosphate, 300 mM NaCl, 0.002%
P80, pH 7.2. Mean of SEC-HPLC data derived from different
Hpx batches (TO294063, TO290102 and TO294001 + TO294023)
stored over a time period of three months at 37° C. N = 3.

| time point [month] | Aggregates mean [%] | StDev | Dimers mean [%] | StDev | Monomers mean [%] | StDev | Fragments mean | StDev [%] |
|---|---|---|---|---|---|---|---|---|
| 0 | 0.7 | 0.1 | 0.7 | 0.1 | 98.2 | 0.2 | 0.4 | 0.0 |
| 1 | 1.2 | 0.2 | 1.6 | 0.1 | 91.6 | 0.5 | 5.6 | 0.6 |
| 2 | 2.1 | 0.3 | 2.1 | 0.2 | 85.4 | 0.8 | 10.4 | 1.2 |
| 3 | 3.7 | 0.5 | 2.2 | 0.4 | 80.8 | 0.3 | 13.3 | 0.6 |

| time point [month] | Heme binding mean [%] | StDev |
|---|---|---|
| 0 | 94.9 | 2.6 |
| 1 | 90.3 | 0.8 |
| 2 | 85.0 | 1.7 |
| 3 | 78.2 | 1.7 |

TABLE 14

Hpx formulated in 200 mM citrate phosphate, 150 mM NaCl, 0.002%
P80, pH 7.2. Mean of SEC-HPLC data derived from different
Hpx batches (TO294063, TO290102 and TO294001 + TO294023)
stored over a time period of three months at 37° C. N = 3.

| time point [month] | Aggregates mean [%] | StDev | Dimers mean [%] | StDev | Monomers mean [%] | StDev | Fragments StDev | mean [%] |
|---|---|---|---|---|---|---|---|---|
| 0 | 0.7 | 0.1 | 0.6 | 0.1 | 98.2 | 0.2 | 0.4 | 0.0 |
| 1 | 1.5 | 0.3 | 1.6 | 0.1 | 91.0 | 0.3 | 6.0 | 0.6 |
| 2 | 3.6 | 0.3 | 2.0 | 0.2 | 83.4 | 0.7 | 10.9 | 1.2 |
| 3 | 6.3 | 1.1 | 2.2 | 0.5 | 77.6 | 1.2 | 14.0 | 0.5 |

| time point [month] | Heme binding mean [%] | StDev |
|---|---|---|
| 0 | 94.3 | 3.1 |
| 1 | 89.3 | 0.6 |
| 2 | 82.2 | 2.3 |
| 3 | 75.2 | 1.0 |

Example 5. Hpx Stability in Tris Buffer

Following hemopexin purification, the protein solution was concentrated and diafiltered into PBS, pH 7.5 for storage. In preparation for a chromatography step for solvent detergent removal, hemopexin was diafiltered into 50 mM Tris buffer, noting that the presence of salt in the PBS could have interfered with hemopexin binding in the Capto Q strong anion exchange resin that was to be used for solvent detergent removal. 50 mM Tris, pH 7.4 was chosen as the hemopexin storage buffer as to not interfere with this chromatography step.

Two batches of hemopexin, TO302001 and T0294131, were prepared in 50 mM Tris buffer, pH 7.5. Upon SEC-HPLC analysis, significant protein aggregation was evident in these Tris buffered hemopexin batches. A summary of the monomer content, as determined by SEC-HPLC analysis for several hemopexin batches in PBS as well as the two batches in Tris, is shown in Table 15 below. As shown by the results in Table 15, there was a significant drop in the amount of Hpx monomer in the Tris buffered Hpx batches when compared to the PBS buffered Hpx batches. The reduction in monomer content was associated with increased presence of multiple high molecular weight peaks that are not normally present in Hpx preparations.

TABLE 15

SEC-HPLC Analysis of Hemopexin Final Concentrates

| Hemopexin Batch | Production Date | Buffer | % Monomer |
|---|---|---|---|
| TO294001 | Mar. 31, 2015 | PBS, pH 7.5 | 98.78 |
| TO294023 | Apr. 4, 2015 | PBS, pH 7.5 | 98.58 |
| TO294063 | May 1, 2015 | PBS, pH 7.5 | 98.46 |
| TO290235 | May 29, 2015 | PBS, pH 7.5 | 98.00 |
| TO302001 | Jun. 18, 2015 | 50 mM Tris, pH 7.5 | 65.15 |
| TO294131 | Jul. 31, 2015 | 50 mM Tris, pH 7.5 | 65.84 |

Hemopexin stability in different buffers was further investigated using dialysis and SEC-HPLC analysis for two different Hpx batches. A sample of Hpx batch TO302001 stored in 50 mM Tris was dialyzed into PBS to determine whether protein aggregation is reversible after storage in Tris buffer. Samples of Hpx batch TO290235 stored in PBS was dialyzed into 50 mM Tris and also into 20 mM sodium phosphate pH 7.5 to determine if dialysis in PBS before dialysis in Tris or 20 mM sodium phosphate buffer would prevent Hpx aggregation. The results from this study are presented in Table 16, below.

TABLE 16

Hemopexin stability in Tris, PBS, and sodium phosphate buffers

| Hemopexin Batch | Initial Storage Buffer | Dialysis Buffer | % Monomer |
|---|---|---|---|
| TO302001 | 50 mM Tris, pH 7.5 | PBS, pH 7.5 | 68.39 |
| TO290235 | PBS, pH 7.5 | 50 mM Tris, pH 7.5 | 70.25 |
| TO 290235 | PBS, pH 7.5 | 20 mM sodium phosphate, pH 7.5 | 96.92 |

Dialysis of Tris buffered Hpx into PBS did not appear to reverse protein aggregation. Dialysis of PBS buffered hemopexin into 50 mM Tris buffer displayed protein aggregation similar to the two Hpx batches that were previously stored in Tris. Dialysis of PBS buffered Hpx into sodium phosphate displayed higher Hpx monomer content. These results show that 20 mM sodium phosphate, pH 7.5 is a suitable low salt Hpx buffer alternative for use with Capto Q resin for solvent detergent removal.

To determine whether or not the presence of nickel from the immobilized metal affinity chromatography (IMAC) column used for Hpx purification may be attributing to Hpx aggregation in the presence of Tris buffer, several samples of Hpx were incubated with various EDTA solutions (TO303011 and TO303030). Table 17, below, provides a summary of the SEC-HPLC data obtained after the EDTA incubations.

TABLE 17

Monomer content of HPX batch TO302001 after EDTA incubation

| Buffer Condition | % Monomer |
|---|---|
| T0302001 Untreated | 49.93 |
| 10 mM EDTA, pH 7.4 | 52.88 |
| 20 mM EDTA, pH 7.4 | 54.39 |
| 30 mM EDTA, pH 7.4 | 55.88 |
| 40 mM EDTA, pH 7.4 | 57.30 |
| 50 mM EDTA, pH 7.4 | 58.71 |
| 100 mM EDTA, pH 7.4 | 77.10 |
| 200 mM EDTA, pH 7.4 | 75.69 |
| 100 mM EDTA/PBS, pH 7.4 | 81.71 |
| 100 mM EDTA Dialysis | 81.29 |

The results show that the presence of nickel has little effect on Hpx aggregation in the presence of Tris buffer.

Hemopexin stability in Tris buffer was further examined to determine if nickel removal prior to dialysis in Tris would result in less Hpx aggregation. To this end, an additional diafiltration step was implemented in the Hpx purification process to remove nickel from the Hpx solution utilizing 100 mM EDTA, pH 7.4. Three samples from Hpx batch TO294179, at various process steps, were dialyzed into 50 mM Tris buffer, pH 7.5. The SEC-HPLC results are presented in Table 18, below.

TABLE 18

Hemopexin stability in 50 mM Tris, post-EDTA dialysis

| Hemopexin Sample | % Monomer |
|---|---|
| IMAC Eluate | 89.95 |
| IMAC Eluate - after EDTA dialysis | 80.88 |
| Final Concentrate - after EDTA dialysis | 58.92 |

The results show that all three samples that were dialyzed into 50 mM Tris buffer, pH 7.5 displayed Hpx aggregation and there was an increase in Hpx aggregation following EDTA dialysis. The increase in Hpx aggregation following EDTA dialysis does not appear to be attributed to the presence of nickel, noting that the absence of nickel still resulted in Hpx aggregation once exchanged into the 50 mM Tris buffer. The results suggest that, in some instances, 50 mM Tris buffer, pH 7.5 should be avoided as a storage buffer due to the potential for Hpx aggregation. Further stability studies have confirmed reduced Hpx stability in Tris buffer, except when high levels of NaCl are present. Alternative buffers may need to be evaluated to minimise Hpx yield loss and aggregation in the presence of Tris buffer.

Example 6. Hpx Stability at Higher Protein Concentrations 6.1 Sample Preparation For the reported formulation development, Hpx was purified from human plasma (Kistler-Cohn Fraction IV). Purification process details are described elsewhere [6]. Purified Hpx was provided in PBS, pH 7.4, at a protein concentration of 3-4%. Higher-concentrated (up to 30%) Hpx formulations for stress induced stability studies were obtained by ultra and diafiltration with an Äkta flux device (GE Healthcare) using a 10 kD MW cut-off filtration cassette (PES, 50 cm2, PALL Life Sciences).

6.2 Methods for Stability Assessment and Indicative Protein Characterization 6.2.1 ΔG and ΔG Trend The ΔG and ΔG Trend were measured using a HUNK, which is a chemical denaturation system from Unchained Laboratories. Samples were denatured using a 36-point denaturation curve in 0-8M urea. To calculate ΔG, data were fit using the intrinsic fluorescence wavelength ratio of the native and fully denatured Hpx. Delta G trends were determined by measuring the ΔG at ten different Hpx concentrations: 0.25, 1, 5, 10, 25, 50, 100, 200, 250 and 300.0 mg/mL. Results were expressed as ΔG or ΔΔG for the trends.

6.2.2 Other Assays for Characterization

Table 19 summarizes all other assays and procedures used for further investigation of Hpx stability and protein characterization.

TABLE 19

Assays to assess Hemopexin stability and characterization

| Assay | Unit | Methods | Procedure |
|---|---|---|---|
| Molecular size distribution | % | SEC-HPLC | Column: Diol 300, Flow 1.0 mL/min |
| Protein | g/L | A280 | laboratory protocol |
| Viscosity | mPa*s | Rheometer | laboratory protocol |

6.3 Stability Studies at High Protein Concentration 6.3.1 Formulation Preparation The following lead formulations were further investigated at higher protein concentrations of Hpx and subsequently analyzed under accelerated storage conditions (37° C.), long term storage (2-8° C.):
Formulation 1: 200 mM citrate phosphate, 150 mM NaCl, 0.01% P80, pH 7.2;
Formulation 2: 50 mM citrate phosphate, 400 mM NaCl, 0.01% P80, pH 7.2;
Formulation 3: 15 mM citrate phosphate, 150 mM NaCl, 0.01% P80, pH 7.2;
Formulation 4: PBS, 0.01% P80, pH 7.4.

The formulations were further characterized by performing chemical denaturation studies and thermal stability investigations. Briefly, Hpx formulated in PBS was concentrated to 30% Hpx and diafiltrated into the desired buffer and excipient compositions as shown in Table 20. pH adjustments were performed by carefully titrating 0.2 M HCl or 0.2 M NaOH if necessary. Afterwards, the different formulations were diluted to the desired concentrations with formulation buffer. Finally, each formulation was sterile filtered, filled into sterile glass vials and stored at different temperatures for subsequent analysis at time points 0, 1, 2, 3 and 6 months or as otherwise indicated.

TABLE 20

Overview of the different Hpx lead formulations and their compositions and characteristics

| No | Buffer | NaCl [mM] | pH | P80 [%] | osmolarity [mOsm/L]§ | Target g/L | viscosity [mPa*s] |
|---|---|---|---|---|---|---|---|
| | Short term stability study: lead formulations at increased protein concentrations (Hpx stability study 8) | | | | | | |
| 1_1 | 200 mM citrate phosphate | 150 | 7.2 | 0.01 | 876 | 300 | 31.4 |
| 1_2 | 200 mM citrate phosphate | 150 | 7.2 | 0.01 | 876 | 250 | 15.5 |
| 1_3 | 200 mM citrate phosphate | 150 | 7.2 | 0.01 | 876 | 200 | 6.9 |
| 1_4 | 200 mM citrate phosphate | 150 | 7.2 | 0.01 | 876 | 100 | 3.2 |
| 2_1 | 50 mM citrate phosphate | 400 | 7.2 | 0.01 | 944 | 300 | 26.1 |
| 2_2 | 50 mM citrate phosphate | 400 | 7.2 | 0.01 | 944 | 250 | 11.9 |
| 2_3 | 50 mM citrate phosphate | 400 | 7.2 | 0.01 | 944 | 200 | 6.4 |
| 2_4 | 50 mM citrate phosphate | 400 | 7.2 | 0.01 | 944 | 100 | 2.9 |
| 3_1 | 15 mM citrate phosphate | 150 | 7.2 | 0.01 | 343 | 300 | 26.2 |
| 3_2 | 15 mM citrate phosphate | 150 | 7.2 | 0.01 | 343 | 250 | 12.2 |
| 3_3 | 15 mM citrate phosphate | 150 | 7.2 | 0.01 | 343 | 200 | 6.9 |
| 3_4 | 15 mM citrate phosphate | 150 | 7.2 | 0.01 | 343 | 100 | 2.9 |
| 4_1 | PBS | 150 | 7.4 | 0.01 | 307 | 300 | 28.2 |
| 4_2 | PBS | 150 | 7.4 | 0.01 | 307 | 250 | 14.9 |
| 4_3 | PBS | 150 | 7.4 | 0.01 | 307 | 200 | 7.4 |
| 4_3 | PBS | 150 | 7.4 | 0.01 | 307 | 100 | 2.8 |

6.3.2 Viscosity Behaviour at High Protein Concentration

Figure 19:
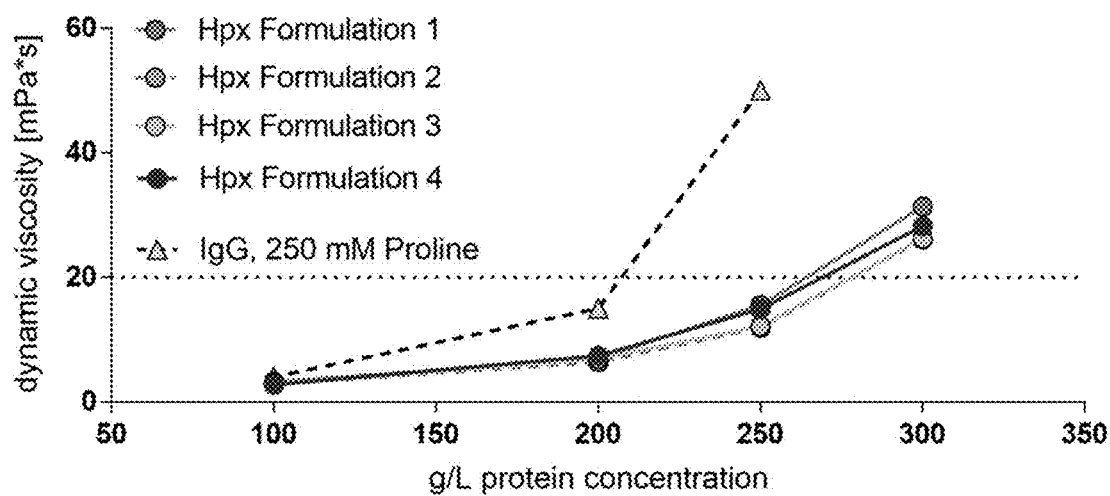
FIG. 19 shows viscosity behaviour at high protein concentrations of plasma derived human hemopexin. Formulations of different concentrations of hemopexin were prepared (Formulation 1: 200 mM citrate phosphate, 150 mM NaCl, 0.01% P80, pH 7.2; Formulation 2: 50 mM citrate phosphate, 400 mM NaCl, 0.01% P80, pH 7.2; Formulation 3: 15 mM citrate phosphate, 150 mM NaCl, 0.01% P80, pH 7.2; Formulation 4: PBS, 0.01% P80, pH 7.4) and their viscosities were compared to a viscosity curve of polyclonal IgG (triangle). Viscosity measurements were performed in duplicates on a rotational rheometer (HAAKE, ThermoScientific) at 25° C.

The viscosity behaviour of the prepared Hpx formulations was analyzed at the following protein concentrations (Table 21). As shown in FIG. 19 up to a target concentration of 250 g/L the viscosity remained below 20 mPa*s, which is considered as a permissive viscosity for any delivery system. W. Du & A. Klibanov, "Hydrophobic Salts Markedly Diminish Viscosity of Concentrated Protein Solutions", Biotechnology and Bioengineering, pp. 632-636, 2011. Note that these authors and others indicate the threshold for subcutaneous injections can be as high as 50 mPa*s. The study also demonstrated that each Hpx formulation at any given target protein concentration exhibited a similar viscosity. And as expected an increased target protein concentration was accompanied by an increased viscosity. Furthermore, as the protein concentration of these formulations was above the target levels (i.e. 100, 200, 250 and 300 mg/mL) the resultant viscosities were relatively higher compared to those measured in Example 1 (compare FIGS. 3D & 19). Finally, increased osmolarity (higher salt concentration) did not influence the viscosity significantly.

TABLE 21

Protein content and viscosity (at 25° C.) of formulations (Batch #C108.01).

| Formulation | A280 [g/L] | Viscosity [mPa*s] |
|---|---|---|
| 30_PBS, 0.01% P80, pH 7.4 | 321.91 | 28.20 |
| 25_PBS, 0.01% P80, pH 7.4 | 273.22 | 14.90 |
| 20_PBS, 0.01% P80, pH 7.4 | 222.18 | 7.40 |
| 10_PBS, 0.01% P80, pH 7.4 | 110.52 | 2.80 |
| 30_200 mM citrate phosphate, 150 mM NaCl, 0.01% P80, pH 7.2 | 315.87 | 31.40 |
| 25_200 mM citrate phosphate, 150 mM NaCl, 0.01% P80, pH 7.2 | 271.97 | 15.50 |
| 20_200 mM citrate phosphate, 150 mM NaCl, 0.01% P80, pH 7.2 | 205.07 | 6.90 |
| 10_200 mM citrate phosphate, 150 mM NaCl, 0.01% P80, pH 7.2 | 109.02 | 3.20 |

TABLE 21-continued

Protein content and viscosity (at 25° C.) of formulations (Batch #C108.01).

| Formulation | A280 [g/L] | Viscosity [mPa*s] |
|---|---|---|
| 30_50 mM citrate phosphate, 400 mM NaCl, 0.01% P80, pH 7.2 | 313.28 | 26.10 |
| 25_50 mM citrate phosphate, 400 mM NaCl, 0.01% P80, pH 7.2 | 261.64 | 11.90 |
| 20_50 mM citrate phosphate, 400 mM NaCl, 0.01% P80, pH 7.2 | 211.27 | 6.40 |
| 10_50 mM citrate phosphate, 400 mM NaCl, 0.01% P80, pH 7.2 | 105.42 | 2.90 |
| 30_15 mM citrate phosphate, 150 mM NaCl, 0.01% P80, pH 7.2 | 322.12 | 26.20 |
| 25_15 mM citrate phosphate, 150 mM NaCl, 0.01% P80, pH 7.2 | 270.24 | 12.20 |
| 20_15 mM citrate phosphate, 150 mM NaCl, 0.01% P80, pH 7.2 | 215.99 | 6.90 |
| 10_15 mM citrate phosphate, 150 mM NaCl, 0.01% P80, pH 7.2 | 103.19 | 2.90 |

6.3.3 Chemical Stability: $\Delta G$ and $\Delta\Delta G$ Determination Using the HUNK A small increase in the $\Delta G$ value of a protein can result in a 10× increase in the stability of the protein (see Table 22 below).

TABLE 22

Importance of $\Delta G$ upon chemical denaturation

| $\Delta G$ Kcal/mol | Stability | Fraction Denatured |
|---|---|---|
| 9.6 | Low Denaturation | 1/10,000,000 |
| 8.2 | Low Denaturation | 1/1,000,000 |
| 6.8 | Low Denaturation | 1/100,000 |
| 5.5 | Moderate Denaturation | 1/10,000 |
| 4.1 | Moderate Denaturation | 1/1000 |
| 2.7 | High Denaturation | 1/100 |
| 1.3 | High Denaturation | 1/10 |
| 0 | High Denaturation | 1/2 |

Figure 20:
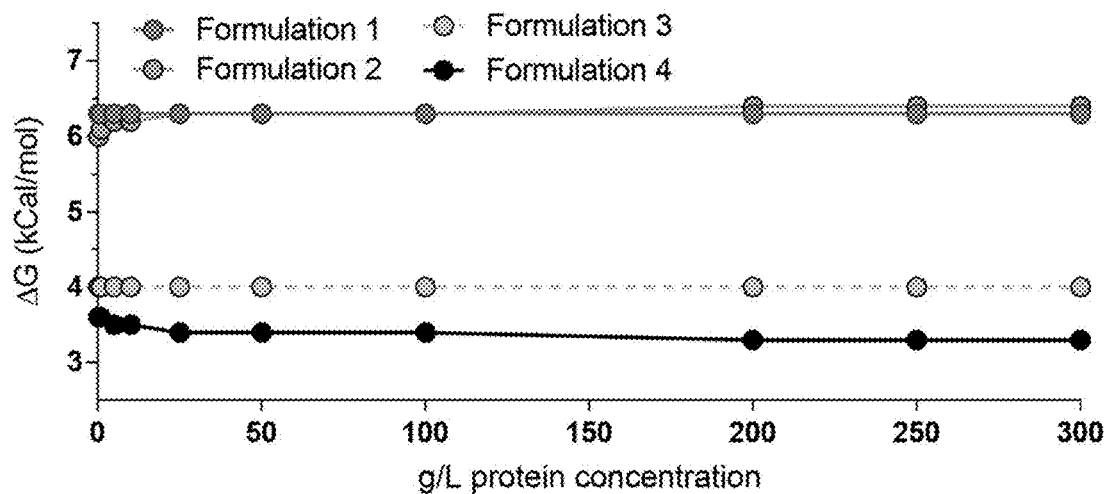
FIG. 20 shows the ΔG Trend using the HUNK automated chemical denaturation system. A 36-point denaturation curve in 0-8M urea was generated for Hpx at concentrations of 0.25, 1, 5, 10, 25, 50, 100, 150, 250, and 300 mg/mL. Each curve represents a single run for each formulation.
Figure 21:
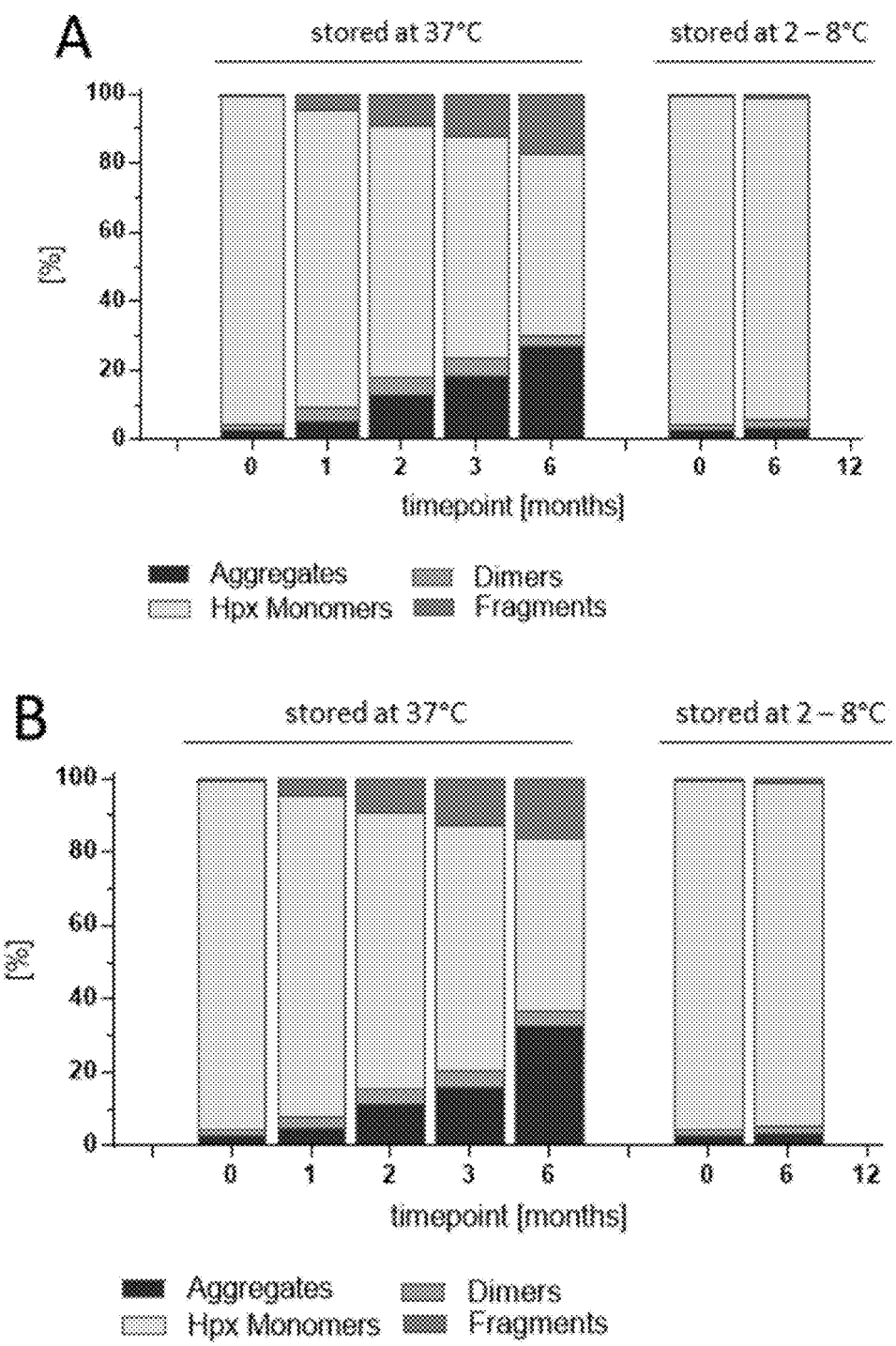
FIG. 21 shows SEC-HPLC data of different concentrated Hpx formulation 1 (200 mM citrate phosphate, 150 mM NaCl, 0.01% P80, pH 7.2) and analyzed over 6 months (A: 300; B: 250; C: 200 and D: 100 g/L). Molecular size distribution is presented as a 100% stacked column chart and each molecular species is shown as the respective amount in percentage. Aggregates and dimers are highlighted at the bottom of each column (black and grey, respectively); fragments are shown at the top of each column (grey).
Figure 21:
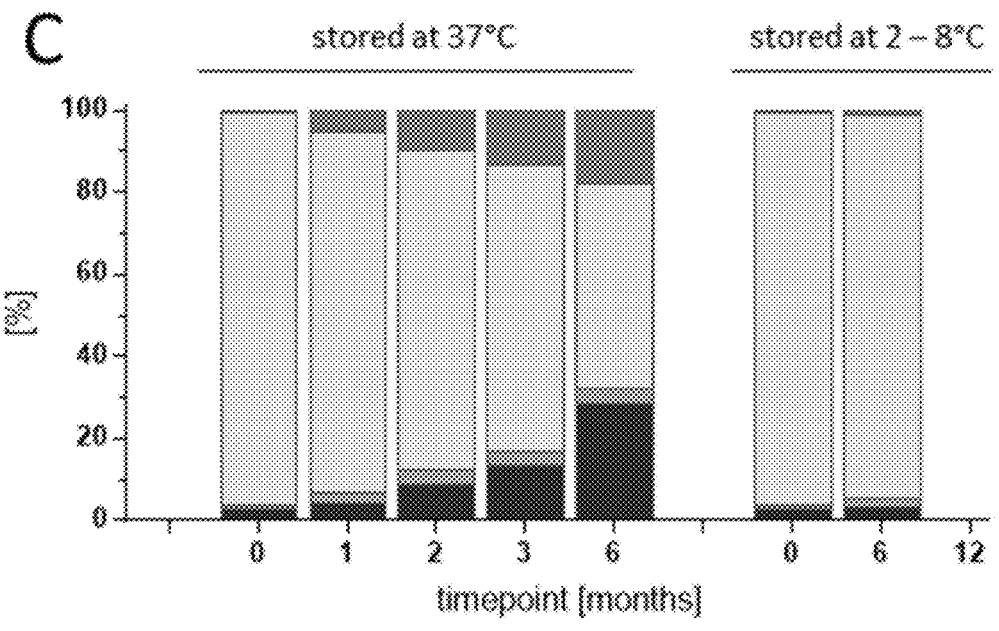
Figure 21:
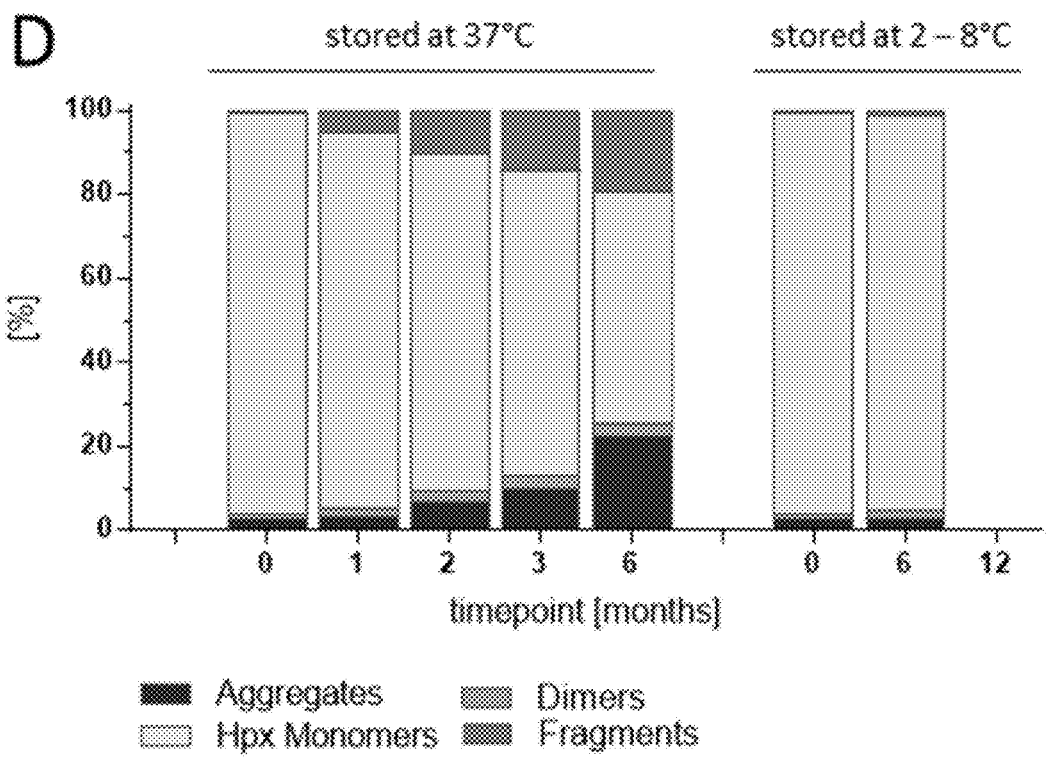
Figure 22:
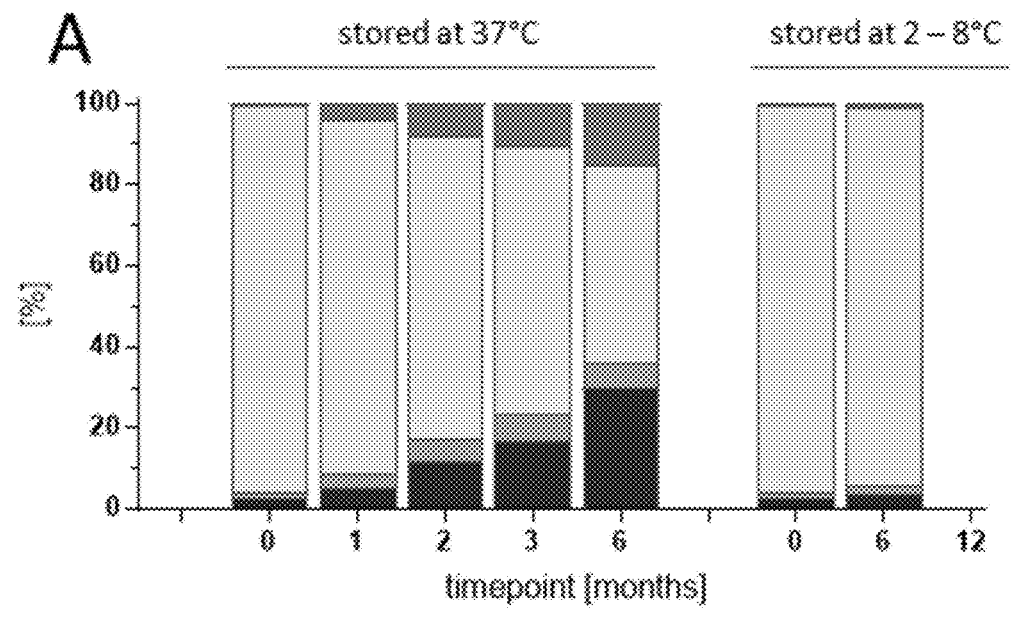
FIG. 22 shows SEC-HPLC data of different concentrated Hpx formulation 2 (50 mM citrate phosphate, 400 mM NaCl, 0.01% P80, pH 7.2) and analyzed over 6 months (A: 300; B: 250; C: 200 and D: 100 g/L). Molecular size distribution is presented as a 100% stacked column chart and each molecular species is shown as the respective amount in percentage. Aggregates and dimers are highlighted at the bottom of each column (black and grey, respectively); fragments are shown at the top of each column (grey).
Figure 22:
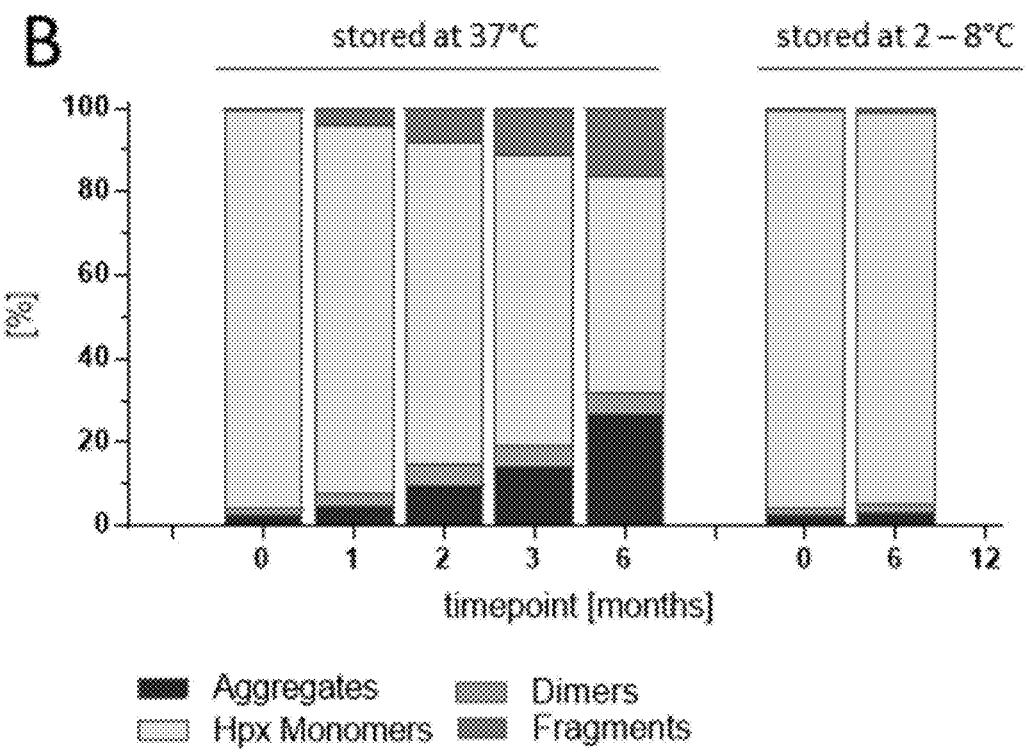
Figure 22:
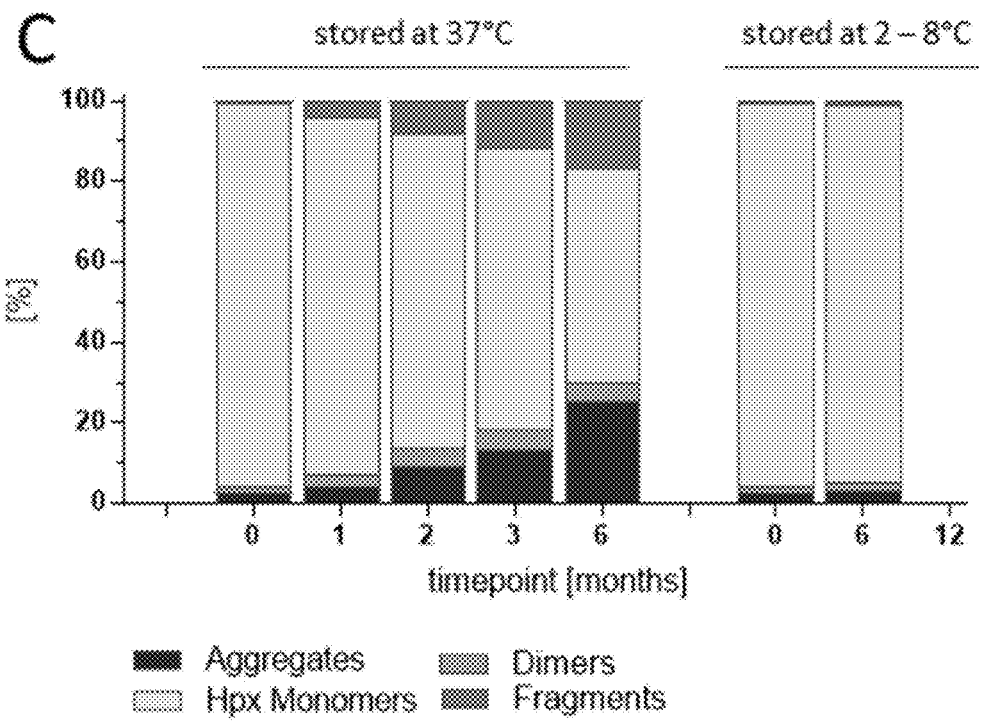
Figure 22:
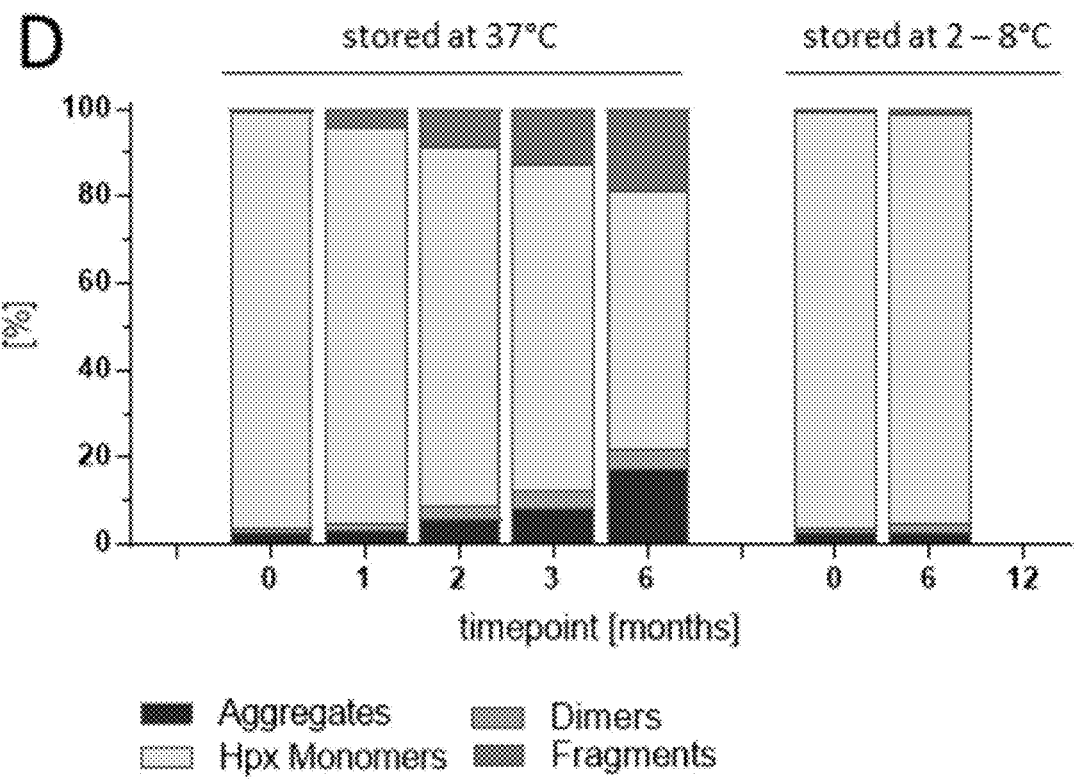
Figure 23:
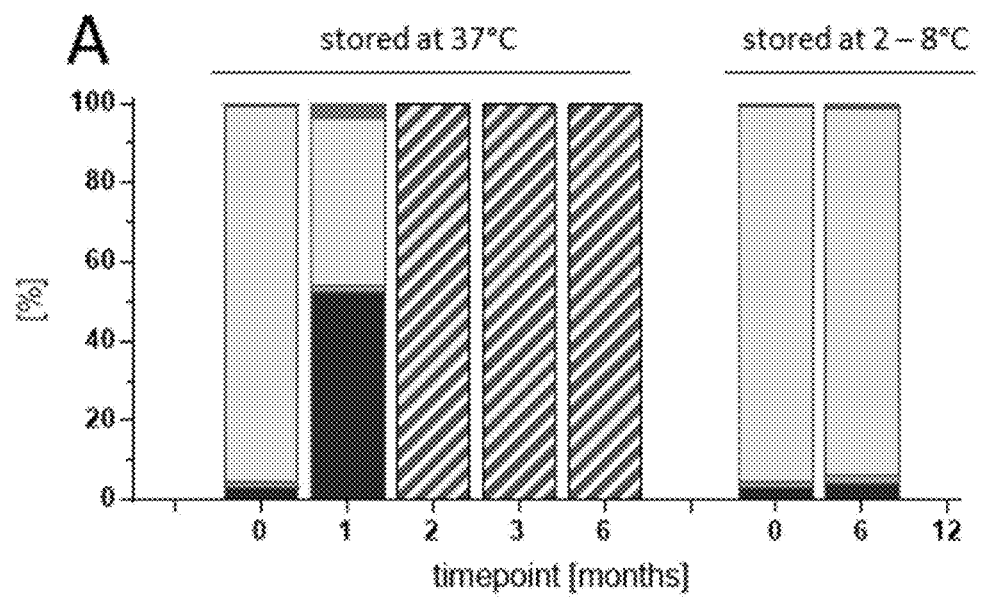
FIG. 23 shows SEC-HPLC data of different concentrated Hpx formulation 3 (15 mM citrate phosphate, 150 mM NaCl, 0.01% P80, pH 7.2) and analyzed over 6 months (A: 300; B: 250; C: 200 and D: 100 g/L). Molecular size distribution is presented as a 100% stacked column chart and each molecular species is shown as the respective amount in percentage. Dashed bars—formulation could not be analyzed due to gelation after a certain time point. Aggregates and dimers are highlighted at the bottom of each column (black and grey, respectively); fragments are shown at the top of each column (grey).
Figure 23:
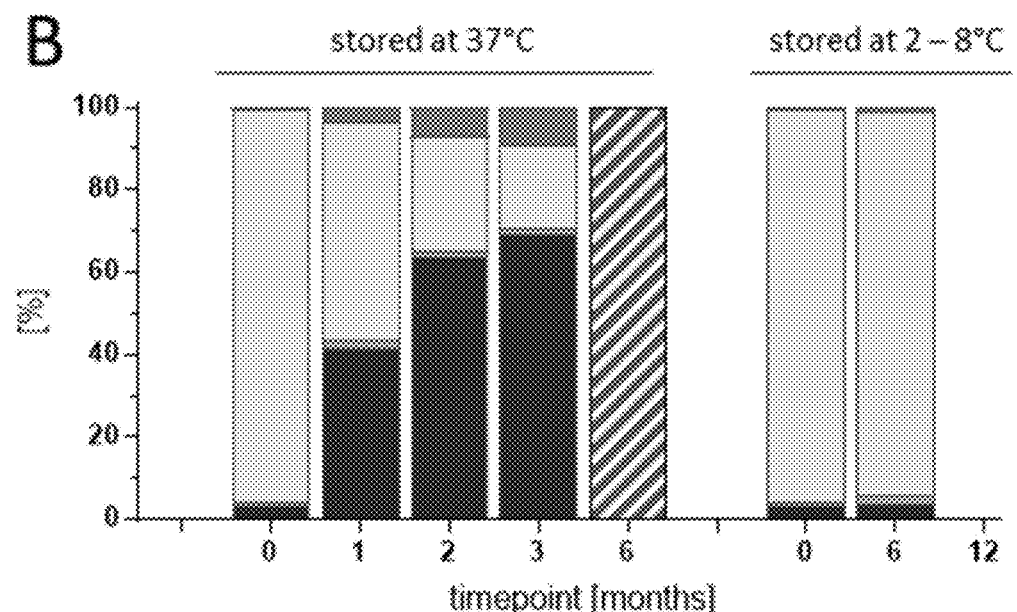
Figure 23:
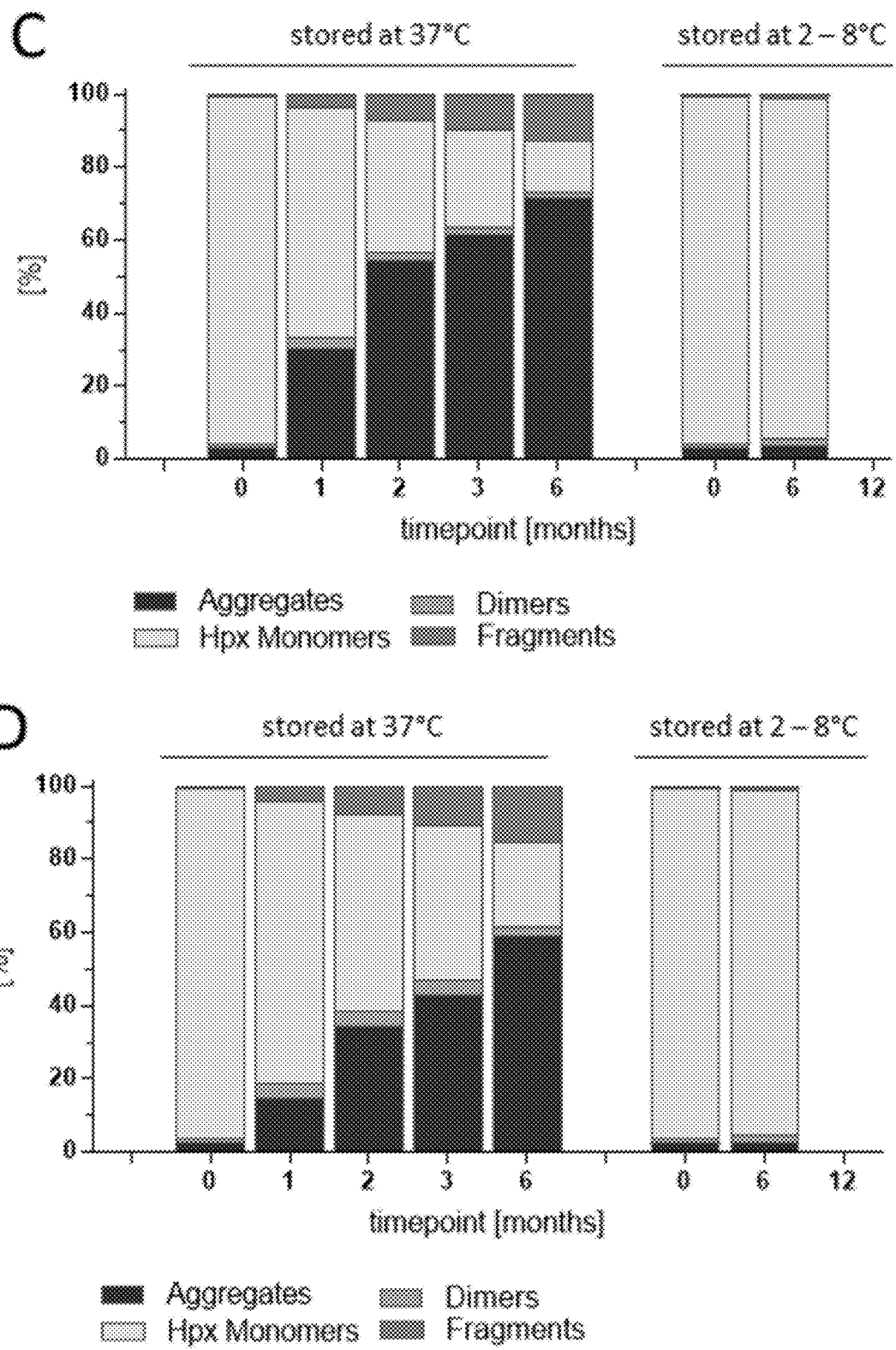
Figure 24:
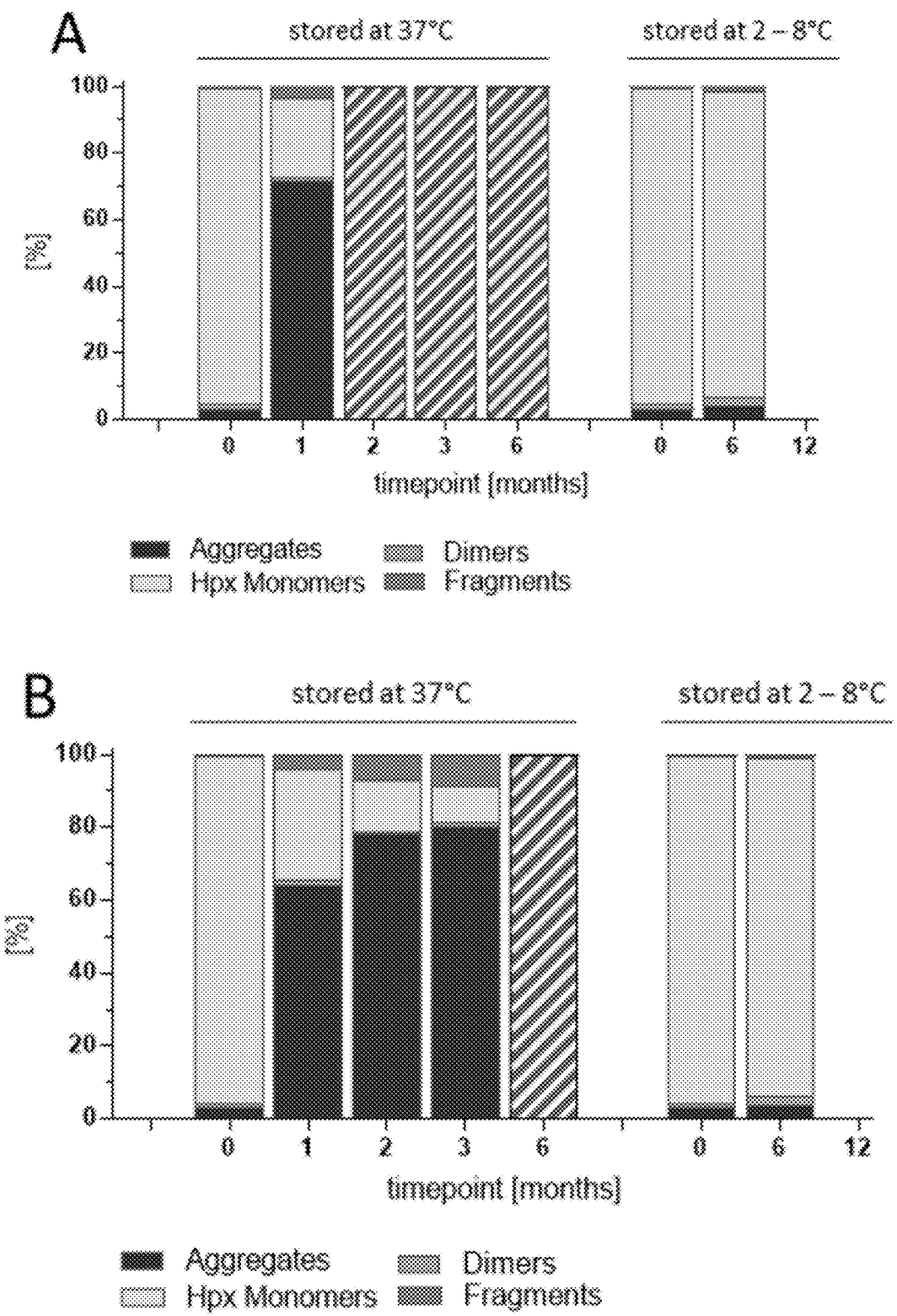
FIG. 24 shows SEC-HPLC data of different concentrated Hpx formulation 4 (PBS, 0.01% P80, pH 7.4) and analyzed over 6 months (A: 300; B: 250; C: 200 and D: 100 g/L). Molecular size distribution is presented as a 100% stacked column chart and each molecular species is shown as the respective amount in percentage. Dashed bars—formulation could not be analyzed due to gelation after a certain time point. Aggregates and dimers are highlighted at the bottom of each column (black and grey, respectively); fragments are shown at the top of each column (grey).
Figure 24:
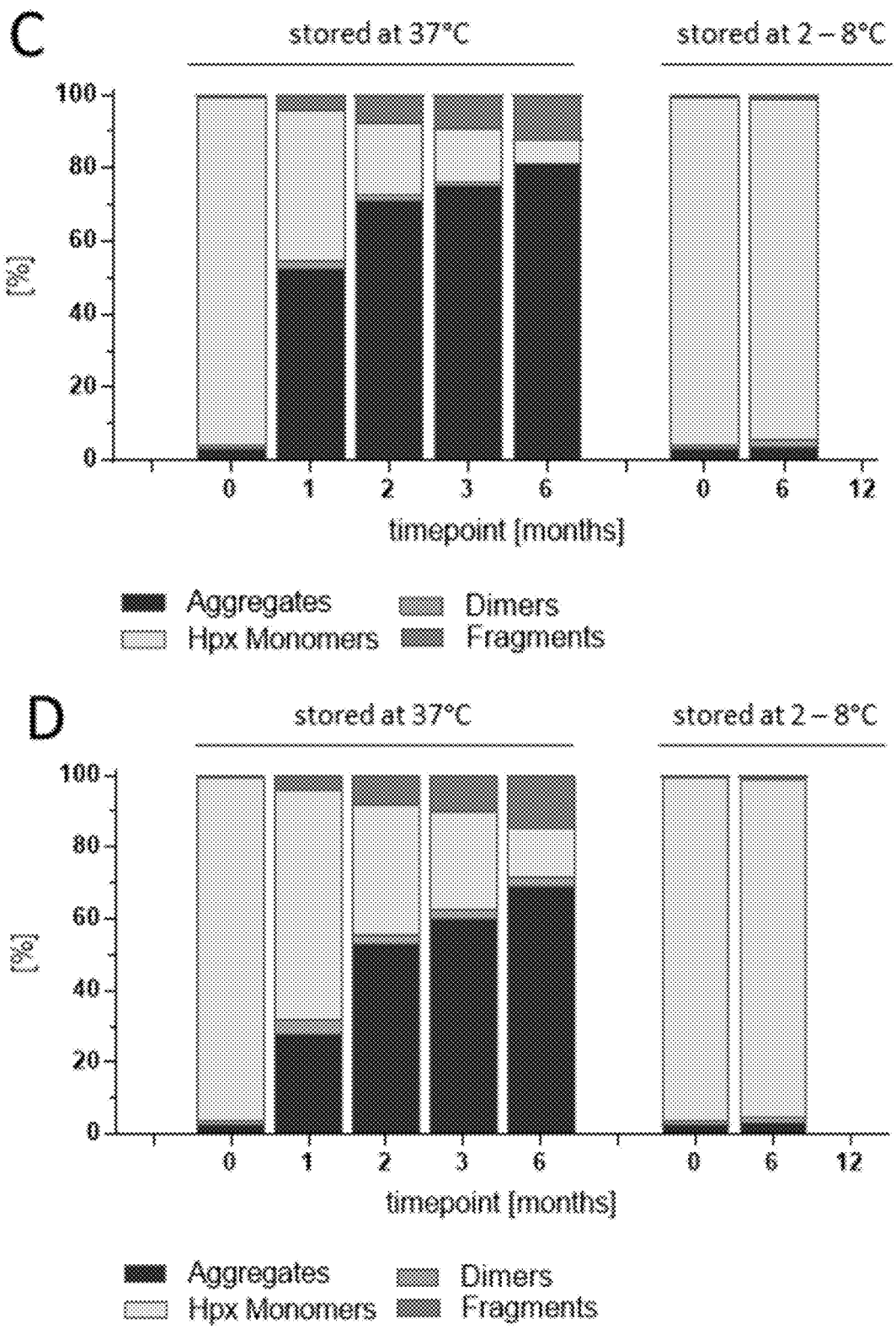

A protein in its most stable form will typically exhibit high $\Delta G$ values that are not concentration dependent (i.e., a flat line). A ten-point $\Delta G$ trend was generated at Hpx concentrations of 0.25, 1, 5, 10, 25, 50, 100, 200, 250 and 300 mg/mL to determine the stability and aggregation state in each formulation (see section 3.2.2). $\Delta G$ trend results are shown in FIG. 20.

In Formulations 1 and 2, Hpx exhibited $\Delta G$ values greater than 6.0 kCal/mol at all the concentrations analyzed. This indicated that Hpx was very stable in these two formulations with very low amounts of denatured protein present; however, Hpx in Formulation 2 was slightly less stable than in 1 due to the slight upward $\Delta G$ trend indicating the presence of aggregation in the native state.

In contrast to Formulations 1 and 2, the $\Delta G$ values in Formulations 3 and 4 were much lower indicating higher levels of denatured Hpx. Formulation 3 offered more stability than Formulation 4 with only moderate levels of denatured protein for the former compared to moderate-high levels for the latter. In addition, Hpx in formulation 4 was exhibiting aggregation in the denatured state based on the downward $\Delta G$ trend while the trend of Formulation 3 was unaffected by concentration. These results also confirmed the stability obtained by including citrate in the formulation.

In summary, Formulations 1, 2 and 3 effectively stabilized Hpx with only moderate to low levels of denatured protein present. In contrast, Formulation 4 stabilized the Hpx the least with high levels of denatured protein present that aggregated in the denatured state. Citrate contributed to the stability of Hpx as indicated by the greater stability observed in Formulation 3 compared to Formulation 4.

6.3.4 Molecular Size Distribution Over Time at High Protein Concentration

Formulations 1-4 were additionally stored for at least 6 months protected from light at 37° C. and 2-8° C. At each time point, samples were taken and subjected to SEC-HPLC analysis to monitor for monomers, oligomers and fragments of Hpx. The molecular size distribution results for each concentration after 6 months are shown in FIGS. 21-24 and Tables 23 and 24, below.

Following 37° C. storage, each of the Hpx formulations showed an increase in aggregates and fragments over time. Hpx formulated with high osmolarity formulations appeared to be the more stable and only a slight increase in protein aggregates was observed with increasing protein concentration analyzed at the same time point. In contrast, low excipient concentrations at high protein concentration resulted in strong aggregation and even protein gelation after a certain time period (Formulation 3 and 4). Since a storage temperature of 2-8° C. was chosen, based on earlier data, all formulations were kept at 2-8° C. as well and analyzed after 6 months. No significant changes in aggregates and fragments were observed between the different formulations if stored at 2-8° C. Monomeric Hpx (>93%) remained stable throughout the 6-month study period under these storage conditions, which was observed independently of the formulation and protein concentration.

TABLE 23

SEC-HPLC data after storage at 37° C. for 6 months

| No | Formulation | Protein Conc. [g/L] | Aggregates [%] | Dimers [%] | Monomers [%] | Fragments [%] |
|---|---|---|---|---|---|---|
| 1_1 | 200 mM citrate phosphate, 150 mM NaCl, 0.01% P80, pH 7.2 | 300 | 26.88 | 3.50 | 52.12 | 17.51 |
| 1_2 | 200 mM citrate phosphate, 150 mM NaCl, 0.01% P80, pH 7.2 | 250 | 32.57 | 3.90 | 47.07 | 16.46 |
| 1_3 | 200 mM citrate phosphate, 150 mM NaCl, 0.01% P80, pH 7.2 | 200 | 28.41 | 3.52 | 50.42 | 17.65 |
| 1_4 | 200 mM citrate phosphate, 150 mM NaCl, 0.01% P80, pH 7.2 | 100 | 22.77 | 3.08 | 54.64 | 19.50 |
| 2_1 | 50 mM citrate phosphate, 400 mM NaCl, 0.01% P80, pH 7.2 | 300 | 29.97 | 6.11 | 48.81 | 15.11 |

TABLE 23-continued

SEC-HPLC data after storage at 37° C. for 6 months

| No | Formulation | Protein Conc. [g/L] | Aggregates [%] | Dimers [%] | Monomers [%] | Fragments [%] |
|---|---|---|---|---|---|---|
| 2_2 | 50 mM citrate phosphate, 400 mM NaCl, 0.01% P80, pH 7.2 | 250 | 27.13 | 4.83 | 51.93 | 16.11 |
| 2_3 | 50 mM citrate phosphate, 400 mM NaCl, 0.01% P80, pH 7.2 | 200 | 25.50 | 4.57 | 53.10 | 16.84 |
| 2_4 | 50 mM citrate phosphate, 400 mM NaCl, 0.01% P80, pH 7.2 | 100 | 17.38 | 4.20 | 59.83 | 18.59 |
| 3_1 | 15 mM citrate phosphate, 150 mM NaCl, 0.01% P80, pH 7.2 | 300 | Formulation could not be analyzed due to gelation after 2 months | | | |
| 3_2 | 15 mM citrate phosphate, 150 mM NaCl, 0.01% P80, pH 7.2 | 250 | Formulation could not be analyzed due to gelation after 6 months | | | |
| 3_3 | 15 mM citrate phosphate, 150 mM NaCl, 0.01% P80, pH 7.2 | 200 | 71.96 | 1.31 | 13.88 | 12.85 |
| 3_4 | 15 mM citrate phosphate, 150 mM NaCl, 0.01% P80, pH 7.2 | 100 | 59.31 | 2.56 | 22.86 | 15.27 |
| 4_1 | PBS, 0.01% P80, pH 7.4 | 300 | Formulation could not be analyzed due to gelation after 2 months | | | |
| 4_2 | PBS, 0.01% P80, pH 7.4 | 250 | Formulation could not be analyzed due to gelation after 6 months | | | |
| 4_3 | PBS, 0.01% P80, pH 7.4 | 200 | 81.22 | 0.06 | 6.56 | 12.15 |
| 4_4 | PBS, 0.01% P80, pH 7.4 | 100 | 69.42 | 2.12 | 14.02 | 14.44 |

TABLE 24

SEC-HPLC data after storage at 2-8° C. for 6 months

| No | Formulation | Protein Conc. [g/L] | Aggregates [%] | Dimers [%] | Monomers [%] | Fragments [%] |
|---|---|---|---|---|---|---|
| 1_1 | 200 mM citrate phosphate, 150 mM NaCl, 0.01% P80, pH 7.2 | 300 | 3.63 | 2.03 | 93.09 | 1.26 |
| 1_2 | 200 mM citrate phosphate, 150 mM NaCl, 0.01% P80, pH 7.2 | 250 | 3.47 | 1.95 | 93.30 | 1.28 |
| 1_3 | 200 mM citrate phosphate, 150 mM NaCl, 0.01% P80, pH 7.2 | 200 | 3.27 | 1.90 | 93.56 | 1.28 |
| 1_4 | 200 mM citrate phosphate, 150 mM NaCl, 0.01% P80, pH 7.2 | 100 | 2.88 | 1.81 | 94.02 | 1.29 |
| 2_1 | 50 mM citrate phosphate, 400 mM NaCl, 0.01% P80, pH 7.2 | 300 | 3.54 | 2.12 | 93.23 | 1.12 |
| 2_2 | 50 mM citrate phosphate, 400 mM NaCl, 0.01% P80, pH 7.2 | 250 | 3.35 | 2.01 | 93.50 | 1.13 |
| 2_3 | 50 mM citrate phosphate, 400 mM NaCl, 0.01% P80, pH 7.2 | 200 | 3.20 | 2.05 | 93.62 | 1.13 |
| 2_4 | 50 mM citrate phosphate, 400 mM NaCl, 0.01% P80, pH 7.2 | 100 | 2.78 | 1.83 | 94.22 | 1.16 |
| 3_1 | 15 mM citrate phosphate, 150 mM NaCl, 0.01% P80, pH 7.2 | 300 | 3.97 | 2.18 | 92.77 | 1.08 |
| 3_2 | 15 mM citrate phosphate, 150 mM NaCl, 0.01% P80, pH 7.2 | 250 | 3.72 | 2.06 | 93.07 | 1.15 |
| 3_3 | 15 mM citrate phosphate, 150 mM NaCl, 0.01% P80, pH 7.2 | 200 | 3.50 | 2.02 | 93.36 | 1.12 |
| 3_4 | 15 mM citrate phosphate, 150 mM NaCl, 0.01% P80, pH 7.2 | 100 | 2.89 | 1.94 | 94.03 | 1.14 |
| 4_1 | PBS, 0.01% P80, pH 7.4 | 300 | 4.33 | 2.65 | 91.53 | 1.49 |
| 4_2 | PBS, 0.01% P80, pH 7.4 | 250 | 3.91 | 2.22 | 92.75 | 1.12 |
| 4_3 | PBS, 0.01% P80, pH 7.4 | 200 | 3.64 | 2.18 | 93.07 | 1.11 |
| 4_4 | PBS, 0.01% P80, pH 7.4 | 100 | 3.08 | 1.85 | 93.94 | 1.13 |

6.3.5 Conclusion

The results of the chemical denaturation testing show that Hpx was most stable in Formulation 1, followed by Formulation 2. Formulation 3, which contained citrate at near physiological osmolarity, offered more stability to Hpx in chemical denaturation analysis than Formulation 4 (PBS control). These data generated by chemical denaturation are consistent with the stability study data assessed by SEC-HPLC analyzed over time.

15 mM citrate phosphate improves the stability of Hpx, as evidenced by the results of thermal stability, chemical denaturation, oligorimerization and fragmentation testing, resulting in a superior performance in comparison to PBS alone. Importantly, stability was not significantly lost by increasing the concentration of Hpx in Formulation 1, 2, and 3 from 100 g/L to 300 g/L, as evidenced by the chemical denaturation data and the SEC-HPLC data, even when the Hpx formulations were stored at 2-8° C. over 6 months.

The invention claimed is:

1. A stable liquid formulation of purified hemopexin comprising:
   (a) a hemopexin content ranging from 50 mg/mL to 405 mg/mL;
   (b) a content of citrate phosphate buffer ranging from 15 mM to 200 mM;
   (c) a pH from 7.0 to 7.6; and
   (d) a content of sodium chloride ranging from 150 mM to 400 mM;
   wherein the liquid formulation comprises at least 90% hemopexin with heme binding activity when stored at 2-8° C. for six months.

2. The stable liquid formulation of claim 1 comprising from 75 mg/mL to 300 mg/mL hemopexin.

3. The stable liquid formulation of claim 2 comprising from 100 mg/mL to 200 mg/mL hemopexin.

4. The stable liquid formulation of claim 2 comprising from 200 mg/mL to 300 mg/mL hemopexin.

5. The stable liquid formulation of claim 2 comprising 200 mg/mL hemopexin.

6. The stable liquid formulation of claim 2 comprising 250 mg/mL hemopexin.

7. The stable liquid formulation of claim 2 comprising 300 mg/mL hemopexin.

8. The stable liquid formulation of claim 1 comprising from 15 mM to 200 mM citrate phosphate and from 150 mM to 250 mM sodium chloride.

9. The stable liquid formulation of claim 1 comprising 200 mM citrate phosphate and 150 mM sodium chloride.

10. The stable liquid formulation of claim 1 comprising 50 mM citrate phosphate and 400 mM sodium chloride.

11. The stable liquid formulation of claim 1 comprising 15 mM citrate phosphate and 150 mM sodium chloride.

12. The stable liquid formulation of claim 1, wherein the pH is 7.2.

13. The stable liquid formulation of claim 1, further comprising a non-ionic detergent.

14. The stable liquid formulation of claim 13, wherein the non-ionic detergent is polysorbate 80.

15. The stable liquid formulation of claim 13, wherein the non-ionic detergent is present in an amount of at least 0.0005% v/v.

16. The stable liquid formulation of claim 15, wherein the non-ionic detergent is present in an amount of less than 0.01% v/v.

17. The stable liquid formulation of claim 1, comprising a viscosity of less than 20 mPa*S when measured at 25° C.

18. The stable liquid formulation of claim 1, wherein the purified hemopexin comprises at least 95% by weight of total protein as determined by measuring the hemopexin content by immunonephelometry and the total protein content by the Bradford method or UV spectroscopy at 280 nm.

19. The stable liquid formulation of claim 1, wherein the purified hemopexin is derived from human plasma, or is selected from the group consisting of a recombinant hemopexin, a hemopexin variant, and a fusion protein comprising hemopexin or a heme binding fragment thereof.

20. The stable liquid formulation of claim 19, wherein the purified hemopexin is recovered from a plasma fraction derived from at least 500 kg of human plasma.

21. The stable liquid formulation of claim 1, comprising at least 70% hemopexin monomers when stored at 37° C. for 1 month.

22. The stable liquid formulation of claim 1, comprising at least 50% hemopexin monomers when stored at 37° C. for 2 months.

23. The stable liquid formulation of claim 1, comprising at least 50% hemopexin monomers when stored at 37° C. for 3 months.

24. The stable liquid formulation of claim 21, comprising at least 80% hemopexin monomers when stored at 37° C. for 1 month.

25. The stable liquid formulation of claim 22, comprising at least 70% hemopexin monomers when stored at 37° C. for 2 months.

26. The stable liquid formulation of claim 23, comprising at least 60% hemopexin monomers when stored at 37° C. for 3 months.

27. A method of treating a condition associated with hemolysis, the method comprising administering to a subject in need thereof the stable liquid formulation of claim 1.

28. The method of claim 27, wherein the condition associated with hemolysis is selected from an acute hemolytic condition and/or a chronic hemolytic condition.

29. The method of claim 27, wherein the condition is selected from the group consisting of hemolytic anemia, aplastic crisis, hyper-hemolytic crisis, transfusion-induced hemolysis, hemolytic uremic syndrome, myocardial infarcts, acute chest syndrome, pulmonary hypertension, leg ulcers, growth retardation, bone infarcts, pre-eclampsia, renal failure, acute kidney injury, acute respiratory distress syndrome (ARDS), stroke, intra-cranial hemorrhage (ICH), splenic sequestration, splenic infarcts, an autoimmune disease, microbial infection or increased susceptibility to infection, malaria infection, trauma, a transplant related condition, open heart surgery using cardiopulmonary bypass, and burns.

30. The method of claim 27, wherein the condition is selected from the group consisting of sickle cell anemia, hereditary spherocytosis, hereditary elliptocytosis, thalassemia, congenital dyserythropoietic anemia and paroxysmal nocturnal hemoglobinuria (PNH), systemic lupus erythematosus and chronic lymphocytic leukemia.

31. The method of claim 27, wherein the condition is selected from the group consisting of hemorrhagic stroke and intra-cranial hemorrhage (ICH).

32. The method of claim 27, wherein the condition is acute respiratory distress syndrome.

33. The method of claim 27, wherein the stable liquid formulation is administered intravenously.

34. The method of claim 27, wherein the stable liquid formulation is administered subcutaneously.

* * * * *

SEQUENCE LISTING

<160> NUMBER OF SEQ ID NOS: 1

<210> SEQ ID NO 1

```
<211> LENGTH: 462
<212> TYPE: PRT
<213> ORGANISM: Homo sapiens

<400> SEQUENCE: 1

Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Thr Ser Ala His
            20                  25                  30

Gly Asn Val Ala Glu Gly Thr Lys Pro Asp Pro Asp Val Thr Glu
            35                  40                  45

Arg Cys Ser Asp Gly Trp Ser Phe Asp Ala Thr Thr Leu Asp Asp Asn
    50                  55                  60

Gly Thr Met Leu Phe Phe Lys Gly Glu Phe Val Trp Lys Ser His Lys
65                  70                  75                  80

Trp Asp Arg Glu Leu Ile Ser Glu Arg Trp Lys Asn Phe Pro Ser Pro
                85                  90                  95

Val Asp Ala Ala Phe Arg Gln Gly His Asn Ser Val Phe Leu Ile Lys
            100                 105                 110

Gly Asp Lys Val Trp Val Tyr Pro Pro Glu Lys Lys Glu Lys Gly Tyr
        115                 120                 125

Pro Lys Leu Leu Gln Asp Glu Phe Pro Gly Ile Pro Ser Pro Leu Asp
    130                 135                 140

Ala Ala Val Glu Cys His Arg Gly Glu Cys Gln Ala Glu Gly Val Leu
145                 150                 155                 160

Phe Phe Gln Gly Asp Arg Glu Trp Phe Trp Asp Leu Ala Thr Gly Thr
                165                 170                 175

Met Lys Glu Arg Ser Trp Pro Ala Val Gly Asn Cys Ser Ser Ala Leu
            180                 185                 190

Arg Trp Leu Gly Arg Tyr Tyr Cys Phe Gln Gly Asn Gln Phe Leu Arg
        195                 200                 205

Phe Asp Pro Val Arg Gly Glu Val Pro Pro Arg Tyr Pro Arg Asp Val
    210                 215                 220

Arg Asp Tyr Phe Met Pro Cys Pro Gly Arg Gly His Gly His Arg Asn
225                 230                 235                 240

Gly Thr Gly His Gly Asn Ser Thr His His Gly Pro Glu Tyr Met Arg
                245                 250                 255

Cys Ser Pro His Leu Val Leu Ser Ala Leu Thr Ser Asp Asn His Gly
            260                 265                 270

Ala Thr Tyr Ala Phe Ser Gly Thr His Tyr Trp Arg Leu Asp Thr Ser
        275                 280                 285

Arg Asp Gly Trp His Ser Trp Pro Ile Ala His Gln Trp Pro Gln Gly
    290                 295                 300

Pro Ser Ala Val Asp Ala Ala Phe Ser Trp Glu Glu Lys Leu Tyr Leu
305                 310                 315                 320

Val Gln Gly Thr Gln Val Tyr Val Phe Leu Thr Lys Gly Gly Tyr Thr
                325                 330                 335

Leu Val Ser Gly Tyr Pro Lys Arg Leu Glu Lys Glu Val Gly Thr Pro
            340                 345                 350

His Gly Ile Ile Leu Asp Ser Val Asp Ala Ala Phe Ile Cys Pro Gly
        355                 360                 365

Ser Ser Arg Leu His Ile Met Ala Gly Arg Arg Leu Trp Trp Leu Asp
    370                 375                 380

Leu Lys Ser Gly Ala Gln Ala Thr Trp Thr Glu Leu Pro Trp Pro His
```

-continued

```
            385                 390                 395                 400
Glu Lys Val Asp Gly Ala Leu Cys Met Glu Lys Ser Leu Gly Pro Asn
                405                 410                 415

Ser Cys Ser Ala Asn Gly Pro Gly Leu Tyr Leu Ile His Gly Pro Asn
                420                 425                 430

Leu Tyr Cys Tyr Ser Asp Val Glu Lys Leu Asn Ala Ala Lys Ala Leu
            435                 440                 445

Pro Gln Pro Gln Asn Val Thr Ser Leu Leu Gly Cys Thr His
        450                 455                 460
```